US012653815B2

(12) United States Patent
Gibson et al.

(10) Patent No.: US 12,653,815 B2
(45) Date of Patent: Jun. 16, 2026

(54) LUMINALLY-ACTING N-(PIPERIDIN-4-YL)BENZAMIDE DERIVATIVES

(71) Applicant: Takeda Pharmaceutical Company Limited, Osaka (JP)

(72) Inventors: Tony S. Gibson, San Diego, CA (US); Steve Swann, San Diego, CA (US)

(73) Assignee: Takeda Pharmaceutical Company Limited, Osaka (JP)

(*) Notice: Subject to any disclaimer, the term of this patent is extended or adjusted under 35 U.S.C. 154(b) by 589 days.

(21) Appl. No.: 17/923,183

(22) PCT Filed: May 3, 2021

(86) PCT No.: PCT/US2021/030493
§ 371 (c)(1),
(2) Date: Nov. 3, 2022

(87) PCT Pub. No.: WO2021/225968
PCT Pub. Date: Nov. 11, 2021

(65) Prior Publication Data

US 2023/0158010 A1 May 25, 2023

Related U.S. Application Data

(60) Provisional application No. 63/019,829, filed on May 4, 2020.

(51) Int. Cl.

| | |
|---|---|
| ***A61K 31/4545*** | (2006.01) |
| ***A61K 31/4468*** | (2006.01) |
| ***A61K 31/4525*** | (2006.01) |
| ***A61K 31/675*** | (2006.01) |
| ***C07D 211/58*** | (2006.01) |
| ***C07D 405/12*** | (2006.01) |
| ***C07D 405/14*** | (2006.01) |
| ***C07F 9/59*** | (2006.01) |

(52) U.S. Cl.
CPC ...... *A61K 31/4545* (2013.01); *A61K 31/4468* (2013.01); *A61K 31/4525* (2013.01); *A61K 31/675* (2013.01); *C07D 211/58* (2013.01); *C07D 405/12* (2013.01); *C07D 405/14* (2013.01); *C07F 9/59* (2013.01)

(58) Field of Classification Search
CPC .............. A61K 31/675; A61K 31/4525; A61K 31/4468; A61K 31/4545
See application file for complete search history.

(56) References Cited

U.S. PATENT DOCUMENTS 5,185,335 A 2/1993 Van Daele et al.

FOREIGN PATENT DOCUMENTS

| | | | |
|---|---|---|---|
| CN | 1262621 A | | 8/2000 |
| JP | 2004-277318 A | | 10/2004 |
| TW | 200400186 A | | 1/2004 |
| TW | 201014592 A | | 4/2010 |
| WO | 2008114971 A1 | | 9/2008 |
| WO | WO 2008/114971 | * | 9/2008 |
| WO | 2010024586 A2 | | 3/2010 |
| WO | 2010162959 A1 | | 6/2010 |

OTHER PUBLICATIONS

Sakaguchi J. et al., "Synthesis and Gastrointestinal Prokinetic Activity of Novel Benzamide Derivatives With Amphoteric Side Chains", Chemical and Pharmaceutical Bulletin, Pharmaceutical Society of Japan, JP, vol. 49, No. 4, Apr. 1, 2001 (Apr. 1, 2001), p. 424-436.
Lihong P. et al., Practical Therapeutics Pharmacology, Jilin Science and Technology Press, pp. 11-16, 1st Edition in Mar. 2018.
Seach Report w English Translation Taiwan Application No. 110116059, dated Jan. 19, 2025, 3 pages.
Seach Report w English Translation, Chinese Application No. 202180033067.3, dated Jan. 19, 2025, 5 pages.
Sonda S. et al., "Synthesis and pharmacological evaluation of benzamide derivatives as selective 5-HT4 receptor agonists", Bioorganic & Medicinal Chemistry, 2005, No. 13, pp. 3295-3308.

* cited by examiner

*Primary Examiner* — Marcos L Sznaidman
(74) *Attorney, Agent, or Firm* — Honigman LLP; Lucy X. Yang; Jonathan P. O'Brien

(57) ABSTRACT

Disclosed are compounds of Formula 1, and pharmaceutically acceptable salts thereof, wherein m, $R^1$, $R^2$, $R^3$, $R^4$, $R^5$, $R^6$, $X^1$, $X^2$, $X^3$ and $X^4$ are defined in the specification. This disclosure also relates to materials and methods for preparing compounds of Formula 1, to pharmaceutical compositions which contain them, and to their use for treating diseases, disorders, and conditions associated with the 5-$HT_4$ receptor.

(1)

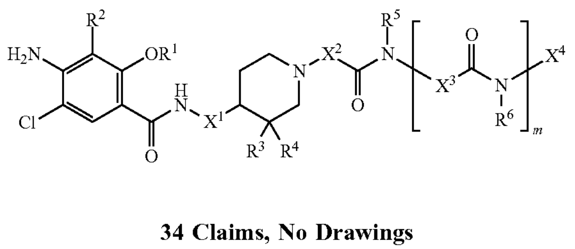

34 Claims, No Drawings

LUMINALLY-ACTING N-(PIPERIDIN-4-YL)BENZAMIDE DERIVATIVES

CROSS-REFERENCE TO RELATED APPLICATIONS

This application is a 35 USC § 371 National Stage filing of International Application No. PCT/US2021/030493, filed May 3, 2021, which claims the benefit of priority to U.S. Provisional Application No. 63/019,829, filed Mar. 4, 2020. The entire contents of the aforementioned applications are incorporated herein by reference in their entireties.

FIELD OF THE INVENTION

This invention relates to luminally-acting N-(piperidin-4-yl)benzamide derivatives, which are selective agonists of the 5-$HT_4$ receptor, to pharmaceutical compositions which contain them, and to their use to treat diseases, disorders, and conditions associated with the 5-$HT_4$ receptor, including gastrointestinal motility disorders.

BACKGROUND OF THE INVENTION

Serotonin (5-hydroxytryptamine, 5-HT) is a signaling molecule that activates a family of 5-HT receptors expressed throughout the central and peripheral nervous system. In the gastrointestinal (GI) tract, 5-HT receptors are expressed within the enteric nervous system (ENS) and have been shown to play a critical role in GI functions such as secretion, motility, and perception of visceral pain. See G. M. Mawe & J. M. Hoffman, "Serotonin Signalling in the Gut—Functions, Dysfunctions and Therapeutic Targets," *Nature Reviews Gastroenterology and Hepatology* 10:473 (2013). One such receptor of this family, the 5-$HT_4$ receptor (5-$HT_4$R), potentiates excitatory neurotransmission in the ENS through a presynaptic mechanism, and activation of this receptor causes propulsive motility. See, e.g., D. A. Craig & D. E. Clarke, "Pharmacological Characterization of a Neuronal Receptor for 5-Hydroxytryptamine in Guinea Pig Ileum with Properties Similar to the 5-Hydroxytryptamine Receptor," *J Pharmacol Exp Ther* 252:1378-1386 (1990); M. Tonini M, S. M. Candura, L. Onori, et al.,"5-Hydroxytryptamine4 Receptor Agonists Facilitate Cholinergic Transmission in the Circular Muscle of Guinea Pig Ileum: Antagonism by Tropisetron and Dau 6285," *Life Sci* 50: PL173-178 (1992); A. E. Foxx-Orenstein, J. F. Kuemmerle & J. R. Grider, "Distinct 5-Ht Receptors Mediate the Peristaltic Reflex Induced by Mucosal Stimuli in Human and Guinea Pig Intestine," *Gastroenterology* 111:1281-1290 (1996); M. Kadowaki, P. R. Wade & M. D. Gershon, "Participation of 5-Ht3, 5-Ht4, and Nicotinic Receptors in the Peristaltic Reflex of Guinea Pig Distal Colon," *Amer J Physiol-Gastrointest L* 34: G849-G857 (1996); J. R. Grider, A. E. Foxx-Orenstein & J-G Jin, "5-Hydroxytryptamine4 Receptor Agonists Initiate the Peristaltic Reflex in Human, Rat, and Guinea Pig Intestine," *Gastroenterology* 115:370-380 (1998); J-G Jin, A, E Foxx-Orenstein & J. Grider, "Propulsion in Guinea Pig Colon Induced by 5-Hydroxytryptamine (Ht) Via 5-Ht4 and 5-Ht3 Receptors," *Journal of Pharmacology and Experimental Therapeutics* 288:93-97 (1999); J. R. Grider, "Desensitization of the Peristaltic Reflex Induced by Mucosal Stimulation with the Selective 5-Ht4 Agonist Tegaserod," *Am J Physiol Gastrointest Liver Physiol* 290: G319-327 (2006). As a result, 5-$HT_4$R agonists have been developed for the treatment of constipation. These agonists, which include drugs such as cisapride, tegaserod, and prucalopride, are effective prokinetic agents. However, due to off-target side effects associated with potential adverse safety events in the case of cisapride and tegaserod, clinical use has been limited. In addition, because 5-$HT_4$ receptors are expressed throughout the central and peripheral nervous system, possible on-target side effects such as suicidality remain a concern and are reflected in the label for some of these drugs.

In addition to expression in neurons, it has been shown that 5-$HT_4$ receptors are expressed in the colonic epithelium of the GI tract in mouse, rat, guinea pig, and human. See J. M. Hoffman, K. Tyler, S. J. MacEachern, et al., "Activation of Colonic Mucosal 5-Ht4 Receptors Accelerates Propulsive Motility and Inhibits Visceral Hypersensitivity," *Gastroenterology* 142:844-854. e844 (2012). Studies assessing in vitro motility in segments of guinea pig colon in response to the 5-$HT_4$R agonist tegaserod revealed a prokinetic effect when the compound was administered intra-luminally, but no effect when the compound was added to the bath. Id. These results suggest that the compound may agonize receptors to cause an effect on motility via the mucosa from the lumen that were not accessible from the serosa, supporting the hypothesis that colonic epithelial 5-$HT_4$ receptors are prokinetic. Mucosal application of 5-$HT_4$R agonists also caused release of 5-HT from enterochromaffin cells, mucus discharge, and $Cl^-$ secretion by enterocytes. These effects were blocked by a 5-$HT_4$R antagonist. Id. Further studies have shown that gut microbiota-derived tryptamine is an agonist of 5-$HT_4$ receptors expressed in the colonic epithelium and causes effects on secretion and GI transit in mice. See Y. Bhattarai, B. B. Williams, E. J. Battaglioli, et al., "Gut Microbiota-Produced Tryptamine Activates an Epithelial G-Protein-Coupled Receptor to Increase Colonic Secretion," *Cell Host Microbe* 23:775-785 e775 (2018). Considering these results regarding the expression and function of epithelial 5-$HT_4$ receptors, the site of action for the prokinetic effect of 5-$HT_4$ receptors in the colon may be in the mucosa, instead of or in addition to enteric nerve terminals within the ENS.

Beyond effects on motility, activation of epithelial 5-$HT_4$ receptors has been shown to be involved in resistance to oxidative stress and to epithelial migration and proliferation. See S. N. Spohn, F. Bianco, R. B. Scott, et al., "Protective Actions of Epithelial 5-Hydroxytryptamine 4 Receptors in Normal and Inflamed Colon," *Gastroenterology* 151:933-944 e933 (2016); C. J. Park, S. J. Armenia, L. Zhang, et al., "The 5-Ht4 Receptor Agonist Prucalopride Stimulates Mucosal Growth and Enhances Carbohydrate Absorption in the Ileum of the Mouse," *J Gastrointest Surg.* 23(6):1198-1205 (2019). These data suggest a possible protective function for epithelial 5-$HT_4$R agonism in response to damage. In fact, 5-$HT_4$R agonists administered by enema to the colon of mice in models of colitis result in decreased extent of disease and accelerated recovery from established disease. See Spohn (2016).

Thus, compounds which selectively activate 5-$HT_4$ receptors expressed in the epithelium of the GI tract may be prokinetic and/or have pro-healing effects in diseases that involve damage to the GI epithelium. Moreover, luminally-acting 5-$HT_4$R agonists, which exhibit minimal systemic absorption and thereby avoid activation of receptors in the ENS and other tissues accessed through systemic circulation, may offer an improved safety profile while treating diseases mediated through activation of epithelial 5-$HT_4$ receptors.

SUMMARY OF THE INVENTION

This invention provides luminally-acting N-(piperidin-4-yl)benzamide derivatives and pharmaceutically acceptable salts thereof. This invention also provides pharmaceutical compositions that contain the N-(piperidin-4-yl)benzamide derivatives and provides for their use to treat diseases, disorders and conditions associated with $5\text{-HT}_4R$.

One aspect of the invention provides compounds of Formula 1:

1

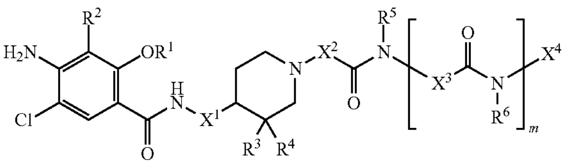

or a pharmaceutically acceptable salt thereof in which:

m is an integer selected from 0 and 1;

$R^1$ is methyl and $R^2$ is hydrogen, or $R^1$ and $R^2$ together form an ethane-1,2-diyl which bridges the oxygen and carbon atoms to which $R^1$ and $R^2$ are respectively attached;

$R^3$ and $R^4$ are each independently selected from hydrogen, halo, $C_{1-4}$ alkyl and $C_{1-3}$ alkoxy;

$R^5$ and $R^6$ are each independently selected from hydrogen and $C_{1-4}$ alkyl which is unsubstituted or substituted with an optional substituent selected from hydroxy, phosphono, sulfo and amino, wherein the amino optional substituent is unsubstituted or substituted with 1 or 2 optional substituents independently selected from $C_{1-3}$ alkyl;

$X^1$ is selected from a bond and methane-1,1-diyl;

$X^2$ is selected from (a) pentane-1,5-diyl which is unsubstituted or substituted with 1 to 5 optional substituents independently selected from halo and $C_{1-3}$ alkyl, wherein one of the carbon atoms of the pentane-1,5-diyl substituent may be optionally replaced with one oxygen atom, provided the oxygen atom is directly bonded to two carbon atoms within the pentane-1,5-diyl substituent; and (b) a moiety represented by the formula

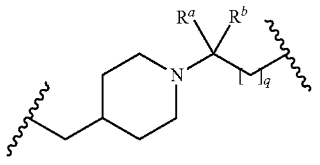

wherein $R^a$ and $R^b$ are each hydrogen or together represent oxo; and q is an integer selected from 1, 2, 3, 4, 5, 6, 7, 8, 9 and 10;

$X^3$ is selected from (a) $C_{1-11}$ alkanediyl, wherein 0 to 3 carbon atoms of the alkanediyl substituent may be optionally replaced, one-to-one, with oxygen atoms, provided each replacement oxygen atom is directly bonded to two carbon atoms within the alkanediyl substituent and any two replacement oxygen atoms are separated by at least one carbon atom; and (b) a moiety represented by the formula,

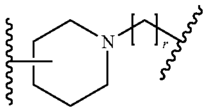

wherein r is an integer selected from 1, 2, 3, 4, 5, 6 and 7; and $X^4$ is selected from (a) $C_{3-6}$ alkyl which is substituted with 3 to 6 hydroxy substituents;

(b) $C_{1-3}$ alkyl which is substituted with phosphono or sulfo substituents; and (c) cyclohexyl which is substituted with 3 to 6 substituents independently selected from hydroxy and hydroxymethyl;

wherein the bracketed moieties in Formula 1 and in the formulas for $X^2$ and $X^3$ are present m, q or r times, respectively, and each 〰 represents a point of attachment in the formulas for $X^2$ and $X^3$.

Another aspect of the invention provides a compound which is selected from the group of compounds described in the examples and their pharmaceutically acceptable salts.

A further aspect of the invention provides a pharmaceutical composition which includes a compound of Formula 1 or a pharmaceutically acceptable salt thereof, or any one of the compounds or pharmaceutically acceptable salts defined in the preceding paragraph; and a pharmaceutically acceptable excipient.

An additional aspect of the invention provides a compound of Formula 1 or a pharmaceutically acceptable salt thereof, or any one of the compounds described in the examples or a pharmaceutically acceptable salt thereof, for use as a medicament.

Another aspect of the invention provides a compound of Formula 1 or a pharmaceutically acceptable salt thereof, or any one of the compounds described in the examples or a pharmaceutically acceptable salt thereof, for use in treating a disease, disorder or condition associated with $5\text{-HT}_4R$.

A further aspect of the invention provides a compound of Formula 1 or a pharmaceutically acceptable salt thereof, or any one of the compounds described in the examples or a pharmaceutically acceptable salt thereof, for use in treating a disease, disorder or condition selected from chronic idiopathic constipation, slow transit constipation, opioid-induced constipation, irritable bowel syndrome, Crohn's Disease, ulcerative colitis, enteral feeding intolerance, postoperative ileus, postoperative gastrointestinal dysfunction, diabetic gastroparesis, idiopathic gastroparesis, functional abdominal pain, chronic intestinal pseudo-obstruction, Hirschsprung Disease, Celiac Disease and short bowel syndrome.

An additional aspect of the invention provides a compound of Formula 1 or a pharmaceutically acceptable salt thereof, or any one of the compounds described in the examples or a pharmaceutically acceptable salt thereof, for the manufacture of a medicament for the treatment of a disease, disorder or condition associated with $5\text{-HT}_4R$.

Another aspect of the invention provides a method for activating $5\text{-HT}_4R$ in a subject, the method comprising administering to the subject a compound of Formula 1 or a pharmaceutically acceptable salt thereof, or any one of the compounds described in the examples or a pharmaceutically acceptable salt thereof.

A further aspect of the invention provides a method for treating a disease, disorder or condition associated with 5-$HT_4R$, the method comprising administering to the subject an effective amount of a compound of Formula 1 or a pharmaceutically acceptable salt thereof, or any one of the compounds described in the examples or a pharmaceutically acceptable salt thereof.

An additional aspect of the invention provides a method for treating a disease, disorder or condition in a subject, the method comprising administering to the subject an effective amount of a compound of Formula 1 or a pharmaceutically acceptable salt thereof, or any one of the compounds described in the examples or a pharmaceutically acceptable salt thereof, wherein the disease, disorder or condition is selected from gastrointestinal motility disorders.

Another aspect of the invention provides a method for treating a disease, disorder or condition in a subject, the method comprising administering to the subject an effective amount of a compound of Formula 1 or a pharmaceutically acceptable salt thereof, or any one of the compounds described in the examples or a pharmaceutically acceptable salt thereof, wherein the disease, disorder or condition is selected from chronic idiopathic constipation, slow transit constipation, opioid-induced constipation, irritable bowel syndrome, Crohn's Disease, ulcerative colitis, enteral feeding intolerance, postoperative ileus, postoperative gastrointestinal dysfunction, diabetic gastroparesis, idiopathic gastroparesis, functional abdominal pain, chronic intestinal pseudo-obstruction, Hirschsprung Disease, Celiac Disease and short bowel syndrome.

A further aspect of the invention provides a compound of Formula 1 or a pharmaceutically acceptable salt thereof, or any one of the compounds described in the examples or a pharmaceutically acceptable salt thereof; and at least one additional pharmacologically active agent.

DETAILED DESCRIPTION OF THE INVENTION

Unless otherwise indicated, this disclosure uses definitions provided below.

"Substituted," when used about a chemical substituent or moiety (e.g., a $C_{1-6}$ alkyl group), means that one or more hydrogen atoms of the substituent or moiety have been replaced with one or more non-hydrogen atoms or groups, provided valence requirements are met and a chemically stable compound results from the substitution.

"About" or "approximately," when used about a measurable numerical variable, refers to the indicated value of the variable and to all values of the variable that are within the experimental error of the indicated value or within ±10 percent of the indicated value, whichever is greater.

"Agonist" refers to both full agonists and partial agonists.

"Alkyl" refers to straight chain and branched saturated hydrocarbon groups, generally having a specified number of carbon atoms (e.g., $C_{1-4}$ alkyl refers to an alkyl group having 1 to 4 (i.e., 1, 2, 3 or 4) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkanediyl" refers to divalent alkyl groups, where alkyl is defined above, and generally having a specified number of carbon atoms (e.g., $C_{1-4}$ alkanediyl refers to an alkanediyl group having 1 to 4 (i.e., 1, 2, 3 or 4) carbon atoms, $C_{1-6}$ alkanediyl refers to an alkanediyl group having 1 to 6 carbon atoms, and so on). Examples of alkanediyl groups include methylene (methane-1,1-diyl), ethane-1,1-diyl, ethane-1,2-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, isobutane-1,3-diyl, isobutane-1,1-diyl, isobutane-1,2-diyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Alkoxy" refers to straight chain and branched saturated hydrocarbon groups attached through an oxygen atom, generally having a specified number of carbon atoms (e.g., $C_{1-4}$ alkoxy refers to an alkoxy group having 1 to 4 (i.e., 1, 2, 3 or 4) carbon atoms, $C_{1-6}$ alkoxy refers to an alkoxy group having 1 to 6 carbon atoms, and so on). Examples of alkoxy groups include methoxy, ethoxy, n-propoxy, i-propoxy, n-butoxy, s-butoxy, i-butoxy, t-butoxy, pent-1-yloxy, pent-2-yloxy, pent-3-yloxy, 3-methylbut-1-yloxy, 3-methylbut yloxy, 2-methylbut-2-yloxy, 2,2,2-trimethyleth-1-yloxy, n-hexoxy, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, 1-fluoroethyl, 1,1-difluoroethyl, 1-chloroethyl, 1,1-dichloroethyl, 1-fluoro-1-methylethyl, 1-chloro-1-methylethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements, and where indicated, may optionally include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]

heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo [2.1.1]hexanyl, bicyclo[2.2.1]heptanyl, bicyclo[3.1.1]heptanyl, bicyclo[2.2.2]octanyl, bicyclo[3.2.1]octanyl, bicyclo [4.1.1]octanyl, bicyclo[3.3.1]nonanyl, bicyclo[4.2.1] nonanyl, bicyclo[3.3.2]decanyl, bicyclo[4.2.2]decanyl, bicyclo[4.3.1]decanyl, bicyclo[3.3.3]undecanyl, bicyclo [4.3.2]undecanyl, bicyclo[4.3.3]dodecanyl, and the like. Examples of spiro cycloalkyl groups include spiro[3.3] heptanyl, spiro[2.4]heptanyl, spiro[3.4]octanyl, spiro[2.5] octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkanediyl" refers to divalent cycloalkyl groups, where cycloalkyl is defined above, and generally having a specified number of carbon atoms (e.g., $C_{3-4}$ cycloalkanediyl refers to a cycloalkanediyl group having 3 to 4 (i.e., 3 or 4) carbon atoms, $C_{3-6}$ cycloalkanediyl refers to a cycloalkanediyl group having 3 to 6 carbon atoms, and so on). Examples of cycloalkanediyl groups include cyclopropan-1,1-diyl, cyclopropan-1,2-diyl, cyclobutan-1,1-diyl, cyclobutan-1,2-diyl, and the like.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom, and where indicated, may optionally include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo [2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom, and where indicated, may optionally include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-8}$ heterocyclyl refers to a heterocyclyl group having 2 to 8 carbon atoms and 1 to 4 heteroatoms as ring members). As with bicyclic cycloalkyl groups, bicyclic heterocyclyl groups may include isolated rings, spiro rings, fused rings, and bridged rings in which at least one of the rings includes one or more heteroatoms. The heterocyclyl group may be attached through any ring atom, and where indicated, may optionally include one or more non-hydrogen substituents unless such attachment or substitution would violate valence requirements or result in a chemically unstable compound. Examples of heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothienyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,5,6-tetrahydropyridinyl, 1,6-dihydropyrimidinyl, 1,2,3,4-tetrahydropyrimidinyl, and 1,2-dihydropyrazolo[1,5-d][1,2,4]triazinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-8}$ heterocycle-diyl refers to a heterocycle-diyl group having 2 to 8 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings), and where indicated, may optionally include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thienyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothienyl, benzo[c]thienyl, 1H-indolyl, 3H-indolyl, isoindolyl, 1H-isoindolyl, indolinyl, isoindolinyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-a]pyridinyl, 2,3-dihydro-1H-imidazo[4,5-b]pyridinyl, tetrazolo[1,5-a]pyridinyl, 7H-pyrrolo[2,3-d]pyrimidinyl, pyrazolo[1,5-a]pyrimidinyl, imidazo[1,2-a]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-a]pyrazinyl, imidazo[1,2-b]pyridazinyl, and 4,5,6,7-tetrahydropyrazolo[1,5-a]pyrazinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and Off can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (ZIE) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with 5-$HT_4$R" and similar phrases relate to a disease, disorder or condition in a subject for which activation (agonism) of 5-$HT_4$R may provide a therapeutic or prophylactic benefit.

The following abbreviations may be used in the specification: Ac (acetyl); ACN (acetonitrile); AIBN (azo-bis-isobutyronitrile); API (active pharmaceutical ingredient); aq (aqueous); $B_2pin_2$ (4,4,4',4',5,5,5',5'-octamethyl-2,2'-bi(1,3,2-dioxaborolane)); BINAP (2,2'-bis(diphenylphosphino)-1,1'-binaphthyl); Bn (benzyl); Boc (tert-butoxycarbonyl); Cbz (carbobenzyloxy); CDI (1,1'-carbonyldiimidazole); dba (dibenzylideneacetone); DAST (N,N-diethylaminosulfur trifluoride); DCC (1,3-dicyclohexylcarbodiimide); DCE (1,1-dichloroethane); DCM (dichloromethane); DIAD (diisopropyl azodicarboxylate); DIBAL-H (diisobutylaluminium hydride); DIPEA (N,N-diisopropylethylamine, Hünig's Base); DMA (N,N-dimethylacetamide); DMAP (4-dimethylaminopyridine); DME (1,2-dimethoxyethane); DMF (N,N-dimethylformamide); DMSO (dimethylsulfoxide); dppf (1,1'-bis(diphenylphosphino)ferrocene); DTT (dithiothreitol); ECso (effective concentration at half maximal response); EDA (ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); $Et_3N$ (triethylamine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); HOAc (acetic acid); HOBt (1H-benzo[d][1,2,3]triazol-1-01); $IC_{50}$ (concentration at 50% inhibition); IPA (isopropanol); IPAc (isopropyl acetate); IPE (isopropylether); KOt-Bu (potassium tertiary butoxide); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); n-BuLi (n-butyl lithium); NaOt-Bu (sodium tertiary butoxide); NBS (N-bromosuccinimide); NCS (N-chlorosuccinimide); NIS (N-iodosuccinimide); NMM (N-methylmorpholine); NMP (N-methyl-pyrrolidone); OTf (triflate); $PdCl_2$(dtbpf) (dichloro[1,1'-bis(di-tert-butylphosphino)ferrocene]palladium (II)); PE (petroleum ether); Ph (phenyl); $pEC_{50}$ ($-\log_{10}$ ($EC_{50}$), where $EC_{50}$ is given in molar (M) units); $pIC_{50}$ ($-\log_{10}(IC_{50})$, where $IC_{50}$ is given in molar (M) units); Pr (propyl); c-Pr (cyclopropyl), i-Pr (isopropyl); PTFE (polytetrafluoroethylene); Py (pyridine); Rac (racemic); RT (room temperature, approximately 20° C. to 25° C.); SEM (2-(trimethylsilyl)ethoxymethyl); SEM-Cl ((2-chloromethoxyethyl)trimethylsilane); SFC (supercritical fluid chromatography); T3P (2,4,6-tripropyl-1,3,5,2,4,6-trioxatriphosphinane 2,4,6-trioxide); TBAF (tetrabutylammonium fluoride); TBS (tert-butyldimethylsilyl); TBSCl (tert-butylchlorodimethylsilane); TCEP (tris(2-carboxyethyl)phosphine); TEMPO ((2,2,6,6-tetramethylpiperidin-1-yl)oxyl); TFA (trifluoroacetic acid); TFAA (2,2,2-trifluoroacetic anhydride); THF (tetrahydrofuran); TLC (thin layer chromatography); TMEDA (tetramethylethylenediamine); TMS (trimethylsilyl); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating diseases, disorders or conditions associated with $5\text{-}HT_4R$, including gastrointestinal motility disorders.

The compounds of Formula 1 include those in which (1):

1

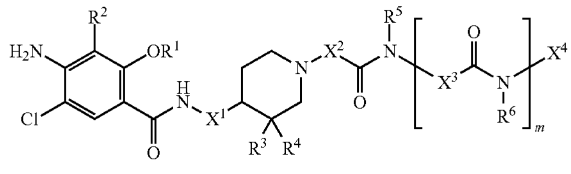

m is an integer selected from 0 and 1;

$R^1$ is methyl and $R^2$ is hydrogen, or $R^1$ and $R^2$ together form an ethane-1,2-diyl which bridges the oxygen and carbon atoms to which $R^1$ and $R^2$ are respectively attached;

$R^3$ and $R^4$ are each independently selected from hydrogen, halo, $C_{1-4}$ alkyl and $C_{1-3}$ alkoxy;

$R^5$ and $R^6$ are each independently selected from hydrogen and $C_{1-4}$ alkyl which is unsubstituted or substituted with an optional substituent selected from hydroxy, phosphono, sulfo and amino, wherein the amino optional substituent is unsubstituted or substituted with 1 or 2 optional substituents independently selected from $C_{1-3}$ alkyl;

$X^1$ is selected from a bond and methane-1,1-diyl;

$X^2$ is selected from (a) pentane-1,5-diyl which is unsubstituted or substituted with 1 to 5 optional substituents independently selected from halo and $C_{1-3}$ alkyl, wherein one of the carbon atoms of the pentane-1,5-diyl substituent may be optionally replaced with one oxygen atom, provided the oxygen atom is directly bonded to two carbon atoms within the pentane-1,5-diyl substituent; and (b) a moiety represented by the formula

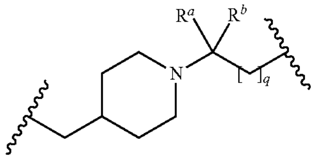, wherein $R^a$ and $R^b$ are each hydrogen or together represent oxo; and q is an integer selected from 1, 2, 3, 4, 5, 6, 7, 8, 9 and 10;

$X^3$ is selected from (a) $C_{1-11}$ alkanediyl, wherein 0 to 3 carbon atoms of the alkanediyl substituent may be optionally replaced, one-to-one, with oxygen atoms, provided each replacement oxygen atom is directly bonded to two carbon atoms within the alkanediyl substituent and any two replacement oxygen atoms are separated by at least one carbon atom; and (b) a moiety represented by the formula,

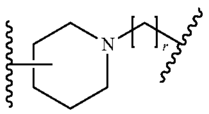, wherein r is an integer selected from 1, 2, 3, 4, 5, 6 and 7; and $X^4$ is selected from (a) $C_{3-6}$ alkyl which is substituted with 3 to 6 hydroxy substituents;

(b) $C_{1-3}$ alkyl which is substituted with phosphono or sulfo substituents; and (c) cyclohexyl which is substituted with 3 to 6 substituents independently selected from hydroxy and hydroxymethyl;

wherein the bracketed moieties in Formula 1 and in the formulas for $X^2$ and $X^3$ are present m, q or r times, respectively, and each ∿ represents a point of attachment in the formulas for $X^2$ and $X^3$.

In addition to embodiment (1) in the preceding paragraph, the compounds of Formula 1 include those in which:

(2) $R^1$ is methyl and $R^2$ is hydrogen.

In addition to embodiment (2) in the preceding paragraph, the compounds of Formula 1 include those in which:

(3) $X^1$ is a bond.

In addition to embodiment (1) above, the compounds of Formula 1 include those in which:

In addition to embodiment (1) above, the compounds of Formula 1 include those in which:

(4) $R^1$ and $R^2$ together form an ethane-1,2-diyl which bridges the oxygen and carbon atoms to which $R^1$ and $R^2$ are respectively attached.

In addition to embodiment (4) in the preceding paragraph, the compounds of Formula 1 include those in which:

(5) $X^1$ is a bond; or (6) $X^1$ is methane-1,1-diyl.

In addition to embodiments (1) to (6) in the preceding paragraphs, the compounds of Formula 1 include those in which:

(7) $R^3$ and $R^4$ are each independently selected from hydrogen, $C_{1-4}$ alkyl and $C_{1-3}$ alkoxy;

(8) $R^3$ and $R^4$ are each independently selected from hydrogen and $C_{1-3}$ alkoxy; or (9) $R^3$ and $R^4$ are each independently selected from hydrogen and methoxy.

In addition to embodiments (7) to (9) in the preceding paragraphs, the compounds of Formula 1 include those in which:

(10) $R^3$ and $R^4$ are different.

In addition to embodiments (1) to (6) above, the compounds of Formula 1 include those in which:

(11) $R^3$ and $R^4$ are each hydrogen.

In addition to embodiments (1) to (11) in the preceding paragraphs, the compounds of Formula 1 include those in which:

(12) $X_2$ is pentane-1,5-diyl which is unsubstituted or substituted with 1 to 5 optional substituents independently selected from halo and $C_{1-3}$ alkyl, wherein one of the carbon atoms of the pentane-1,5-diyl substituent may be optionally replaced with one oxygen atom, provided the oxygen atom is directly bonded to two carbon atoms within the pentane-1,5-diyl substituent;

(13) $X_2$ is pentane-1,5-diyl which is unsubstituted or substituted with 1 to 5 optional substituents independently selected from $C_{1-3}$ alkyl, wherein one of the carbon atoms of the pentane-1,5-diyl substituent may be optionally replaced with one oxygen atom, provided the oxygen atom is directly bonded to two carbon atoms within the pentane-1,5-diyl substituent;

(14) $X_2$ is pentane-1,5-diyl which is unsubstituted or substituted with 1 to 5 optional substituents selected from methyl and ethyl, wherein one of the carbon atoms of the pentane-1,5-diyl substituent may be optionally replaced with one oxygen atom, provided the oxygen atom is directly bonded to two carbon atoms within the pentane-1,5-diyl substituent; or

(15) $X_2$ is pentane-1,5-diyl which is unsubstituted or substituted with 1 to 5 optional substituents selected from methyl, wherein one of the carbon atoms of the pentane-1,5-diyl substituent may be optionally replaced with one oxygen atom, provided the oxygen atom is directly bonded to two carbon atoms within the pentane-1,5-diyl substituent.

In addition to embodiments (12) to (15) in the preceding paragraphs, the compounds of Formula 1 include those in which:

(16) $X_2$ is pentane-1,5-diyl which is unsubstituted or substituted with 1 to 3 optional substituents;

(17) $X_2$ is pentane-1,5-diyl which is unsubstituted or substituted with 1 or 2 optional substituents;

(18) $X_2$ is pentane-1,5-diyl which is unsubstituted or substituted with 1 optional substituent; or In addition to embodiment (12) above, the compounds of Formula 1 include those in which:

(19) $X_2$ is pentane-1,5-diyl which is unsubstituted.

In addition to embodiments (12) to (19) in the preceding paragraphs, the compounds of Formula 1 include those in which:

(20) $X_2$ is $-(CH_2)_2O(CH_2)_2-$; or

(21) $X_2$ is pentane-1,5-diyl in which none of the carbon atoms of the pentane-1,5-diyl substituent is optionally replaced with an oxygen atom.

In addition to embodiments (1) to (21) above, the compounds of Formula 1 include those in which:

(22) $X^2$ is a moiety represented by the formula

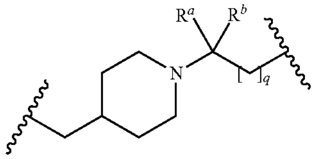, wherein $R^a$ and $R^b$ are each hydrogen or together represent oxo; and q is an integer selected from 1, 2, 3, 4, 5, 6, 7, 8, 9 and 10.

In addition to embodiment (22) in the preceding paragraph, the compounds of Formula 1 include those in which:

(23) $R^a$ and $R^b$ are each hydrogen; or

(24) $R^a$ and $R^b$ together represent oxo.

In addition to embodiments (22) to (24) in the preceding paragraphs, the compounds of Formula 1 include those in which:

(25) q is an integer selected from 3, 4, 5, 6, 7, 8, 9 and 10.

In addition to embodiments (1) to (24) in the preceding paragraphs, the compounds of Formula 1 include those in which:

(26) $R^5$ is selected from hydrogen and $C_{1-4}$ alkyl which is unsubstituted;

(27) $R^5$ is selected from hydrogen, methyl, ethyl and isopropyl;

(28) $R^5$ is selected from hydrogen and methyl; or

(29) $R^5$ is hydrogen.

In addition to embodiments (1) to (29) in the preceding paragraphs, the compounds of Formula 1 include those in which:

(30) $X^3$ is $C_{1-11}$ alkanediyl, wherein 0 to 3 carbon atoms of the alkanediyl substituent may be optionally replaced, one-to-one, with oxygen atoms, provided each replacement oxygen atom is directly bonded to two carbon atoms within the alkanediyl substituent and any two replacement oxygen atoms are separated by at least one carbon atom;

(31) $X^3$ is $C_{1-11}$ alkanediyl, wherein 0 to 3 carbon atoms of the alkanediyl substituent may be optionally replaced, one-to-one, with oxygen atoms, provided each replacement oxygen atom is directly bonded to two carbon atoms within the alkanediyl substituent and any two replacement oxygen atoms are separated by at least two carbon atoms;

(32) $X^3$ is $C_{1-11}$ alkanediyl, wherein 0 to 3 carbon atoms of the alkanediyl substituent may be optionally replaced, one-to-one, with oxygen atoms, provided each replacement oxygen atom is directly bonded to two carbon atoms within the alkanediyl substituent, any two replacement oxygen atoms are separated by at least two carbon atoms, and none of the oxygen atoms is directly bonded to a terminal carbon atom of the alkanediyl substituent;

(33) $X^3$ is $—(CH_2)_2O(CH_2)_2O(CH_2)_2—$;

(34) $X^3$ is $—(CH_2)_2O(CH_2)_2O(CH_2)_2O(CH_2)_2—$;

(35) $X^3$ is $C_{1-11}$ alkanediyl in which none of the carbon atoms of the alkanediyl substituent is replaced with oxygen atoms;

(36) $X^3$ is $C_{1-7}$ alkanediyl in which none of the carbon atoms of the alkanediyl substituent is replaced with oxygen atoms;

(37) $X^3$ is a moiety represented by the formula,

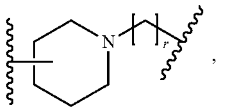

wherein r is an integer selected from 1, 2, 3, 4, 5, 6 and 7;

(38) $X^3$ is a moiety represented by the formula,

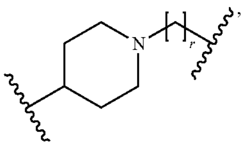

wherein r is an integer selected from 1, 2, 3, 4, 5, 6 and 7; or

(39) $X^3$ is a moiety represented by the formula,

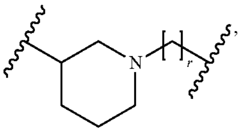

wherein r is an integer selected from 1, 2, 3, 4, 5, 6 and 7.

In addition to embodiments (37) to (39) in the preceding paragraph, the compounds of Formula 1 include those in which:

(40) r is an integer selected from 3, 4, 5, 6 and 7.

In addition to embodiments (1) to (40) in the preceding paragraphs, the compounds of Formula 1 include those in which:

(41) $R^6$ is selected from hydrogen and $C_{1-3}$ alkyl which is unsubstituted or substituted with an optional substituent selected from hydroxy, phosphono, sulfo and dimethylamino;

(42) $R^6$ is selected from hydrogen, methyl, hydroxyethyl, phosphonoethyl, sulfoethyl and dimethylaminopropyl; or

(43) $R^6$ is hydrogen.

In addition to embodiments (1) to (43) in the preceding paragraphs, the compounds of Formula 1 include those in which:

(44) $X^4$ is $C_{3-6}$ alkyl which is substituted with 3 to 6 hydroxy substituents;

(45) $X^4$ is hexyl which is substituted with 3 to 6 hydroxy substituents;

(46) $X^4$ is 2,3,4,5,6-pentahydroxyhexyl;

(47) $X^4$ is (2S,3R,4R,5R)-2,3,4,5,6-pentahydroxyhexyl or a stereoisomer thereof;

(48) $X^4$ is $C_{1-3}$ alkyl which is substituted with phosphono or sulfo substituents;

(49) $X^4$ is phosphonoethyl;

(50) $X^4$ is sulfoethyl;

(51) $X^4$ is cyclohexyl which is substituted with 3 to 6 substituents independently selected from hydroxy and hydroxymethyl;

(52) $X^4$ is 2,3,4,5-tetrahydroxy-5-(hydroxymethyl)cyclohexyl; or

(53) $X^4$ is (2S,3R,4S,5S)-2,3,4,5-tetrahydroxy-5-(hydroxymethyl)cyclohexyl or a stereoisomer thereof.

Compounds of Formula 1 include embodiments (1) through (53) described in the preceding paragraphs and all compounds specifically named in the examples, and may exist as salts, complexes, solvates, hydrates, and liquid crystals. Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J.*

*Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug), and at least one other component, are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., $-COO^-Na^+$, $-COO^-K^+$, $-SO_3^-Na^+$) or polar non-ionic moiety (such as $-N^-N^+(CH_3)_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high-pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^{2}H$ and $^{3}H$; isotopes of carbon, such as $^{11}C$, $^{13}C$ and $^{14}C$; isotopes of nitrogen, such as $^{13}N$ and $^{15}N$; isotopes of oxygen, such as $^{15}O$, $^{17}O$ and $^{18}O$; isotopes of sulfur, such as $^{35}S$; isotopes of fluorine, such as $^{18}F$; isotopes of chlorine, such as $^{36}Cl$, and isotopes of iodine, such as $^{123}I$ and $^{125}I$. Use of isotopic variations (e.g., deuterium, $^{2}H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^{3}H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in several treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure and claims to a stoichiometric range, a temperature range, a pH range, etc., whether expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane, cyclohexane, methylcyclohexane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropylether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1, -dioxide); and phosphorus-containing solvents (e.g., hexamethylphosphoric triamide).

In the schemes, below, substituent identifiers (m, $R^1$, $R^2$, $R^3$, $R^4$, $R^5$, $R^6$, $X^1$, $X^2$, $X^3$ and $X^4$) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups (unless explicitly shown). For example, a starting material or intermediate in the schemes may include $X^2$ substituent having a potentially reactive hydroxy group. In such cases, $X^1$ may include the moiety with or without, say, a TBS or Ac group attached to the oxygen atom.

Schemes A and B show general methods for preparing compounds of Formula 1. In accordance with the method depicted in Scheme A, a benzoic acid derivative (A1) is reacted with an amino piperidine derivative (A2) to give an amine-protected piperidine intermediate (A3). In Scheme A (and in Scheme B), PG represents a suitable amine protecting group, such as Boc, Cbz, Bn, etc. The reaction may be carried out using standard amide coupling agents, such as HATU, DCC, EDC hydrochloride, T3P or 2-chloro-1-methylpyridin-1-ium iodide, in the presence of a non-nucleophilic base (e.g., $Et_3N$, DIPEA) and one or more compatible solvents (e.g. ACN, DCM, DMA, DMF, NMP, pyridine, THF), and at temperatures which range from about room temperature to about 80° C. HOBt may be used to facilitate the reaction. The piperidine intermediate (A3) is deprotected via treatment with concentrated strong acid, such as 4 M HCl in dioxane, at room temperature or below (for Boc removal) or via reaction with $H_2$ in the presence of a catalyst (e.g., Pd/C) and suitable solvent (e.g., MeOH) at temperatures which range from about room temperature to about 50° C. (for removal of Cbz or Bn). The resulting deprotected piperidine intermediate (A4) is reacted with an alkyl bromide (A5, $R^7$=methyl or ethyl) in the presence of an inorganic base (e.g. $K_2CO_3$), catalyst (NaI or KI) and polar aprotic solvent (e.g., DMF, ACN) at elevated temperature (up to about 80° C.) to give an ester intermediate (A6). The ester (A6) is subsequently hydrolyzed via treatment with aqueous base (NaOH, LiOH) in a suitable solvent (e.g., MeOH, THF) at temperatures which range from about 10° C. to about 80° C. to give a carboxylic acid intermediate (A7).

Scheme A

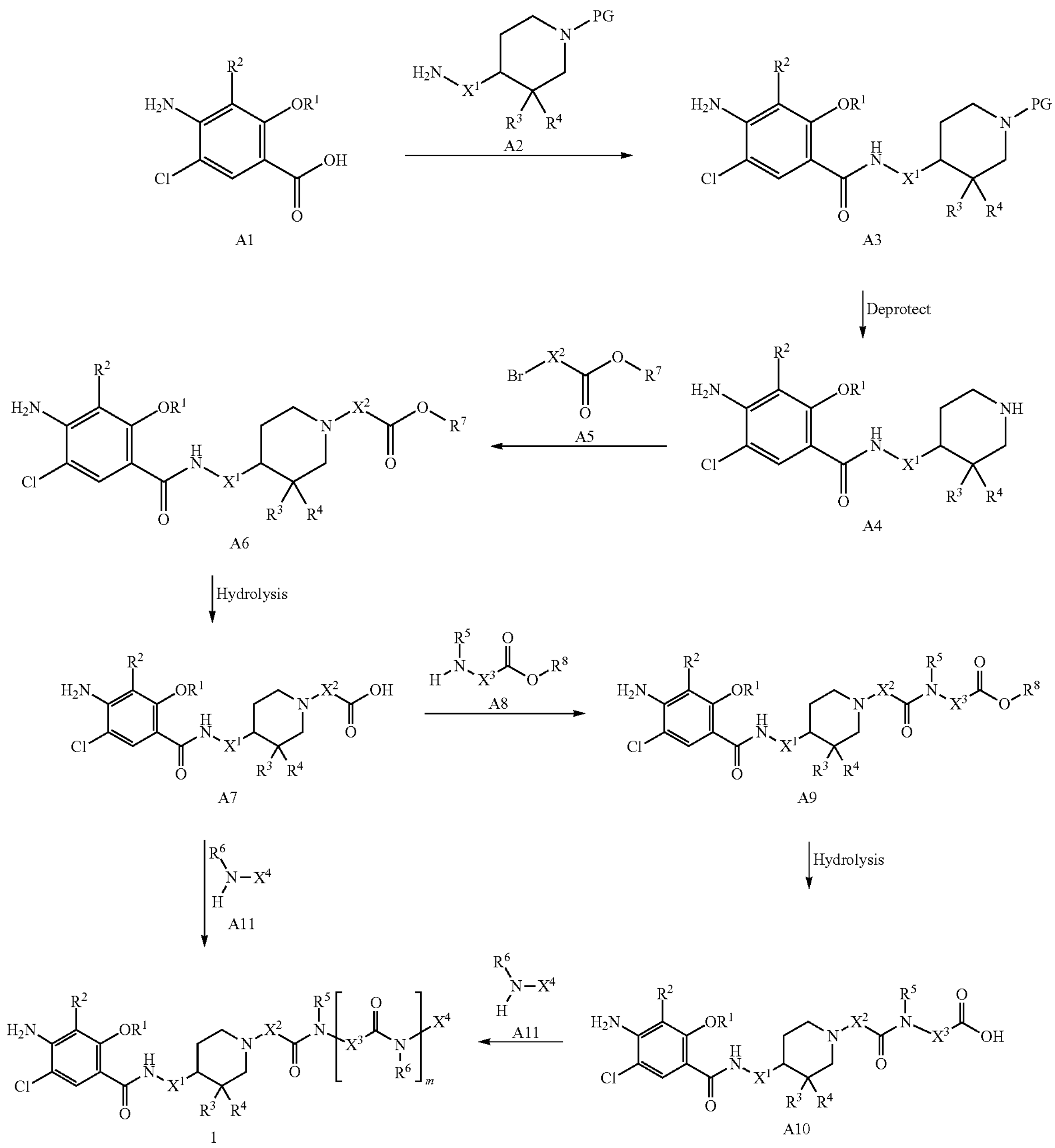

For compounds of Formula 1 in which m is 1, the carboxylic acid intermediate (A7) is reacted with an amine (A8, $R^8$=methyl or ethyl) to give an ester intermediate (A9). Subsequent base hydrolysis of the ester (A9) gives a penultimate carboxylic acid intermediate (A10) which is reacted with an amine (A11) to afford the compound of Formula 1 (m=1). Alternatively, the carboxylic acid intermediate (A7) is reacted with the amine (A11) to give the compound of Formula 1 in which m is 0. The steps used to prepare the ester intermediate (A9) and the compound of Formula 1 are carried out using amide coupling reagents and conditions described above.

The methods depicted in the schemes may be varied as desired. For example, protecting groups may be added or removed, and intermediates or products may be further elaborated via, for example, alkylation, acylation, halogenation, hydrolysis, oxidation, reduction, amidation, sulfonation, alkynation, transition metal catalyzed cross-coupling reactions, and the like to give the desired final product. Furthermore, any intermediate or final product which comprises mixture of stereoisomers may be optionally purified by chiral column chromatography (e.g., supercritical fluid chromatography) or by derivatization with optically-pure reagents as described above to give a desired stereoisomer.

Scheme B

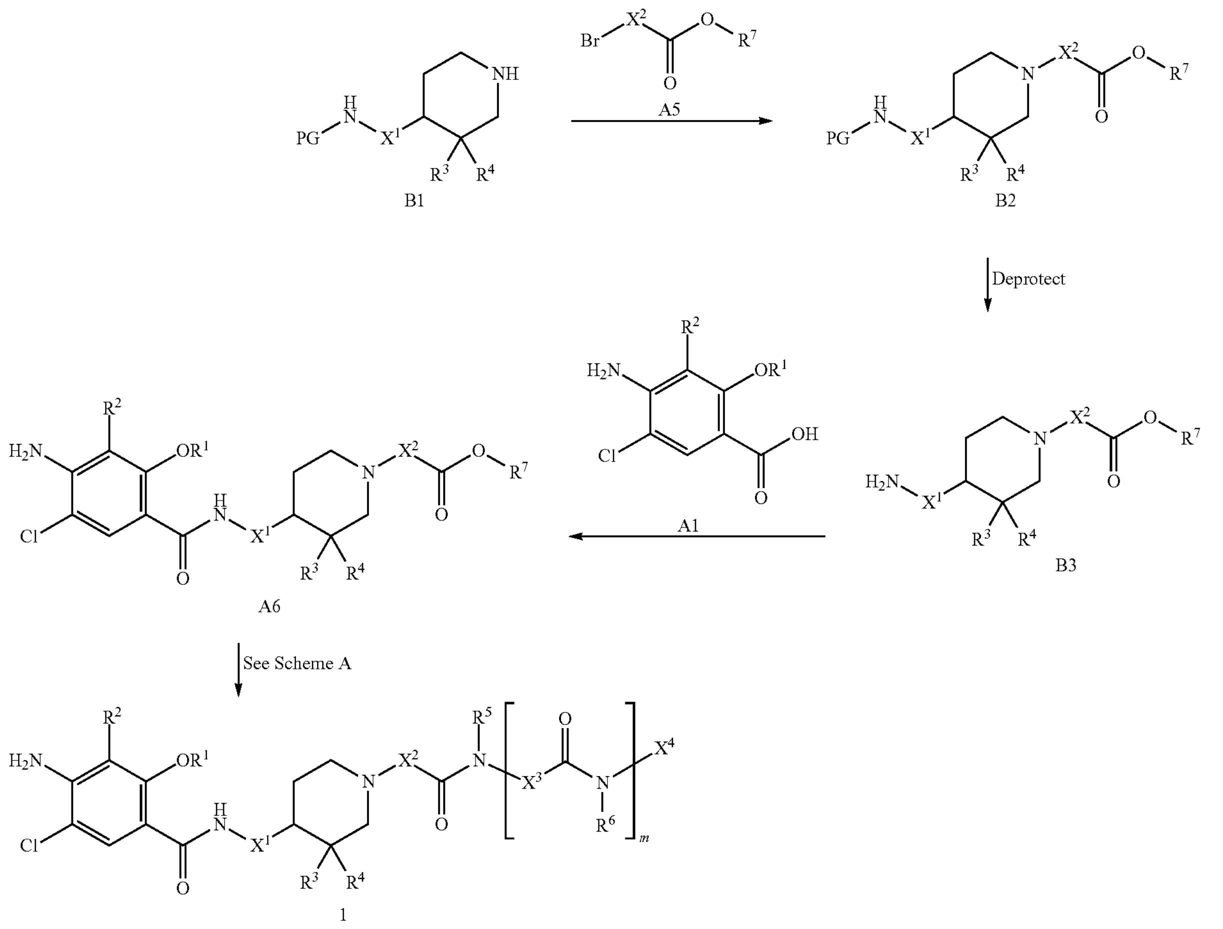

As can be seen in Scheme B, the order of the steps may be varied. In accordance with the method depicted in Scheme B, a piperidine derivative (B1) is reacted with an alkyl bromide (A5) in the presence of an inorganic base (e.g. $K_2CO_3$), catalyst (NaI or KI) and polar aprotic solvent (e.g., DMF, ACN) at elevated temperature (up to about 80° C.) to give an amine-protected ester intermediate (B2). Removal of the amine protecting group gives a deprotected ester intermediate (B3) which is subsequently reacted with a benzoic acid derivative (A1) to give an ester intermediate (A6). The amide coupling is carried out using reagents and conditions described above. The ester intermediate (A6) is then converted to the compound of Formula 1 using the method described in Scheme A.

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more of these compounds are administered as a pharmaceutical composition (a formulation) in association with one or more pharmaceutically acceptable excipients. The choice of excipients depends on the mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets, Vol.* 1-3 (2d ed., 1990); and D. K. Parikh & C. K. Parikh, *Handbook of Pharmaceutical Granulation Technology, Vol.* 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may be carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders or conditions for which activation of $5\text{-HT}_4\text{R}$ is indicated. Such diseases, disorders or conditions generally relate to any unhealthy or abnormal state in a subject for which the inhibition of $5\text{-HT}_4\text{R}$ provides a therapeutic benefit. More particularly, such diseases, disorders or conditions gastrointestinal motility diseases, disorders or conditions, or diseases, disorders or conditions that involve damage to the GI epithelium. Such diseases, disorders or conditions include chronic idiopathic constipation, slow transit constipation, opioid-induced constipation, irritable bowel syndrome, Crohn's Disease, ulcerative colitis, enteral feeding intolerance, postoperative ileus, postoperative gastrointestinal dysfunction, diabetic gastroparesis, idiopathic gastroparesis, functional abdominal pain, chronic intestinal pseudo-obstruction, Hirschsprung Disease, Celiac Disease and short bowel syndrome.

The claimed and disclosed compounds may be combined with one or more other pharmacologically active compounds or therapies for the treatment of one or more diseases, disorders or conditions for which $5\text{-HT}_4\text{R}$ is indicated. Potentially useful combinations include a compound of Formula 1 in combination with anti-inflammatory agents, including steroids; prokinetic agents, antidiarrheals, prosecretory agents, antibiotics, tricyclic antidepressants, selective serotonin reuptake inhibitors (SSRIs), gapapentinoids. The compounds of Formula 1 may also be combined with approved therapies for ulcerative colitis or Crohn's Disease. Such combinations may offer significant therapeutic advantages, including fewer side effects, improved ability to treat underserved patient populations, or synergistic activity.

Biological Activity

One may determine the activity of the compounds of Formula 1 using a variety of methods, including in vitro and in vivo methods. The ability of the example compounds to activate the $5\text{-HT}_4$(b) receptor may be determined using the following assay.

Chinese hamster ovary (CHO-K1) cells overexpressing the full-length human $5\text{-HT}_4$(b) receptor with an N-terminal FLAG tag (Multispan Inc, Hayward, CA) are cultured per the manufacturer's protocol in 1:1 DMEM/F12 (Thermo Fisher, Waltham, MA) with 10% fetal bovine serum (GE Healthcare, Pittsburgh, PA) and 10 μg/mL puromycin (Thermo Fisher, Waltham, MA), and stored in frozen aliquots to be used as assay ready cells. On the day of the assay, cells are removed from frozen storage, washed two times in 1× Kreb's Ringer Buffer (Zenbio, Research Triangle Park, NC), and re-suspended to a concentration of $4\times10^6$ cells/mL in 1× Kreb's Ringer Buffer. Test compound (50 nL) in 100% DMSO is acoustically dispensed in low volume, white, 384-well polypropylene plates (Corning, Tewksbury, MA), followed by the addition of $4\times10^4$ cells per well in a total volume of 10 μL. Cells are incubated with test compound for 30 minutes at room temperature in the dark, and cAMP accumulation is measured using the Cisbio HiRange cAMP assay kit (Bedford, MA) per the manufacturer's protocol. Anti-cAMP antibody and d2-cAMP tracer reagents diluted in lysis/detection buffer are incubated in the dark for 1 hour, and results are measured on a Pherastar plate reader (BMG Labtech, Ortenberg, Germany). Data are normalized using 1 μM 5-HT (Sigma Aldrich, St. Louis, MO) as 100% activity, and DMSO alone as 0% activity.

EXAMPLES

The following examples are intended to be illustrative and non-limiting and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and THF-$d_8$ (deuterotetrahydrofuran). The mass spectra (m/z for $[M+H]^+$) were recorded using either electrospray ionization (ESI-MS) or atmospheric pressure chemical ionization (APCI-MS) mass spectrometry.

Where indicated, products of certain preparations and examples are purified by mass-triggered HPLC, flash chromatography, preparative TLC or SFC. Reverse phase chromatography is typically carried out on a column (e.g., Gemini™ 5 μm C18 110 Å, Axia™ 30×75 mm, 5 μm) under acidic conditions ("acid mode") eluting with ACN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM $NH_4HCO_3$. Preparative TLC is typically carried out on silica gel 60 $F_{254}$ plates. The preparations and examples may employ SFC to separate enantiomers. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

PREPARATION 1: tert-butyl (3S,4R)-4-(4-amino-5-chloro-methoxybenzamido)-3-methoxypiperidine-1-carboxylate

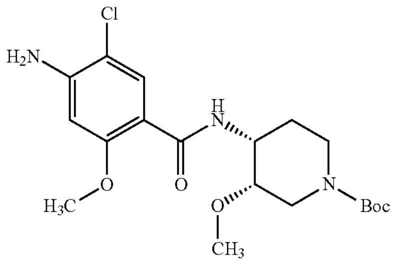 [SMILES: COc1cc(N)c(Cl)cc1C(=O)N[C@@H]1CCN(C(=O)OC(C)(C)C)C[C@@H]1OC]

To a solution of 4-amino-5-chloro-2-methoxybenzoic acid (5 g, 24.80 mmol) in DMF (100 mL) was added HATU (18.86 g, 49.60 mmol) and DIPEA (9.62 g, 74.40 mmol, 12.96 mL). The reaction mixture was stirred at 20° C. for 0.5 hours. Next, tert-butyl (3S,4R)-4-amino-3-methoxypiperidine-1-carboxylate (5.83 g, 25.30 mmol) was added at 20° C. The reaction mixture was stirred at 20° C. for 2 hours and then was concentrated to remove most of the DMF, diluted with $H_2O$ (100 mL) and extracted with EtOAc (200 mL×2). The combined organic layers were washed with $H_2O$ (500 mL×3) followed by brine (500 mL), dried over $Na_2SO_4$, filtered and concentrated under reduced pressure to give the title compound as a yellow solid (11.4 g, crude). ESI-MS m/z $[M+H]^+$ 414.3.

PREPARATION 2: 4-amino-5-chloro-2-methoxy-N-((3S,4R)-3-methoxypiperidin-4-yl)benzamide

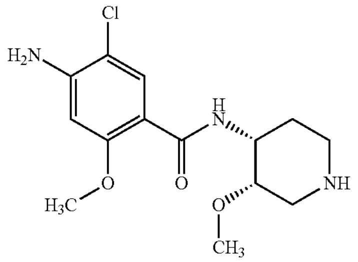 [SMILES: COc1cc(N)c(Cl)cc1C(=O)N[C@@H]1CCNC[C@@H]1OC]

To a solution of tert-butyl (3S,4R)-4-(4-amino-5-chloro-methoxybenzamido)-3-methoxypiperidine-1-carboxylate (11.4 g, 25.62 mmol) in DCM (20 mL) was added HCl in dioxane (4 M, 120 mL) at 0° C. The reaction mixture was stirred at 15° C. for 0.5 hours and then was concentrated to give the title compound as a yellow solid (9.5 g, crude). ESI-MS m/z $[M+H]^+$ 314.0.

PREPARATION 3: methyl 6-((3S,4R)-4-(4-amino-5-chloro-2-methoxybenzamido)-3-methoxypiperidin-1-yl)hexanoate

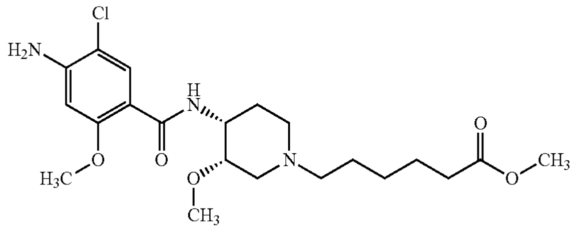 [SMILES: COC(=O)CCCCCN1CC[C@@H](NC(=O)c2cc(Cl)c(N)cc2OC)[C@@H](OC)C1]

To a solution of 4-amino-5-chloro-2-methoxy-N-((3S,4R)-3-methoxypiperidin-4-yl)benzamide (5 g, 14.28 mmol) in DMF (50 mL) was added $K_2CO_3$ (3.95 g, 28.55 mmol), methyl 6-bromohexanoate (4.48 g, 21.41 mmol) and NaI (214 mg, 1.43 mmol) at 15° C. The reaction mixture was heated to 80° C. and stirred at 80° C. for 2 hours and then was diluted with $H_2O$ (100 mL) and extracted with EtOAc (100 mL×3). The combined organic layers were washed with $H_2O$ (300 mL×3) followed by brine (300 mL×2), dried over $Na_2SO_4$, filtered and concentrated under reduced pressure. The residue was purified by column chromatography ($SiO_2$), using a gradient of petroleum ether/EtOAc (30:1 to 10:1), and the product was confirmed by TLC (petroleum ether/EtOAc=10:1, $R_f$=0.06). The title compound was obtained as a yellow oil (5.8 g). ESI-MS m/z $[M+H]^+$ 442.3.

PREPARATION 4: 6-((3S,4R)-4-(4-amino-5-chloro-2-methoxybenzamido)-3-methoxypiperidin-1-yl) hexanoic acid

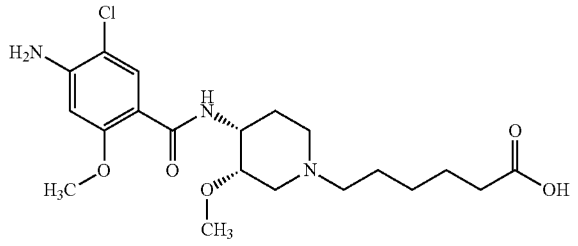 [SMILES: COc1cc(N)c(Cl)cc1C(=O)N[C@@H]1CCN(CCCCCC(=O)O)C[C@@H]1OC]

To a solution of methyl 6-((3S,4R)-4-(4-amino-5-chloro-2-methoxybenzamido)-3-methoxypiperidin-1-yl)hexanoate (5.8 g, 13.12 mmol) in MeOH (40 mL) was added a solution of NaOH (1.57 g, 39.37 mmol) in $H_2O$ (20 mL) at 0° C. The reaction mixture was heated to 40° C. for 0.5 hours. TLC (DCM/MeOH=10:1) indicated the starting material was consumed and one new major spot ($R_f$=0) was formed. The reaction mixture was adjusted to pH 7 with 1 M HCl and then concentrated under reduced pressure to give the title compound as a white solid (7.5 g, crude). ESI-MS m/z $[M+H]^+$ 428.2.

PREPARATION 5: ethyl 3-hydroxy-4,4-dimethoxypiperidine-1-carboxylate

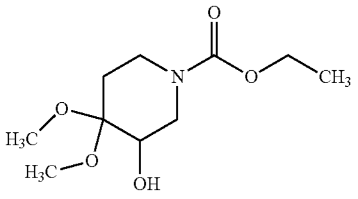 [SMILES: CCOC(=O)N1CCC(OC)(OC)C(O)C1]

To a solution of KOH (245.8 g, 4.38 mol) in MeOH (1050 mL) was added ethyl 4-oxopiperidine-1-carboxylate (250 g, 1.46 mol, 219.3 mL) at 0 to 10° C. The mixture was stirred at 0° C. for 0.5 hours. Next, 12 (407.7 g, 1.61 mol, 323.58 mL) was added at 0° C. under $N_2$ atmosphere and the mixture was stirred at 25° C. for 12 hours. TLC (petroleum ether/EtOAc=2:1) indicated the starting material ($R_f$=0.40) was consumed and a major spot ($R_f$=0.20) was formed. The residue was dissolved in $H_2O$ (1.5 L) and extracted with EtOAc (1.5 L x 4). The combined organic layers were dried over $Na_2SO_4$, filtered and concentrated under vacuum to give the title compound as a yellow oil (205 g, crude).

PREPARATION 6: ethyl 3,4,4-trimethoxypiperidine-1-carboxylate

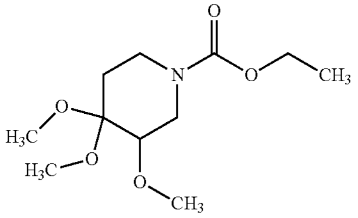 [SMILES: CCOC(=O)N1CCC(OC)(OC)C(OC)C1]

To a solution of ethyl 3-hydroxy-4,4-dimethoxypiperidine-1-carboxylate (205 g, 879 mmol) in THF (1.25 L) was added NaH (70.3 g, 1.76 mol, 60% purity) at 0° C. under $N_2$. The mixture was stirred at 0° C. for 1 hour. Next, MeI (374.2 g, 2.64 mol, 164.13 mL) was added dropwise at 0° C., and the mixture was stirred at 25° C. for 2 hours. TLC (petroleum ether/EtOAc=2:1) indicated the starting material ($R_f$=0.20) was consumed and a major spot ($R_f$=0.50) was formed. The mixture was poured into saturated aq $NH_4Cl$ (4 L) and extracted with EtOAc (1 L×3). The combined organic layers were washed with brine (800 mL), dried over $Na_2SO_4$, filtered and concentrated. The resulting residue was purified by silica gel column chromatography, using a gradient of petroleum ether/EtOAc (10:1 to 3:1, $R_f$=0.50) to give the title compound as a yellow oil (190 g, crude). ESI-MS m/z $[M+H]^+$ 248.1.

PREPARATION 7: ethyl 3-methoxy-4-oxopiperidine-1-carboxylate

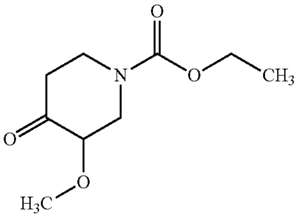

To a solution of ethyl 3,4,4-trimethoxypiperidine-1-carboxylate (190 g, 768 mmol) in THF (760 mL) was added $H_2SO_4$ (0.9 M, 853.71 mL) (0.9 M in water) at 10 to 20° C. The mixture was stirred at 60° C. for 12 hours and then was adjusted to pH 7-8 with saturated aq $NaHCO_3$ and extracted with EtOAc (2.5 L×3). The combined organic layers were dried over $Na_2SO_4$ and concentrated under vacuum. The resulting residue was purified by silica gel column chromatography, using a gradient of petroleum ether/EtOAc (8:1 to 0:1, $R_f$=0.15) to give the title compound as a yellow oil (165 g, crude).

PREPARATION 8: ethyl 4-(dibenzylamino)-3-methoxypiperidine-1-carboxylate

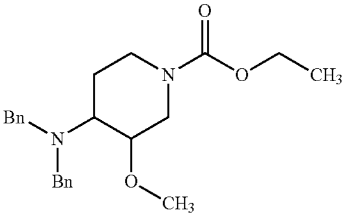 [SMILES: CCOC(=O)N1CCC(N(Cc2ccccc2)Cc2ccccc2)C(OC)C1]

To a solution of ethyl 3-methoxy-4-oxopiperidine-1-carboxylate (165 g, 820 mmol) in DCM (1500 mL) were added dibenzylamine (161.77 g, 820.00 mmol, 157.05 mL) and HOAc (9.85 g, 164 mmol, 9.38 mL) at 0° C. After stirring at 25° C. for 3 hours, $NaBH(OAc)_3$ (260.69 g, 1.23 mol) was added and the mixture was stirred at 25° C. for 12 hours. TLC (petroleum ether/EtOAc=2:1) indicated the starting material ($R_f$=0.15) was consumed and two new spots ($R_f$=0.30, 0.38) were formed. The reaction mixture was adjusted to pH 7-8 with saturated aq $NaHCO_3$ and extracted with EtOAc (500 mL×2). The combined organic layers were concentrated under vacuum and the resulting residue was purified by column chromatography ($SiO_2$) using a gradient of petroleum ether/EtOAc (10:1 to 2:1, $R_f$=0.30, 0.38) to give the title compound as a yellow oil (208.5 g, crude).

PREPARATION 9: N,N-dibenzyl-3-methoxypiperidin-4-amine

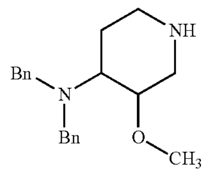

A solution of ethyl 4-(dibenzylamino)-3-methoxypiperidine-1-carboxylate (417 g, 1.09 mol) and NaOH (436.05 g, 10.90 mol) in ethanol (2 L) was stirred at 80° C. for 3 hours. TLC (petroleum ether/EtOAc=2:1) indicated the starting material ($R_f$=0.30, 0.38) was consumed and a major spot ($R_f$=0.00) was formed. The reaction mixture was concentrated under vacuum, and the resulting residue was dissolved in water (1.5 L) and extracted with DCM (1 L). The organic layer was washed with brine (300 mL), dried over $Na_2SO_4$, filtered and concentrated under vacuum. The residue was purified by column chromatography ($SiO_2$), using petroleum ether/EtOAc (1:1), and the product was confirmed by TLC (DCM/MeOH=10:1, $R_f$=0.20). The title compound was obtained as a yellow oil (70.0 g, 20.6% yield, 99.7% purity). ESI-MS m/z $[M+H]^+$ 311.1.

PREPARATION 10: (3S,4R)-N,N-dibenzyl-3-methoxypiperidin-4-amine

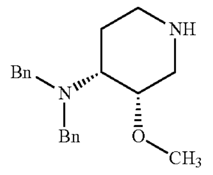

The stereoisomers of N,N-dibenzyl-3-methoxypiperidin-4-amine (70.0 g, 224.82 mmol) were separated by SFC (Thar 350 preparative SFC (SFC-19); column: ChiralPak AD, 300×50 mm ID, 10 μm; mobile phase: $CO_2$ (A) and IPA (B) (0.1% $NH_3H_2O$); gradient: B 30%, flow rate: 240 mL/min; back pressure: 100 bar; column temperature: 38° C.; wavelength: 220 nm; cycle time: ~2 min; injection volume: 4.2 mL). Fractions containing the desired stereoisomer were dried in a rotary evaporator at 40° C. to give the title compound as a yellow solid (19.3 g, 27.6% yield, 100% purity).

PREPARATION 11: ethyl 6-((3S,4R)-4-(dibenzylamino)-3-methoxypiperidin-1-yl)hexanoate

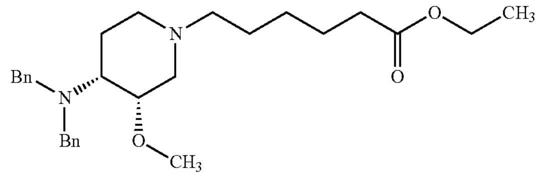 [SMILES: CCOC(=O)CCCCCN1CC[C@@H](N(Cc2ccccc2)Cc2ccccc2)[C@@H](OC)C1]

A solution of (3S,4R)-N,N-dibenzyl-3-methoxypiperidin-4-amine (9.65 g, 31.09 mmol), ethyl 6-bromohexanoate (8.32 g, 37.30 mmol, 6.61 mL), KI (516.03 mg, 3.11 mmol) and $K_2CO_3$ (6.44 g, 46.63 mmol) in DMF (50 mL) was stirred at 60° C. for 3 hours. The reaction mixture was then poured into water (100 mL) and extracted with EtOAc (50 mL×2). The combined organic layers were concentrated under vacuum and purified by column chromatography (Phenomenex Synergi Max-RP, 250×50 mm, 10 μm) using a gradient (15% to 45%) of ACN/water (0.225% formic acid) to give the title compound as a yellow oil (7.25 g, 49.3% yield, 95.7% purity). ESI-MS m/z $[M+H]^+$ 453.3.

PREPARATION 12: ethyl 6-((3S,4R)-4-amino-3-methoxypiperidin-1-yl)hexanoate

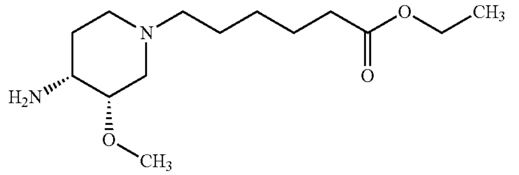 [SMILES: CCOC(=O)CCCCCN1CC[C@@H](N)[C@@H](OC)C1]

A solution of ethyl 6-((3S,4R)-4-(dibenzylamino)-3-methoxypiperidin-1-yl)hexanoate (14.5 g, 30.66 mmol), Pd/C (4.5 g, 10%) in MeOH (150 mL) was stirred at 50° C. under $H_2$ (15 psi) for 2 hours. TLC (DCM/MeOH=10:1) indicated the starting material ($R_f$=0.24) was consumed and a new spot ($R_f$=0.03) was formed. The reaction mixture was filtered, and the filtrate was concentrated under vacuum to give the title compound as a yellow oil (8.20 g, crude).

PREPARATION 13: ethyl 6-((3S,4R)-4-(4-amino-5-chloro-2-methoxybenzamido)-3-methoxypiperidin-1-yl)hexanoate

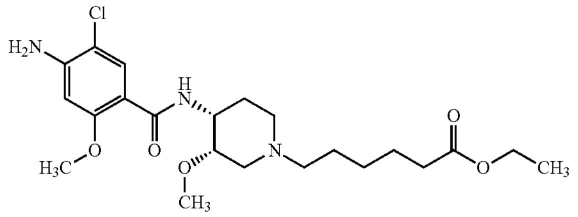 [SMILES: CCOC(=O)CCCCCN1CC[C@@H](NC(=O)c2cc(Cl)c(N)cc2OC)[C@@H](OC)C1]

A solution of ethyl 6-((3S,4R)-4-amino-3-methoxypiperidin-1-yl)hexanoate (7.20 g, 26.43 mmol), 4-amino-5-chloro-2-methoxy-benzoic acid (5.33 g, 26.43 mmol), HATU (10.05 g, 26.43 mmol) and DIPEA (5.12 g, 39.65 mmol, 6.91 mL) in DMF (70 mL) was stirred at 80° C. for 1 hour. TLC (DCM/MeOH=10:1) indicated the starting material ($R_f$=0.03) was consumed and a new spot ($R_f$=0.25) was formed. The reaction mixture was poured into water (150 mL) and extracted with EtOAc (100 mL×2). The combined organic layers were concentrated under vacuum and purified by column chromatography ($SiO_2$) using a gradient of DCM/MeOH (20:1 to 10:1). The resulting brown solid was triturated in petroleum ether/isopropyl ether (3:1, 40 mL) and filtered. The filter cake was dried under vacuum to give the title compound as a yellow solid (9.80 g, 74.4% yield, 91.6% purity). ESI-MS m/z $[M+H]^+$ 456.3.

PREPARATION 14: 6-((3S,4R)-4-(4-amino-5-chloro-2-methoxybenzamido)-3-methoxypiperidin-1-yl)hexanoic acid

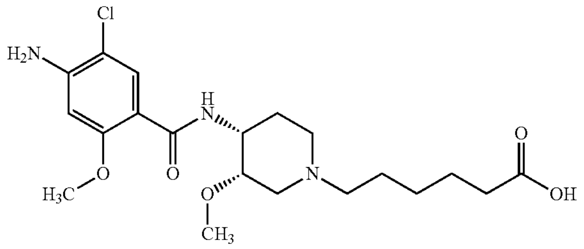 [SMILES: COc1cc(N)c(Cl)cc1C(=O)N[C@@H]1CCN(CCCCCC(=O)O)C[C@@H]1OC]

A solution of ethyl 6-((3S,4R)-4-(4-amino-5-chloro-2-methoxybenzamido)-3-methoxypiperidin-1-yl)hexanoate (10.0 g, 21.93 mmol) and LiOH·$H_2O$ (3.68 g, 87.72 mmol) in THF (60 mL) and MeOH (30 mL) was stirred at 50° C. for 1 hour. TLC (DCM/MeOH=10:1) indicated the starting material ($R_f$=0.25) was consumed and a new spot ($R_f$=0.00) was formed. The reaction mixture was concentrated under vacuum to give a lithium salt of the title compound as a yellow solid (11.8 g, crude).

PREPARATION 15: methyl 6-(4-((tert-butoxycarbonyl)amino)piperidin yl)hexanoate

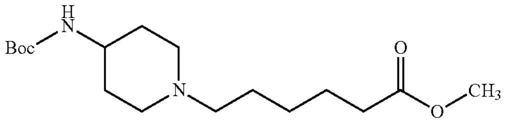 [SMILES: COC(=O)CCCCCN1CCC(NC(=O)OC(C)(C)C)CC1]

A mixture of tert-butyl piperidin-4-ylcarbamate (5 g, 24.97 mmol), methyl 6-bromohexanoate (5 g, 23.91 mmol) and $K_2CO_3$ (5.00 g, 36.18 mmol) in ACN (50 mL) was stirred at 15° C. for 12 hours and then concentrated. The residue was purified by column chromatography ($SiO_2$), using a gradient of petroleum ether/EtOAc (30:1 to 3:1), and the product was confirmed by TLC (petroleum ether/EtOAc=1:1, $R_f$=0.15). The title compound was obtained as a yellow solid (3.7 g, 47%). ESI-MS m/z $[M+H]^+$ 329.2.

PREPARATION 16: methyl 6-(4-aminopiperidin-1-yl)hexanoate

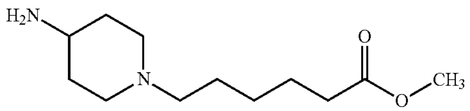 [SMILES: COC(=O)CCCCCN1CCC(N)CC1]

To a solution of methyl 6-(4-((tert-butoxycarbonyl) amino)piperidin-1-yl)hexanoate (3.7 g, 11.27 mmol) in DCM (20 mL) was added 4 M HCl in dioxane (30 mL) at 10° C. The mixture was stirred at 10° C. for 12 hours and then was concentrated to give an HCL salt of the title compound as a yellow solid (3.4 g, crude, 2 HCl). $^1$H NMR (400 MHz, DMSO-$d_6$) δ ppm 11.00-10.78 (m, 1H), 8.60-8.47 (m, 3H), 3.59 (s, 3H), 3.75-3.70 (m, 2H), 3.30-3.17 (m, 1H), 3.05-2.80 (m, 4H), 2.33 (t, J=7.2 Hz, 2H), 2.20-2.18 (m, 2H), 2.03-1.95 (m, 2H), 1.80-1.63 (m, 2H), 1.60-1.44 (m, 2H), 1.37-1.15 (m, 3H).

PREPARATION 17: ethyl 8-(4-((tert-butoxycarbonyl)amino)piperidin-1-yl)octanoate

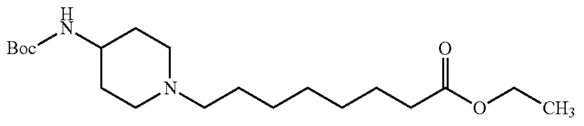 [SMILES: CCOC(=O)CCCCCCCN1CCC(NC(=O)OC(C)(C)C)CC1]

A mixture of tert-butyl piperidin-4-ylcarbamate (5 g, 24.97 mmol), ethyl 8-bromooctanoate (5.02 g, 19.98 mmol), $K_2CO_3$ (5.18 g, 37.46 mmol) and NaI (187.11 mg, 1.25 mmol) in DMF (40 mL) was stirred at 80° C. for 3 hours. TLC (petroleum ether/EtOAc=3:1) indicated the starting material was consumed and one new major spot ($R_f$=0.01) was formed. The reaction mixture was diluted with $H_2O$ (50 mL) and extracted with EtOAc (100 mL×2). The combined organic layers were washed with $H_2O$ (200 mL×3) followed by brine (250 mL), dried over $Na_2SO_4$, filtered and concentrated under reduced pressure. The residue was purified by column chromatography (Si02), using a gradient of petroleum ether/EtOAc (30:1 to 0:1), and the product was confirmed by TLC (petroleum ether/EtOAc=1:1, $R_f$=0.05). The title compound was obtained as a white solid (7.2 g, 78%). 41 NMR (400 MHz, DMSO-$d_6$) δ ppm 6.72 (d, J=8.0 Hz, 1H), 4.07-4.01 (m, 2H), 3.20 (s, 1H), 2.75 (d, J=11.6 Hz, 2H), 2.52 (s, 1H), 2.30-2.10 (m, 4H), 1.83 (t, J=10.4 Hz, 2H), 1.65 (d, 2H), 1.55-1.45 (m, 2H), 1.43-1.33 (m, 10H), 1.33-1.30 (m, 2H), 1.28-1.20 (m, 6H), 1.17 (t, J=7.2 Hz, 3H).

PREPARATION 18: ethyl 8-(4-aminopiperidin-1-yl)octanoate

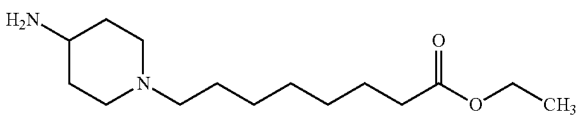 [SMILES: CCOC(=O)CCCCCCCN1CCC(N)CC1]

To a solution of ethyl 8-(4-((tert-butoxycarbonyl)amino) piperidin-1-yl)octanoate (7.2 g, 19.43 mmol) in DCM (40 mL) was added 4 M HCl in dioxane (30 mL) at 0° C. The mixture was warmed to 15° C. and stirred at 15° C. for 12 hours. TLC (EtOAc) indicated the starting material was consumed and one new major spot ($R_f$=0) was formed. The reaction mixture was concentrated to give an HCl salt of the title compound as a white solid (6.3 g, 94%, 2 HCl). $^1$H NMR (400 MHz, DMSO-$d_6$) δ ppm 10.82 (s, 1H), 8.65-8.51 (m, 3H), 4.06-3.90 (m, 2H), 3.50-3.46 (m, 2H), 3.37 (s, 1H), 3.10-2.80 (m, 4H), 2.26 (t, J=7.6 Hz, 2H), 2.24-1.85 (m, 4H), 1.71 (s, 2H), 1.60-1.35 (m, 2H), 1.32-1.14 (m, 9H).

PREPARATION 19: 8-(((benzyloxy)carbonyl)amino)octanoic acid

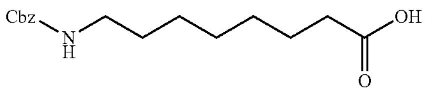 [SMILES: O=C(O)CCCCCCCNC(=O)OCc1ccccc1]

To a stirred suspension of 8-aminooctanoic acid (8.1 g, 50.87 mmol) and $K_2CO_3$ (14.06 g, 101.74 mmol) in THF (240 mL) was slowly added benzyl carbonochloridate (9.55 g, 55.96 mmol, 7.96 mL) at 0° C. The mixture was stirred at 25° C. for 12 hours. TLC (EtOAc) indicated the desired compound ($R_f$=0.25) was detected. The reaction mixture was quenched with $H_2O$ (400 mL) and extracted with MTBE (400 mL). The organic layer was washed with $H_2O$ (250 mL) and the organic layer was discarded. The aqueous phase was adjusted to pH 2 by addition of 1N HCl and then extracted with EtOAc (200 mL×2). The combined organic layers were concentrated under vacuum to give the title compound as a white solid (9.78 g, 49.8% yield, 76.2% purity).

PREPARATION 20: benzyl (8-oxo-8-(((2S,3R,4R,5R)-2,3,4,5,6-pentahydroxyhexyl)amino)octyl)carbamate

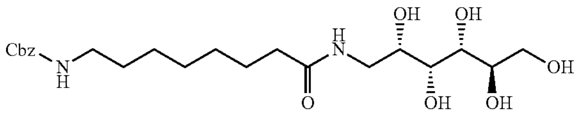 [SMILES: O=C(CCCCCCCNC(=O)OCc1ccccc1)NC[C@H](O)[C@@H](O)[C@H](O)[C@H](O)CO]

A mixture of 8-(((benzyloxy)carbonyl)amino)octanoic acid (10.4 g, 35.45 mmol), (2R,3R,4R,5S)-6-aminohexane-1,2,3,4,5-pentaol (7.07 g, 39.00 mmol), HATU (20.22 g, 53.18 mmol) and DIPEA (6.87 g, 53.18 mmol, 9.26 mL) in DMF (300 mL) was stirred at 15° C. for 3 hours. The reaction mixture was quenched with $H_2O$ (30 mL), concentrated in vacuo and purified by preparative HPLC (basic mode) to give the title compound as a yellow solid (7.3 g, 32% yield, 71.3% purity). ESI-MS m/z $[M+H]^+$ 457.3.

PREPARATION 21: 8-amino-N-((2S,3R,4R,5R)-2,3,4,5,6-pentahydroxyhexyl)octanamide

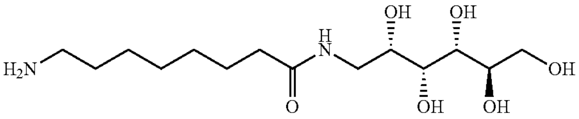 [SMILES: NCCCCCCCC(=O)NC[C@H](O)[C@@H](O)[C@H](O)[C@H](O)CO]

A solution of benzyl (8-oxo-8-(((2S,3R,4R,5R)-2,3,4,5,6-pentahydroxyhexyl)amino)octyl)carbamate (21.95 g, 34.28 mmol), Pd/C (4.5 g, 10%) in MeOH (80 mL) and DMF (8 mL) was stirred at 50° C. under $H_2$ (15 psi) for 2 hours. The reaction mixture was filtered, and the filtrate was concentrated under vacuum to give the title compound as a white solid (15.5 g, crude). ESI-MS m/z $[M+H]^+$ 323.2.

PREPARATION 22: ethyl 8-(4-(6-((3S,4R)-4-(4-amino-5-chloro-2-methoxybenzamido)-3-methoxypiperidin-1-yl)hexanamido)piperidin-1-yl)octanoate

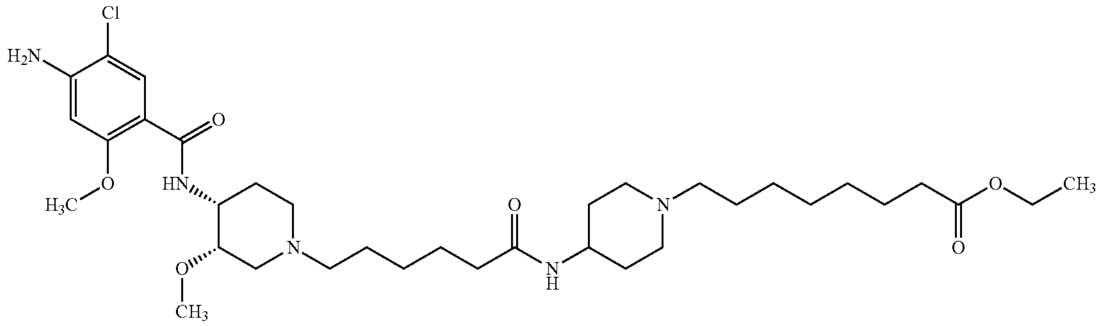 [SMILES: CCOC(=O)CCCCCCCN1CCC(NC(=O)CCCCCN2CC[C@@H](NC(=O)c3cc(Cl)c(N)cc3OC)[C@@H](OC)C2)CC1]

To a solution of 6-((3S,4R)-4-(4-amino-5-chloro-2-methoxybenzamido)-3-methoxypiperidin-1-yl)hexanoic acid (7.5 g, 17.53 mmol, Preparation 14) in DMF (100 mL) were added HATU (10.66 g, 28.04 mmol), DIPEA (7.42 g, 57.41 mmol, 10 mL) at 15° C. The reaction mixture was stirred at 15° C. for 0.5 hours. Next, ethyl 8-(4-aminopiperidin-1-yl)octanoate hydrochloride (5.78 g, 16.84 mmol) was added and the mixture was stirred at 15° C. for 3 hours. The reaction mixture was then concentrated to remove most of the DMF, diluted with $H_2O$ (200 mL) and extracted with EtOAc (200 mL×2). The combined organic layers were washed with $H_2O$ (400 mL×3) followed by brine (500 mL), dried over $Na_2SO_4$, filtered and concentrated under reduced pressure. The residue was purified by column chromatography ($SiO_2$), using a gradient of petroleum ether/EtOAc (5:1 to 1:1), and the product was confirmed by TLC (DCM/MeOH=10:1, $R_f$=0.08). The title compound was obtained as a yellow oil (4 g). $^1H$ NMR (400 MHz, DMSO-$d_6$) δ ppm 8.08 (d, J=8.0 Hz, 1H), 7.78-7.72 (m, 2H), 6.50 (s, 1H), 5.99 (s, 2H), 4.10-3.90 (m, 4H), 3.85 (s, 3H), 3.50-3.33 (m, 5H), 3.00 (s, 3H), 2.40-2.15 (m, 8H), 2.04 (t, J=7.2 Hz, 2H), 1.85-1.55 (m, 4H), 1.54-1.26 (m, 11H), 1.26-1.10 (m, 13H).

PREPARATION 23: 8-(4-(6-((3S,4R)-4-(4-amino-5-chloro-2-methoxybenzamido)-3-methoxypiperidin-1-yl)hexanamido)piperidin-1-yl)octanoic acid

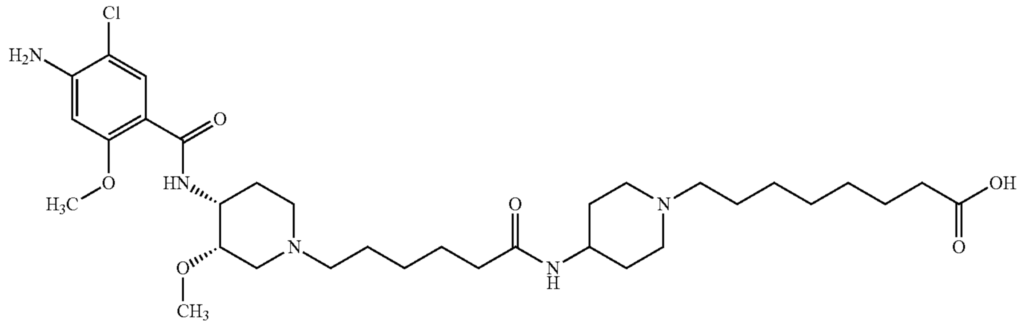 [SMILES: COc1cc(N)c(Cl)cc1C(=O)N[C@@H]1CCN(CCCCCC(=O)NC2CCN(CCCCCCCC(=O)O)CC2)C[C@@H]1OC]

To a solution of ethyl 8-(4-(6-((3S,4R)-4-(4-amino-5-chloro-2-methoxybenzamido)-3-methoxypiperidin-1-yl) hexanamido)piperidin-1-yl)octanoate (3.8 g, 5.59 mmol) in MeOH (30 mL) was added a solution of NaOH (665.00 mg, 16.63 mmol) in $H_2O$ (10 mL) at 0° C. The mixture was stirred at 40° C. for 0.5 hours and then adjusted to pH 7 with 1 M HCl and concentrated to give the title compound as a yellow solid (5 g, crude). ESI-MS m/z $[M+H]^+$ 652.4.

PREPARATION 24: ethyl (R)-8-(3-((tert-butoxycarbonyl)amino)piperidin-1-yl)octanoate

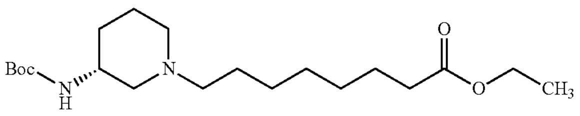 [SMILES: CCOC(=O)CCCCCCCN1CCC[C@@H](NC(=O)OC(C)(C)C)C1]

A mixture of tert-butyl (R)-piperidin-3-ylcarbamate (1.00 g, 4.99 mmol), ethyl 8-bromooctanoate (1.11 g, 4.42 mmol) and $K_2CO_3$ (924.05 mg, 6.69 mmol) in ACN (20 mL) was stirred at 15° C. for 12 hours. TLC (petroleum ether/EtOAc=1:1) indicated the starting material was consumed and one new major spot ($R_f$=0.11) was formed. The reaction mixture was concentrated and purified by column chromatography ($SiO_2$), using a gradient of petroleum ether/EtOAc (30:1 to 1:1), and the product was confirmed by TLC (petroleum ether/EtOAc=1:1, $R_f$=0.11). The title compound was obtained as a yellow oil (1.5 g, 92%).

$^1$H NMR (DMSO-$d_6$) δ ppm 4.98 (s, 1H), 4.16-4.10 (m, 2H), 3.73 (s, 1H), 2.45-2.30 (m, 2H), 2.27-2.20 (m, 5H), 1.62-1.55 (m, 6H), 1.55-1.35 (m, 9H), 1.34-1.30 (m, 1H), 1.27-1.15 (m, 9H); ESI-MS m/z $[M+H]^+$ 371.3.

PREPARATION 25: ethyl (R)-8-(3-aminopiperidin-1-yl)octanoate

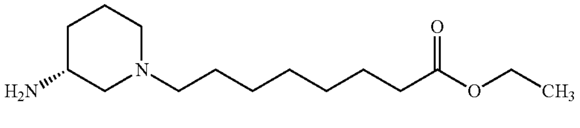 [SMILES: CCOC(=O)CCCCCCCN1CCC[C@@H](N)C1]

To a solution of ethyl (R)-8-(3-((tert-butoxycarbonyl) amino)piperidin-1-yl)octanoate (1.5 g, 4.05 mmol) in DCM (10 mL) was added 4 M HCl in dioxane (20 mL) at 10° C. The mixture was stirred at 10° C. for 12 hours. TLC (petroleum ether/EtOAc=1:1) indicated the starting material was consumed and one new major spot ($R_f$=0) was formed. The reaction mixture was concentrated to give an HCl salt of the title compound as a yellow solid (1.4 g, crude, 2 HCl). $^1$H NMR (DMSO-$d_6$) δ ppm 8.68-8.61 (m, 3H), 4.07-4.01 (m, 2H), 3.70-3.66 (m, 3H), 3.06 (s, 2H), 2.94-2.68 (m, 2H), 2.27 (t, J=7.2 Hz, 2H), 2.08-2.00 (m, 1H), 1.91-1.90 (m, 2H), 1.75-1.60 (m, 2H), 1.60-1.45 (m, 3H), 1.30-1.22 (m, 7H), 1.17 (t, J=7.2 Hz, 3H).

PREPARATION 26: methyl 6-((3S,4R)-4-(((benzyloxy)carbonyl)amino)-3-methoxypiperidin-1-yl) hexanoate

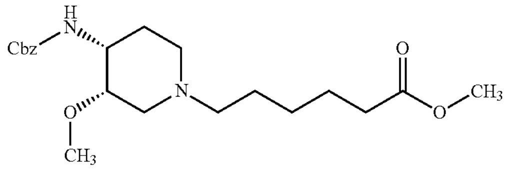 [SMILES: COC(=O)CCCCCN1CC[C@@H](NC(=O)OCc2ccccc2)[C@@H](OC)C1]

A mixture of benzyl ((3S,4R)-3-methoxypiperidin-4-yl) carbamate hydrochloride (1 g, 3.32 mmol), methyl 6-bromohexanoate (764.64 mg, 3.66 mmol), $K_2CO_3$ (1.15 g, 8.31 mmol), NaI (249.18 mg, 1.66 mmol, 0.5 eq) in DMF (10 mL) was stirred at 60° C. for 3 hours. TLC (DCM/MeOH=10:1, $R_f$=0.58) indicated the starting materials were completely consumed. The reaction mixture was washed with water (50 mL) and extracted with EtOAc (30 mL×3). The combined organic layers were dried over $Na_2SO_4$ and concentrated under vacuum. The resulting residue was purified by column chromatography ($SiO_2$), using petroleum ether/EtOAc (0:1) to obtain the title compound as a yellow oil (1.25 g, 95.8%). $^1$H NMR (DMSO-$d_6$) δ ppm 7.38-7.32 (m, 5H), 5.22 (d, J=8.4 Hz, 1H), 5.11 (s, 2H), 3.69 (s, 1H), 3.67 (s, 3H), 3.37 (s, 3H), 3.11 (d, J=3.2 Hz, 1H), 2.89 (d, J=3.2 Hz, 1H), 2.40-2.29 (m, 4H), 2.18-2.05 (m, 2H), 1.85-1.21 (m, 2H), 1.67-1.62 (m, 2H), 1.56-1.48 (m, 2H), 1.35-1.30 (m, 2H).

PREPARATION 27: 6-((3S,4R)-4-(((benzyloxy) carbonyl)amino) methoxypiperidin-1-yl)hexanoic acid

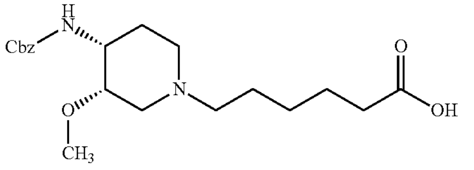 [SMILES: CO[C@H]1CN(CCCCCC(=O)O)CC[C@H]1NC(=O)OCc1ccccc1]

To a solution of methyl 6-((3S,4R)-4-(((benzyloxy)carbonyl)amino)-3-methoxypiperidin-1-yl)hexanoate (0.82 g, 2.09 mmol) in MeOH (5 mL) was added a solution of NaOH (250.69 mg, 6.27 mmol) in $H_2O$ (5 mL) at 10° C. The mixture was heated to 45° C., stirred for 2 hours and then concentrated to remove MeOH. The reaction mixture was diluted with $H_2O$ (20 mL) and washed with EtOAc (30 mL×2). The aqueous layer was adjusted to pH 5 with 1 M HCl and then concentrated under reduced pressure to give the title compound as a yellow solid (1 g, crude). ESI-MS m/z $[M+H]^+$ 379.2.

PREPARATION 28: methyl 8-(6-((3S,4R)-4-(((benzyloxy)carbonyl)amino)-3-methoxypiperidin-1-yl)-N-methylhexanamido)octanoate

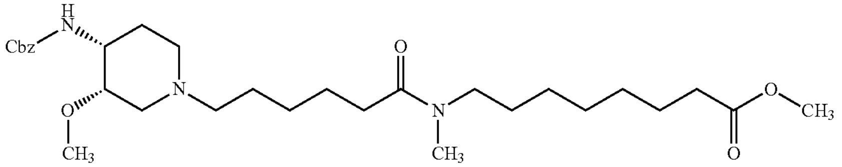 [SMILES: COC(=O)CCCCCCCN(C)C(=O)CCCCCN1CC[C@@H](NC(=O)OCc2ccccc2)[C@@H](OC)C1]

To a mixture of 6-((3S,4R)-4-(((benzyloxy)carbonyl)amino)-3-methoxypiperidin-1-yl)hexanoic acid (500 mg, 1.32 mmol) and methyl 8-(methylamino)octanoate hydrochloride (443.39 mg, 1.98 mmol) in DMF (10 mL) were added HATU (1.00 g, 2.64 mmol) and DIPEA (853.74 mg, 6.61 mmol, 1.15 mL). The mixture was stirred at 80° C. for 2 hours. TLC (DCM/MeOH=10:1, 12) showed the starting material was completely consumed and a new spot was formed. The reaction mixture was diluted with $H_2O$ (50 mL) and extracted with EtOAc (50 mL×3). The combined organic layers were washed with $H_2O$ (50 mL×3) and brine (50 mL), dried over anhydrous $Na_2SO_4$, filtered and concentrated under vacuum. The residue was purified by silica gel column chromatography, using a gradient of DCM/MeOH (200:1 to 10:1), and the product was confirmed by TLC (DCM/MeOH=10:1, 12, $R_f$=0.24). The title compound was obtained as a yellow oil (300 mg, 36.2% yield, 87.3% purity).

PREPARATION 29: methyl 8-(6-((3S,4R)-4-amino-3-methoxypiperidin-1-yl)-N-methylhexanamido) octanoate

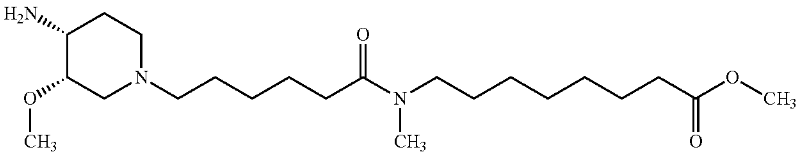 [SMILES: COC(=O)CCCCCCCN(C)C(=O)CCCCCN1CC[C@@H](N)[C@@H](OC)C1]

To a solution of methyl 8-(6-((3S,4R)-4-(((benzyloxy)carbonyl)amino)-3-methoxypiperidin-1-yl)-N-methylhexanamido)octanoate (280 mg, 511.21 μmol) in MeOH (5 mL) was added Pd/C (511.21 μmol, 15%) under $N_2$. The suspension was degassed under vacuum and purged with $H_2$ several times. The mixture was stirred under $H_2$ (15 psi) at 50° C. for 2 hours. TLC (DCM/MeOH=10:1) showed the starting material was completely consumed and a new spot was formed. The mixture was filtered, and the filtrate was concentrated under vacuum to give a sodium salt of the title compound as a yellow solid (140 mg, 66.2%).

PREPARATION 30: methyl 8-(6-((3S,4R)-4-(4-amino-5-chloro-2-methoxybenzamido)-3-methoxypiperidin-1-yl)-N-methylhexanamido)octanoate

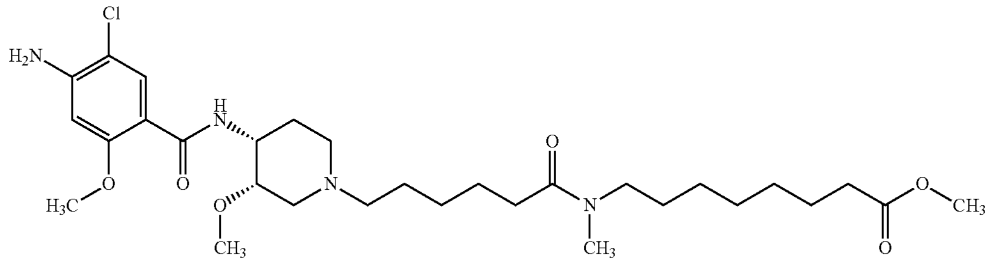 [SMILES: COC(=O)CCCCCCCN(C)C(=O)CCCCCN1CC[C@@H](NC(=O)c2cc(Cl)c(N)cc2OC)[C@@H](OC)C1]

To a mixture of methyl 8-(6-((3S,4R)-4-amino-3-methoxypiperidin-1-yl)-N-methylhexanamido)octanoate (140 mg, 338.50 μmol) and 4-amino-5-chloro-2-methoxybenzoic acid (75.07 mg, 372.35 μmol) in DMF (10 mL) were added HATU (257.41 mg, 676.99 μmol) and DIPEA (218.74 mg, 1.69 mmol, 294.79 μL). The reaction mixture was stirred at 20° C. for 10 hours. TLC (DCM/MeOH=10:1, 12) indicated the starting material was consumed and new spots were formed. The mixture was diluted with water (20 mL) and extracted with EtOAc (20 mL×2). The combined organic layers were washed with water (20 mL×3) and brine (20 mL), dried over $Na_2SO_4$, filtered and concentrated under vacuum. The residue was purified by silica gel chromatography, using a gradient of DCM/MeOH (200:1 to 10:1), and the product was confirmed by TLC (DCM/MeOH=10:1, 12, $R_f$=0.51). The title compound was obtained as a yellow oil (85 mg, 41% yield, 97% purity). ESI-MS m/z $[M+H]^+$ 597.5.

PREPARATION 31: 8-(6-((3S,4R)-4-(4-amino-5-chloro-2-methoxybenzamido) methoxypiperidin-1-yl)-N-methylhexanamido)octanoic acid

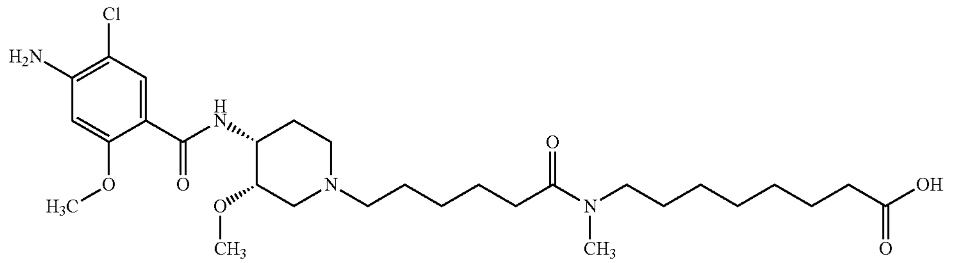 [SMILES: COc1cc(N)c(Cl)cc1C(=O)N[C@@H]1CCN(CCCCCC(=O)N(C)CCCCCCCC(=O)O)C[C@@H]1OC]

To a mixture of methyl 8-(6-((3S,4R)-4-(4-amino-5-chloro-2-methoxybenzamido)-3-methoxypiperidin-1-yl)-N-methylhexanamido)octanoate (85.00 mg, 138.06 μmol) in MeOH (5 mL) and $H_2O$ (1 mL) was added NaOH (11.05 mg, 276.13 μmol). The mixture was stirred at 80° C. for 3 hours. TLC (DCM/MeOH=10:1, 12) showed the starting material was mainly consumed and a new spot was formed. The mixture was concentrated under vacuum, adjusted to pH 7 with 1N HCl, and then concentrated under vacuum to give the title compound as a yellow solid (92 mg, crude). ESI-MS m/z $[M+H]^+$ 583.5.

PREPARATION 32: tert-butyl 3-(2-(tosyloxy)ethoxy)propanoate

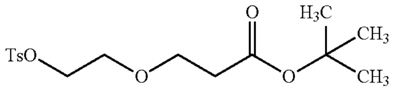 [SMILES: Cc1ccc(S(=O)(=O)OCCOCCC(=O)OC(C)(C)C)cc1]

To a solution of tert-butyl 3-(2-hydroxyethoxy)propanoate (1.8 g, 9.46 mmol) in DCM (18 mL) were added tosyl chloride (1.84 g, 9.65 mmol) and $Et_3N$ (2.87 g, 28.39 mmol, 3.95 mL) at 0° C. The mixture was stirred at 15° C. for 3 hours. TLC (petroleum ether/EtOAc=3:1) showed the starting material was completely consumed and new spots were formed. The reaction mixture was concentrated under reduce pressure and purified by column chromatography ($SiO_2$), using a gradient of petroleum ether/EtOAc (50/1 to 1:1). The title compound was obtained as a colorless oil (2.8 g, 86%). $^1H$ NMR (DMSO-$d_6$) δ ppm 7.78 (d, J=8.4 Hz, 2H), 7.34 (d, J=8 Hz, 2H), 4.13 (t, J=4.8 Hz, 2H), 3.76-3.62 (m, 4H), 2.53-2.49 (m, 3H), 2.45-2.38 (m, 2H), 1.66-1.40 (m, 9H); ESI-MS m/z $[M+H]^+$ 345.1.

PREPARATION 33: 3-methyltetrahydrofuran-2-ol

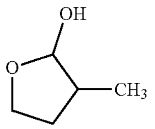

To a stirred solution of 3-methyldihydrofuran-2(3H)-one (14 g, 139.84 mmol, 13.21 mL) in DCM (250 mL) at −78° C. was added DIBAL-H (1.0 M, 167.81 mL) dropwise over 1.5 hours. The solution was stirred at −78° C. for 1.0 hour. TLC (petroleum ether/EtOAc=3:1) showed a new spot was formed. Next, a solution of sodium tartrate dihydrate (96.52 g, 419.52 mmol, 144.06 mL) in water (50 mL) and DCM (200 mL) was added and the resulting mixture was stirred at 10° C. for 10 minutes. The aqueous layer was separated and extracted with DCM (200 mL). The organic layers were combined, dried over $MgSO_4$ and concentrated to give the title compound as a yellow oil (14.5 g, crude). $^1H$ NMR ($CDCl_3$) δ ppm 5.19 (t, J=3.2 Hz, 1H), 3.91-3.73 (m, 2H), 2.44 (d, J=3.2 Hz, 2H), 2.15-2.10 (m, 1H), 1.03 (d, J=6.8 Hz, 3H).

PREPARATION 34: 3-(1,3-dithian-2-yl)butan-1-ol

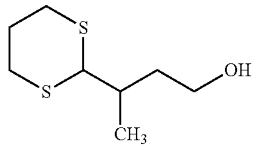

To a stirred solution of 3-methyltetrahydrofuran-2-ol (14.5 g, 141.97 mmol) in DCM (50 mL) at 0° C. were added molecular sieves 4A (10.00 g) and propane-1,3-dithiol (16.13 g, 149.07 mmol, 14.94 mL). Next, trifluoromethanesulfonic acid (8.52 g, 56.79 mmol, 5.01 mL) was added and the reaction mixture was allowed to warm to 15° C. and was stirred at 15° C. for 16 hours. TLC (petroleum ether/EtOAc=1:1) indicated the desired compound was formed. The mixture was filtered, and the filter cake was washed with DCM (200 mL). The filtrate and wash were treated with saturated aq $NaHCO_3$ (20 mL) and extracted with DCM (200 mL×4). The organic layers were combined, dried over $MgSO_4$ and concentrated. The residue was purified by silica gel column chromatography, using a gradient of petroleum ether/EtOAc (20:1 to 10:1). The title compound was obtained as a white-yellow oil (5.1 g, 19%). $^1H$ NMR ($CDCl_3$) δ ppm 4.20 (d, J=4.0 Hz, 1H), 3.81-3.69 (m, 2H), 2.94-2.88 (m, 4H), 2.13-2.10 (m, 2H), 1.94-1.90 (m, 2H), 1.65-1.61 (m, 1H), 1.45 (s, 1H), 1.14 (d, J=6.8 Hz, 3H).

PREPARATION 35: ethyl (E)-5-(1,3-dithian-2-yl)hex-2-enoate

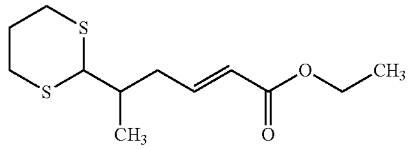 [SMILES: CCOC(=O)/C=C/CC(C)C1SCCCS1]

To a solution of 3-(1,3-dithian-2-yl)butan-1-ol (4.0 g, 20.80 mmol) in DCM (80 mL) were added DMSO (16.25 g, 208.00 mmol, 16.25 mL) and $Et_3N$ (15.57 g, 153.92 mmol, 21.42 mL) with stirring over a 10-minute period. The reaction mixture was cooled to 0° C. and $SO_3$·Py (15.99 g, 100.46 mmol) was added with stirring for 20 minutes. The mixture was then stirred at 15° C. for 2 hours under a $N_2$ atmosphere. Next, ethyl 2-(triphenyl-$\lambda^5$-phosphaneylidene) acetate (14.49 g, 41.60 mmol) was added with stirring, and the reaction mixture was stirred at 15° C. for 14 hours under a $N_2$ atmosphere. LCMS showed the starting material was completely consumed and the desired product was formed. The reaction mixture was quenched with water (60 mL) and extracted with EtOAc (60 mL×3). The combined organic layers were washed with saturated aq NaCl (100 mL), dried over $Na_2SO_4$, filtered and concentrated. The residue was purified by column chromatography ($SiO_2$) using a gradient of petroleum ether/EtOAc (20:1 to 4:1) to give the title compound as a yellow oil (3.7 g, 68%). $^1H$ NMR ($CDCl_3$) δ ppm 9.62 (s, 1H), 6.98-6.87 (m, 1H), 6.98-6.87 (m, 1H), 5.9 (dt, J=15.6 Hz, J=1.2 Hz, 1H), 4.26-4.13 (m, 2H), 2.68-2.55 (m, 2H), 2.29-2.25 (m, 2H), 1.3 (t, J=7.2 Hz, 3H), 1.17 (d, J=8.0 Hz, 3H).

PREPARATION 36: ethyl (E)-5-methyl-6-oxohex-2-enoate

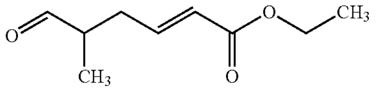

To a stirred solution of ethyl (E)-5-(1,3-dithian-2-yl)hex-2-enoate (4.6 g, 17.66 mmol) in ACN (60 mL) and $H_2O$ (15 mL) at 15° C. were added $CaCO_3$ (5.30 g, 52.99 mmol) and $CH_3I$ (25.07 g, 176.64 mmol, 11.00 mL). The reaction mixture was stirred at 60° C. for 17 hours. TLC (petroleum ether/EtOAc=5:1) indicated the starting material was completely consumed and many new spots were formed. The reaction mixture was filtered, and the filter cake was washed with EtOAc (50 mL×3). The filtrate and wash were combined, treated with water (60 mL) and extracted with EtOAc (40 mL×3). The combined organic layers were dried over $MgSO_4$ and concentrated. The residue was purified by column chromatography ($SiO_2$) using a gradient of petroleum ether/EtOAc (60:1 to 6:1) to give the title compound as a yellow oil (2.0 g, 67%). $^1H$ NMR ($CDCl_3$) δ ppm 9.62 (s, 1H), 6.98-6.87 (m, 1H), 6.98-6.87 (m, 1H), 5.9 (dt, J=15.6 Hz, J=1.2 Hz, 1H), 4.26-4.13 (m, 2H), 2.68-2.55 (m, 2H), 2.29-2.25 (m, 2H), 1.3 (t, J=7.2 Hz, 3H), 1.17 (d, J=8.0 Hz, 3H).

PREPARATION 37: ethyl 5-methyl-6-oxohexanoate

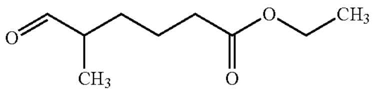

To a solution of ethyl (E)-5-methyl-6-oxohex-2-enoate (1.2 g, 7.05 mmol) in EtOH (30 mL) was added Pd/C (200 mg, 10%) under $N_2$ atmosphere. The suspension was degassed and purged with $H_2$ 3 times. The mixture was stirred under $H_2$ (15 psi) at 15° C. for 24 hours. TLC (petroleum ether/EtOAc=3:1) indicated the starting material was present and one new spot was formed. The mixture was stirred under $H_2$ (15 psi) at 15° C. for another 3 hours. TLC (petroleum ether/EtOAc=3:1) indicated the starting material was completely consumed and one new spot was formed. The reaction mixture was filtered through a syringe filter. The filtrate was concentrated to give the title compound as a yellow oil (1.1 g, crude). $^1H$ NMR ($CDCl_3$) δ ppm 9.64 (s, 1H), 4.17-4.12 (m, 2H), 2.36-2.32 (m, 2H), 1.77-1.67 (m, 3H), 1.45-1.37 (m, 1H), 1.29-1.25 (m, 3H), 2.23 (s, 6H), 1.13 (d, J=7.2 Hz, 3H).

PREPARATION 38: methyl 6-((3S,4R)-4-(((benzyloxy)carbonyl)amino) methoxypiperidin-1-yl)-5-methylhexanoate

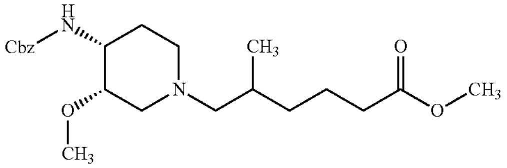 [SMILES: COC(=O)CCCC(C)CN1CC[C@@H](NC(=O)OCc2ccccc2)[C@@H](OC)C1]

To a solution of benzyl ((3S,4R)-3-methoxypiperidin-4-yl)carbamate hydrochloride (100 mg, 332.47 μmol) in DCE (2 mL) were added HOAc (19.97 mg, 332.47 μmol, 19.01 μL), $NaBH(OAc)_3$ (211.39 mg, 997.41 μmol) and ethyl 5-methyl-6-oxohexanoate (78.89 mg, 498.70 μmol). The mixture was stirred at 40° C. for 16 hours under $N_2$. LCMS showed benzyl ((3S,4R)-3-methoxypiperidin-4-yl)carbamate was completely consumed and the desired product was formed. The reaction mixture was cooled to 15° C. and adjusted to pH 9 with saturated aq $NaHCO_3$. The mixture was then extracted with EtOAc (15 mL×3) and the combined organic layers were washed with saturated aq NaCl (30 mL), dried over $Na_2SO_4$, filtered and concentrated. The residue was purified by column chromatography ($SiO_2$) using a gradient of DCM/MeOH (50:1 to 20:1) to give the title compound as a colorless oil (110 mg, 81.4%). $^1H$ NMR ($CDCl_3$) δ ppm 7.37-7.36 (m, 4H), 7.33-7.30 (m, 1H), 6.99 (d, J=8.0 Hz, 1H), 5.03 (s, 2H), 3.66 (s, 1H), 3.33 (s, 6H), 2.74 (s, 1H), 2.27-2.24 (m, 2H), 2.11-2.06 (m, 4H), 1.60-1.49 (m, 7H), 1.04-1.01 (m, 1H), 1.18 (dd, J=6.8 Hz, J=2.8 Hz, 3H).

PREPARATION 39: 6-((3S,4R)-4-(((benzyloxy)carbonyl)amino)-3-methoxypiperidin-1-yl)-5-methylhexanoic acid

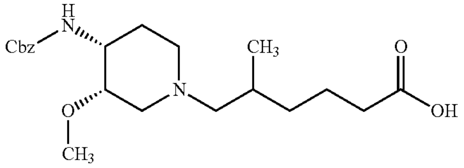 [SMILES: CO[C@H]1CN(CC(C)CCCC(=O)O)CC[C@H]1NC(=O)OCc1ccccc1]

To a solution of methyl 6-((3S,4R)-4-(((benzyloxy)carbonyl)amino)-3-methoxypiperidin-1-yl)-5-methylhexanoate (110 mg, 270.59 μmol) in THF (3 mL) and $H_2O$ (1 mL) was added $LiOH{\cdot}H_2O$ (45.42 mg, 1.08 mmol). The mixture was stirred at 15° C. for 14 hours. LCMS showed about 4% of starting material was present and the desired product was formed. The reaction mixture was concentrated, dissolved in water (10 mL) and adjusted to pH 10 with 1 N NaOH. Next, the mixture was extracted with EtOAc (10 mL×3) and the aqueous phase was concentrated to give the title compound as a white solid (110 mg, crude). $^1H$ NMR ($CDCl_3$) δ ppm 7.30-7.25 (m, 5H), 7.12-7.10 (m, 1H), 5.14 (d, J=8.4 Hz, 1H), 5.03 (s, 2H), 3.67 (s, 1H), 3.33 (s, 1H), 3.28 (s, 3H), 2.86 (s, 1H), 2.60 (s, 1H), 2.29 (s, 2H), 1.62-1.50 (m, 7H), 1.22-1.10 (m, 4H), 0.85-0.82 (m, 3H); ESI-MS m/z $[M+H]^+$ 393.3.

PREPARATION 40: methyl 8-(6-((3S,4R)-4-(((benzyloxy)carbonyl)amino)-3-methoxypiperidin-1-yl)-5-methylhexanamido)octanoate

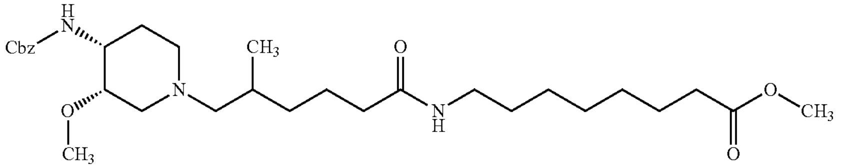 [SMILES: COC(=O)CCCCCCCNC(=O)CCCC(C)CN1CC[C@@H](NC(=O)OCc2ccccc2)[C@@H](OC)C1]

A mixture of 6-((3S,4R)-4-(((benzyloxy)carbonyl)amino)-3-methoxypiperidin-1-yl)-5-methylhexanoic acid (590 mg, 1.50 mmol), methyl 8-aminooctanoate (346.77 mg, 1.65 mmol, HCl), DIPEA (582.85 mg, 4.51 mmol, 785.51 μL), EDCI (576.34 mg, 3.01 mmol) and HOBt (406.24 mg, 3.01 mmol) in DMF (6 mL) was degassed and purged with $N_2$ 3 times and then stirred at 15° C. for 14 hours under $N_2$ atmosphere. LCMS indicated the starting material was completely consumed and the desired product was formed. The reaction mixture was quenched with water (30 mL) and extracted with EtOAc (20 mL×3). The combined organic layers were washed with saturated aq NaCl (60 mL), dried over $Na_2SO_4$, filtered and concentrated. The residue was purified by column chromatography ($SiO_2$) using a gradient of petroleum ether/EtOAc (20:1 to 1:6) to give the title compound as a red oil (400 mg, 48.6%). $^1H$ NMR ($CDCl_3$) δ ppm 7.30-7.24 (m, 5H), 5.11 (s, 1H), 5.03 (s, 2H), 3.65 (s, 1H), 3.59 (s, 3H), 3.28 (d, J=3.2 Hz, 1H), 3.25 (s, 3H), 3.18-3.15 (m, 2H), 2.85 (s, 1H), 2.65 (s, 1H), 2.22 (d, J=7.6 Hz, 1H), 2.21-2.05 (m, 4H), 1.97 (s, 2H), 1.56-1.41 (m, 10H), 1.24-1.19 (m, 8H), 0.82 (t, J=6.8 Hz, 3H); ESI-MS m/z $[M+H]^+$ 549.5.

PREPARATION 41: methyl 8-(6-((3S,4R)-4-amino-3-methoxypiperidin-1-yl)-5-methylhexanamido) octanoate

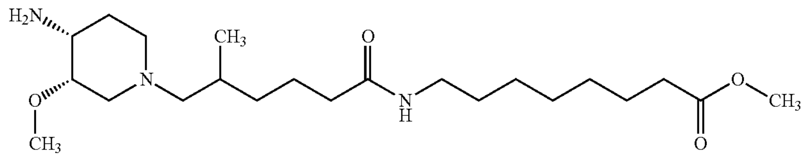 [SMILES: COC(=O)CCCCCCCNC(=O)CCCC(C)CN1CC[C@@H](N)[C@@H](OC)C1]

To a solution of methyl 8-(6-((3S,4R)-4-(((benzyloxy) carbonyl)amino) methoxypiperidin-1-yl)-5-methylhexanamido)octanoate (400 mg, 730.29 μmol) in MeOH (5 mL) was added Pd/C (0.1 g, 10%) under $N_2$ atmosphere. The suspension was degassed and purged with $H_2$ 3 times. The mixture was stirred under $H_2$ (15 psi) at 15° C. for 5 hours. TLC (DCM/MeOH=10/1) indicated the starting material was completely consumed and one main new spot was formed. The reaction mixture was filtered through a syringe filtered and the filtrate was concentrated to give the title compound as a colorless oil (300 mg, 99.3%). $^1H$ NMR ($CDCl_3$) δ ppm 5.56-5.49 (m, 1H), 3.60 (s, 3H), 3.42 (s, 1H), 3.32 (s, 3H), 3.22 (t, J=3.2 Hz, 1H), 3.17-3.15 (m, 2H), 2.89 (s, 1H), 2.62 (s, 1H), 2.44 (s, 1H), 2.23 (t, J=7.6 Hz, 2H), 2.09-2.06 (m, 6H), 1.62-1.58 (m, 7H), 1.44-1.35 (m, 3H), 1.25-1.23 (m, 6H), 1.10-0.99 (m, 1H), 0.83-0.80 (m, 3H); ESI-MS m/z $[M+H]^+$ 414.3.

PREPARATION 42: methyl 8-(6-((3S,4R)-4-(4-amino-5-chloro-2-methoxybenzamido)-3-methoxypiperidin-1-yl)-5-methylhexanamido)octanoate

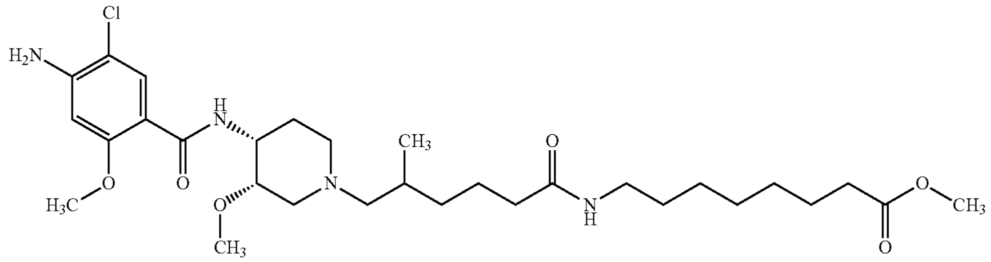 [SMILES: COC(=O)CCCCCCCNC(=O)CCCC(C)CN1CC[C@@H](NC(=O)c2cc(Cl)c(N)cc2OC)[C@@H](OC)C1]

A mixture of methyl 8-(6-((3S,4R)-4-amino-3-methoxypiperidin-1-yl)-5-methylhexanamido)octanoate (250 mg, 604.46 μmol), 4-amino-5-chloro-2-methoxybenzoic acid (134.05 mg, 664.91 μmol), DIPEA (234.37 mg, 1.81 mmol, 315.86 μL), EDCI (173.81 mg, 906.69 μmol) and HOBt (122.51 mg, 906.69 μmol) in DMF (2 mL) was degassed and purged with $N_2$ 3 times and then stirred at 15° C. for 14 hours under $N_2$ atmosphere. TLC (DCM/MeOH=10:1) indicated the starting material was completely consumed and many new spots were formed. The reaction mixture was quenched with water (25 mL) and extracted with EtOAc (15 mL×3). The combined organic layers were washed with saturated aq NaCl (30 mL), dried over $Na_2SO_4$, filtered and concentrated. The residue was purified by preparative TLC ($SiO_2$) using DCM/MeOH (10/1). The title compound was obtained as a colorless oil (190 mg, 52.6%). $^1H$ NMR ($CDCl_3$) δ ppm 8.09 (d, J=4.4 Hz, 1H), 8.03 (s, 1H), 6.23 (s, 1H), 5.48 (s, 1H), 4.30 (s, 2H), 4.13 (s, 1H), 3.82 (s, 3H), 3.59 (s, 3H), 3.35 (s, 4H), 3.18-3.13 (m, 2H), 2.89-2.81 (m, 1H), 2.61 (s, 1H), 2.22 (t, J=7.2 Hz, 2H), 2.10-2.07 (m, 6H), 1.73-1.62 (m, 4H), 1.42-1.40 (m, 3H), 1.24-1.20 (m, 7H), 1.06 (s, 1H), 0.86-0.82 (m, 3H); ESI-MS m/z $[M+H]^+$ 597.3.

PREPARATION 43: 8-(6-((3S,4R)-4-(4-amino-5-chloro-2-methoxybenzamido) methoxypiperidin-1-yl)-5-methylhexanamido)octanoic acid

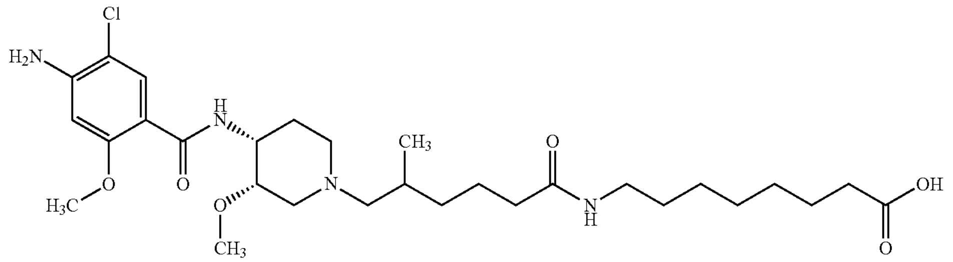 [SMILES: COc1cc(N)c(Cl)cc1C(=O)N[C@@H]1CCN(CC(C)CCCC(=O)NCCCCCCCC(=O)O)C[C@@H]1OC]

To a solution of methyl 8-(6-((3S,4R)-4-(4-amino-5-chloro-2-methoxybenzamido)-3-methoxypiperidin-1-yl)-5-methylhexanamido)octanoate (230 mg, 385.14 μmol) in MeOH (3 mL) and $H_2O$ (1 mL) was added NaOH (61.62 mg, 1.54 mmol). The mixture was stirred at 30° C. for 14 hours. TLC (DCM/MeOH=10:1) indicated the starting material was completely consumed and a new spot was formed. The reaction mixture was adjusted to pH 7 with 1N HCl and then concentrated to give the title compound as a white gum (200 mg, 89.1%). $^1H$ NMR ($CDCl_3$) δ ppm 8.09 (d, J=7.6 Hz, 1H), 7.74 (s, 2H), 6.53 (s, 1H), 5.99 (s, 2H), 4.01 (s, 1H), 3.87 (s, 3H), 3.37 (s, 3H), 3.01 (d, J=6.0 Hz, 2H), 2.77 (s, 1H), 2.16-2.03 (m, 9H), 1.71-1.47 (m, 11H), 1.25 (s, 7H), 0.99 (s, 1H), 0.84 (s, 3H); ESI-MS m/z $[M+H]^+$ 583.3.

PREPARATION 44: 3,7-dimethyloct-6-en-1-yl acetate

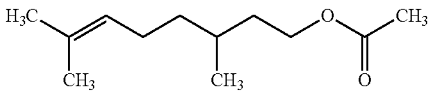

To a solution of 3,7-dimethyloct-6-en-1-ol (10 g, 63.99 mmol) in DCM (100 mL) were added DIPEA (24.81 g, 191.98 mmol, 33.44 mL) and $Ac_2O$ (7.19 g, 70.39 mmol, 6.59 mL). The mixture was stirred at 20° C. for 16 hours. TLC (petroleum ether/EtOAc=10:1, $R_f$=0.79) indicated the starting material was consumed and one major new spot with lower polarity was detected. The reaction mixture was concentrated under reduced pressure and purified by column chromatography ($SiO_2$) using a gradient of petroleum ether/EtOAc (1:0 to 100:1) to give the title compound as a colorless oil (12 g, 95%). $^1H$ NMR ($CDCl_3$) δ ppm 5.06-5.10 (m, 1H), 4.06-4.13 (m, 2H), 2.03 (s, 3H), 1.68-1.95 (m, 2H), 1.64-1.65 (m, 1H), 1.53-1.60 (m, 4H), 1.44-1.45 (m, 3H), 1.34-1.42 (m, 1H), 1.17-1.19 (m, 2H), 0.92-1.17 (d, 1H), 0.90 (d, 3H).

PREPARATION 45: 3-methyl-6-oxohexyl acetate

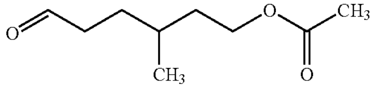

A solution of 3,7-dimethyloct-6-en-1-yl acetate (6 g, 30.26 mmol) in DCM (50 mL) was purged with ozone at −78° C. for 30 minutes and then with $O_2$ until there was no ozone observed in the off-gas. Next, $Me_2S$ (10.63 g, 171.08 mmol, 12.57 mL) was added and the mixture was stirred at 25° C. for 2 hours. TLC (petroleum ether/EtOAc=5:1, $R_f$=0.4) indicated the starting material was consumed and one major new spot with larger polarity was detected. The reaction mixture was concentrated under reduced pressure and purified by column chromatography ($SiO_2$) using a gradient of petroleum ether/EtOAc (10:1 to 5:1) to give the title compound as a yellow oil (4.6 g, 88%). $^1H$ NMR ($CDCl_3$) δ ppm 9.68-9.73 (m, 1H), 3.99-4.07 (m, 2H), 2.28-2.47 (m, 2H), 1.97 (s, 3H), 1.56-1.67 (m, 2H), 1.49-1.55 (m, 1H), 1.37-1.47 (m, 2H), 0.86 (d, J=6.4 Hz, 2H), 0.84 (br s, 1H).

PREPARATION 46: 6-acetoxy-4-methylhexanoic acid

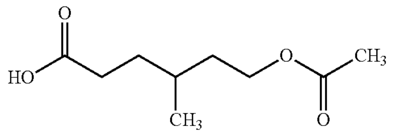

To a solution of 3-methyl-6-oxohexyl acetate (4.6 g, 26.71 mmol), TEMPO (336.02 mg, 2.14 mmol) and $NaH_2PO_4$ (16.02 g, 133.55 mmol) in $H_2O$ (15 mL) and ACN (40 mL) were added a solution NaClO (1.99 g, 1.34 mmol, 1.64 mL, 5% purity) and sodium chlorite (3.62 g, 40.06 mmol) in $H_2O$ (10 mL) at 35° C. The mixture was stirred at 35° C. for 3 hours. TLC (petroleum ether/EtOAc=3:1, $R_f$=0.02) indicated the starting material was almost consumed and a single product was formed. The reaction mixture was quenched with saturated aq $Na_2SO_3$ solution (100 mL) and extracted with EtOAc (100 mL×3). The combined organic layers were dried over anhydrous $Na_2SO_4$, filtered and concentrated under reduced pressure to give the title compound as a yellow oil (3.7 g, 74%). $^1H$ NMR ($CDCl_3$) δ ppm 11.00 (br s, 1H), 4.00-4.18 (m, 2H), 2.24-2.50 (m, 2H), 2.03 (s, 3H), 1.41-1.73 (m, 5H), 0.92 (d, J=6.4 Hz, 3H).

PREPARATION 47: methyl 6-hydroxy-4-methylhexanoate

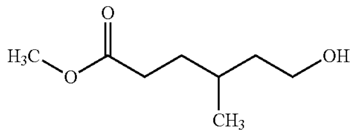

To a solution of 6-acetoxy-4-methylhexanoic acid (3.7 g, 19.66 mmol) in MeOH (20 mL) was added concentrated $H_2SO_4$ (7.31 g, 73.07 mmol, 4 mL, 98%). The mixture was stirred at 60° C. for 3 hours. TLC (petroleum ether/EtOAc=3:1, $R_f$=0.19) indicated the starting material was completely consumed and one new spot was formed. The mixture was quenched with water (50 mL) and extracted with EtOAc (30 mL×3). The combined organic layers were dried over anhydrous $Na_2SO_4$, filtered and concentrated under reduced pressure to give the title compound as a yellow oil (2.5 g, 79%). $^1$H NMR ($CDCl_3$) δ ppm 3.99-4.30 (m, 2H), 3.61-3.76 (m, 2H), 3.61-3.76 (m, 1H), 3.47 (s, 1H), 2.18-2.42 (m, 2H), 1.38-1.71 (m, 5H), 0.90 (dd, J=6.0 Hz, J=2.8 Hz, 3H).

PREPARATION 48: methyl 6-bromo-4-methylhexanoate

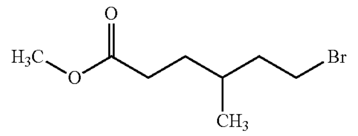

To a solution of methyl 6-hydroxy-4-methylhexanoate (2.5 g, 15.60 mmol) in DCM (20 mL) were added $CBr_4$ (6.21 g, 18.73 mmol) and $PPh_3$ (4.91 g, 18.73 mmol) at 0° C. The mixture was stirred at 20° C. for 1 hour. TLC (petroleum ether/EtOAc=5:1, $R_f$=0.57) indicated the starting material was completely consumed and two new spots were formed. The reaction mixture was diluted with $H_2O$ (100 mL) and extracted with DCM (150 mL×2). The combined organic layers were dried over anhydrous $Na_2SO_4$, filtered, concentrated under reduced pressure and purified by column chromatography ($SiO_2$) using a gradient of petroleum ether/EtOAc (10/1 to 5:1) to give the title compound as a yellow oil (1 g, 29%). $^1$H NMR ($CDCl_3$) δ ppm 3.67 (s, 2H), 3.66 (br s, 1H), 3.35-3.52 (m, 2H), 2.23-2.40 (m, 2H), 1.81-1.92 (m, 1H), 1.64-1.73 (m, 3H), 1.43-1.52 (m, 1H), 0.90-0.93 (m, 3H).

PREPARATION 49: methyl 6-((3S,4R)-4-(4-amino-5-chloro-2-methoxybenzamido)-3-methoxypiperidin-1-yl)-4-methylhexanoate

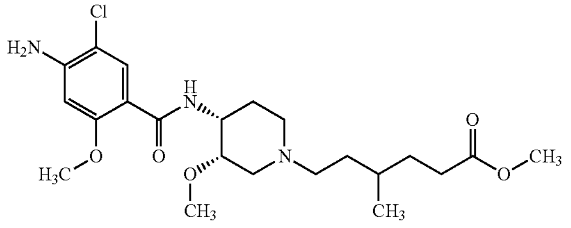 [SMILES: COC(=O)CCC(C)CCN1CC[C@@H](NC(=O)c2cc(Cl)c(N)cc2OC)[C@@H](OC)C1]

To a solution of 4-amino-5-chloro-2-methoxy-N-((3S,4R)-3-methoxypiperidin-4-yl)benzamide (1.07 g, 3.06 mmol, HCl) and methyl 6-bromo-4-methylhexanoate (0.8 g, 3.59 mmol) in DMF (15 mL) were added $K_2CO_3$ (2.12 g, 15.32 mmol) and NaI (4.59 mg, 30.65 μmol). The mixture was stirred at 50° C. for 12 hours and then diluted with $H_2O$ (60 mL) and extracted with EtOAc (80 mL×3). The combined organic layers were washed with brine (150 mL×2), dried over anhydrous $Na_2SO_4$, filtered and concentrated under reduced pressure. The residue was purified by column chromatography ($SiO_2$) using a gradient of DCM/MeOH (1:0 to 20:1, $R_f$=0.25) to give the title compound as a yellow oil (1.01 g, 72.3%). $^1$H NMR ($CDCl_3$) δ ppm 8.19 (br d, J=8.0 Hz, 1H), 8.09 (s, 1H), 8.02 (s, 1H), 6.30 (s, 1H), 4.39 (s, 2H), 4.19 (br s, 1H), 3.88 (s, 3H), 3.67 (s, 3H), 3.44-3.47 (m, 1H), 3.43-3.45 (m, 1H), 3.44 (s, 3H), 3.00-3.14 (m, 1H), 2.96 (s, 4H), 2.73-2.86 (m, 1H), 2.30-2.38 (m, 2H), 2.11-2.29 (m, 3H), 2.10-2.55 (m, 2H), 1.80-1.96 (m, 2H), 1.63-1.76 (m, 1H), 1.28-1.57 (m, 4H), 0.91 (d, J=6.0 Hz, 3H); ESI-MS m/z $[M+H]^+$ 456.2.

PREPARATION 50: 6-((3S,4R)-4-(4-amino-5-chloro-2-methoxybenzamido) methoxypiperidin-1-yl)-4-methylhexanoic acid

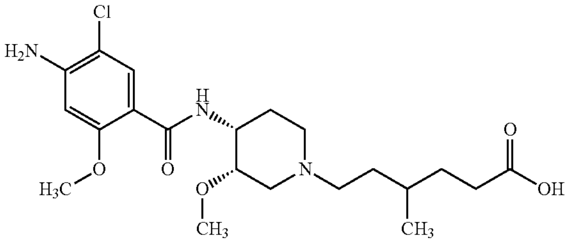 [SMILES: COc1cc(N)c(Cl)cc1C(=O)N[C@@H]1CCN(CCC(C)CCC(=O)O)C[C@@H]1OC]

To a solution of methyl 6-((3S,4R)-4-(4-amino-5-chloro-2-methoxybenzamido)-3-methoxypiperidin-1-yl)-4-methylhexanoate (1 g, 2.19 mmol) in THF (18 mL), $H_2O$ (6 mL) and MeOH (6 mL) was added $LiOH{\cdot}H_2O$ (276.09 mg, 6.58 mmol). The mixture was stirred at 35° C. for 12 hours and then adjusted to pH 7 with 1 M HCl and concentrated under reduced pressure to give the title compound as a yellow solid (1.4 g, crude). ESI-MS m/z $[M+H]^+$ 442.2.

PREPARATION 51: methyl 8-(6-((3S,4R)-4-(4-amino-5-chloro-2-methoxybenzamido)-3-methoxypiperidin-1-yl)-4-methylhexanamido)octanoate

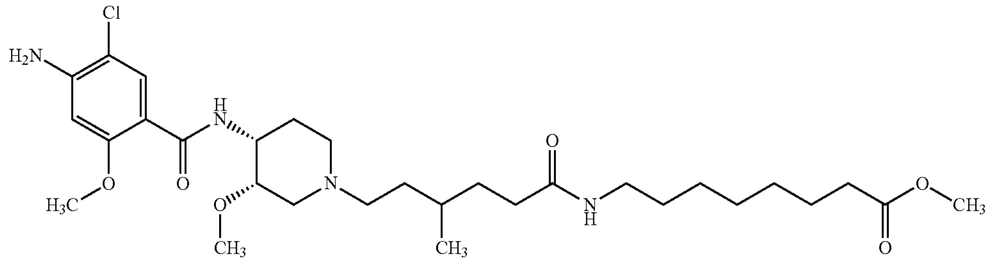 [SMILES: COC(=O)CCCCCCCNC(=O)CCC(C)CCN1CC[C@@H](NC(=O)c2cc(Cl)c(N)cc2OC)[C@@H](OC)C1]

To a solution of 6-((3S,4R)-4-(4-amino-5-chloro-2-methoxybenzamido)-3-methoxypiperidin-1-yl)-4-methylhexanoic acid (1.3 g, 2.94 mmol) in DMF (15 mL) were added EDCI (845.84 mg, 4.41 mmol), HOBt (596.20 mg, 4.41 mmol), DIPEA (1.14 g, 8.82 mmol, 1.54 mL) and methyl 8-aminooctanoate (690.90 mg, 3.29 mmol, HCl). The mixture was stirred at 50° C. for 12 hours and then diluted with $H_2O$ (40 mL) and extracted with EtOAc (50 mL×3). The combined organic layers were washed with brine (50 mL×2), dried over anhydrous $Na_2SO_4$, filtered and concentrated under reduced pressure. The residue was purified by preparative TLC ($SiO_2$, DCM/MeOH=10:1, $R_f$=0.26) followed by preparative HPLC (Phenomenex Luna C-18, 250×50 mm, 10 μm) using a gradient (25 to 50%) of ACN/water(0.1% TFA) to give the title compound as a red oil (600 mg, 34.2%). $^1H$ NMR ($CDCl_3$) δ ppm 8.48 (br d, J=6.4 Hz, 1H), 8.26 (br s, 2H), 8.00 (s, 1H), 6.79 (br s, 1H), 6.33 (s, 1H), 4.43 (br s, 1H), 3.84-3.97 (m, 4H), 3.63-3.67 (m, 4H), 3.45-3.50 (m, 1H), 3.25 (br d, J=5.6 Hz, 3H), 3.00 (br s, 2H), 2.31 (br t, J=7.2 Hz, 8H), 2.07-2.45 (m, 1H), 1.68 (br d, J=7.2 Hz, 9H), 1.32 (br s, 8H), 0.94 (br d, J=6.0 Hz, 3H); ESI-MS m/z $[M+H]^+$ 597.3.

PREPARATION 52: 8-(6-((3S,4R)-4-(4-amino-5-chloro-2-methoxybenzamido) methoxypiperidin-1-yl)-4-methylhexanamido)octanoic acid

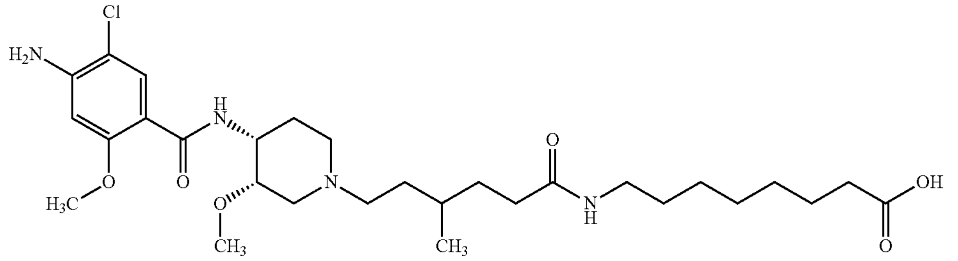 [SMILES: COc1cc(N)c(Cl)cc1C(=O)N[C@@H]1CCN(CCC(C)CCC(=O)NCCCCCCCC(=O)O)C[C@@H]1OC]

To a solution of methyl 8-(6-((3S,4R)-4-(4-amino-5-chloro-2-methoxybenzamido)-3-methoxypiperidin-1-yl)-4-methylhexanamido)octanoate (600 mg, 1.00 mmol) in THF (12 mL), $H_2O$ (3 mL) and MeOH (3 mL) was added $LiOH{\cdot}H_2O$ (126.48 mg, 3.01 mmol). The mixture was stirred at 35° C. for 12 hours. LCMS indicated the presence of starting material. NaOH (160.74 mg, 4.02 mmol) was added and the mixture was stirred at 35° C. for 2 hours. LCMS showed the starting material was completely consumed and one main peak with desired mass was detected. The reaction mixture was adjusted to pH 7 with 1 M HCl, concentrated under reduced pressure, and distilled with toluene to remove water. The title compound was obtained as a yellow solid (600 mg, crude) which was used without further purification. ESI-MS m/z $[M+H]^+$ 583.3.

PREPARATION 53: 1-(tert-butyl) 6-methyl (E)-3-methylhex-2-enedioate

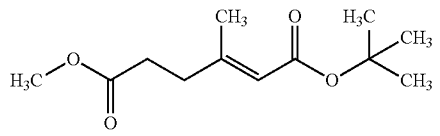 [SMILES: COC(=O)CC/C(C)=C/C(=O)OC(C)(C)C]

To a solution of tert-butyl 2-(dimethoxyphosphoryl)acetate (19.92 g, 88.87 mmol, 17.63 mL) in THF (30 mL) was added NaH (3.84 g, 95.98 mmol, 60%) at 0° C. The mixture was stirred at 15° C. for 30 minutes. Next, a solution of methyl 4-oxopentanoate (9.6 g, 73.77 mmol, 9.14 mL) in THF (10 mL) was added and the mixture was stirred at 15° C. for 4 hours. TLC (petroleum ether/EtOAc=3:1, $R_f$=0.5) indicated the starting material was completely consumed and a new spot was formed. The reaction mixture was then diluted with $H_2O$ (100 mL×3) at 0° C. and extracted with EtOAc (200 mL×3). The combined organic layers were dried over anhydrous $Na_2SO_4$ and concentrated under reduce pressure to give the title compound as yellow oil (18 g, 83% yield, 93.9% purity). $^1H$ NMR ($CDCl_3$) δ ppm 5.57-5.54 (m, 1H), 3.67-3.62 (m, 3H), 2.82-2.80 (m, 1H), 2.46-2.36 (m, 3H), 2.07 (d, J=0.8 Hz, 2H), 1.81 (d, J=1.2 Hz, 1H), 1.47-1.36 (m, 9H); ESI-MS m/z $[M+23]^+$ 251.2.

PREPARATION 54: 1-(tert-butyl) 6-methyl 3-methylhexanedioate

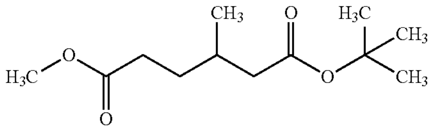 [SMILES: COC(=O)CCC(C)CC(=O)OC(C)(C)C]

To a solution of 1-(tert-butyl) 6-methyl (E)-3-methylhex-2-enedioate (18 g, 74.04 mmol) in MeOH (150 mL) was added Pd/C (1 g, 60%) under $N_2$. The suspension was degassed under vacuum and purged with $H_2$ several times. The mixture was stirred under $H_2$ (15 psi) at 15° C. for 12 hours. TLC (petroleum ether/EtOAc=10:1, $R_f$=0.5) indicated the starting material was completely consumed and a new spot was formed. The reaction mixture was filtered, and the filtrate was concentrated under reduce pressure to give the title compound as a colorless oil (17 g, 100%). $^1H$ NMR ($CDCl_3$) δ ppm 3.64 (s, 3H), 2.32-2.28 (m, 2H), 2.26-2.20 (m, 1H), 2.16-2.02 (m, 1H), 1.99-1.80 (m, 1H), 1.70-1.66 (m, 1H), 1.53-1.49 (m, 1H), 1.42-1.38 (m, 9H), 0.92 (d, J=6.8 Hz, 3H); ESI-MS m/z $[M+23]^+$ 253.1.

PREPARATION 55: 6-(tert-butoxy)-4-methyl-6-oxohexanoic acid

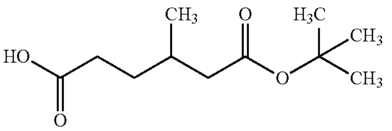

A solution of 1-(tert-butyl) 6-methyl 3-methylhexanedioate (17 g, 73.82 mmol) in THF (170 mL) was added to a solution of $LiOH \cdot H_2O$ (3.25 g, 77.51 mmol) in $H_2O$ (10 mL). The mixture was stirred at 30° C. for 6 hours. TLC (petroleum ether/EtOAc=3:1, $R_f$=0.15) indicated the starting material was completely consumed and new spots were formed. The reaction mixture was extracted with EtOAc (1000 mL×3). The organic layers were set aside, and the aqueous phase was acidified to pH 4 with 1 M HCl (50 mL) and extracted with EtOAc (50 mL×4). The organic layers were combined, dried over anhydrous $Na_2SO_4$ and concentrated under reduce pressure to give the title compound as a crude yellow oil (14.8 g, 92.7%). $^1H$ NMR ($CDCl_3$) δ ppm 11.18 (s, 1H), 2.44-2.31 (m, 2H), 2.23-2.18 (m, 1H), 2.09-2.03 (m, 1H), 1.98-1.93 (m, 1H), 1.74-1.67 (m, 1H), 1.56-1.53 (m, 1H), 1.44 (s, 9H), 0.95 (d, J=6.4 Hz, 3H); ESI-MS m/z $[M-55]^+$ 161.1.

PREPARATION 56: tert-butyl 6-hydroxy-3-methylhexanoate

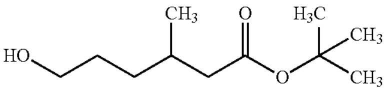

To a solution of 6-(tert-butoxy)-4-methyl-6-oxohexanoic acid (14.8 g, 68.43 mmol) in THF (150 mL) was added $BH_3 \cdot THF$ (1 M, 136.86 mL) at 0° C. The mixture was stirred at 0° C. for 3 hours and then at 15° C. for another 10 hours. TLC (petroleum ether/EtOAc=3:1, $R_f$=0.40) indicated the starting material was completely consumed and a main new spot was formed. The reaction mixture was concentrated, diluted with $H_2O$ (100 mL) and extracted with EtOAc (100 mL×2). The combined organic layers were washed with brine (50 mL), dried over $Na_2SO_4$ and concentrated under reduce pressure to give the title compound as a yellow oil (12.87 g, 92.97% yield). $^1H$ NMR ($CDCl_3$) δ ppm 3.78-3.71 (m, 2H), 3.63 (s, 1H), 2.23-2.18 (m, 1H), 2.07-1.89 (m, 2H), 1.63-1.52 (m, 2H), 1.44-1.40 (m, 9H), 1.39-1.33 (m, 1H), 1.25 (s, 1H), 0.95-0.92 (m, 3H).

PREPARATION 57: tert-butyl 3-methyl-6-(tosyloxy)hexanoate

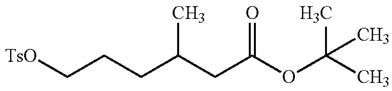

To a solution of tert-butyl 6-hydroxy-3-methylhexanoate (12.87 g, 63.62 mmol) in DCM (120 mL) were added tosyl chloride (12.13 g, 63.62 mmol), DMAP (7.77 g, 63.62 mmol) and DIPEA (24.67 g, 190.86 mmol, 33.25 mL) at 0° C. The mixture was stirred at 10° C. for 6 hours. TLC (petroleum ether/EtOAc=5:1, $R_f$=0.6) indicated the starting material was nearly consumed and new spots were formed. The reaction mixture was concentrated under reduce pressure and purified by column chromatography ($SiO_2$) using a gradient of petroleum ether/EtOAc (50/1 to 10:1) to give the title compound as a yellow oil (1.3 g, 5.73%). ESI-MS m/z $[M+23]^+$ 379.2.

PREPARATION 58: tert-butyl 6-((3S,4R)-4-(4-amino-5-chloro-2-methoxybenzamido)-3-methoxypiperidin-1-yl)-3-methylhexanoate

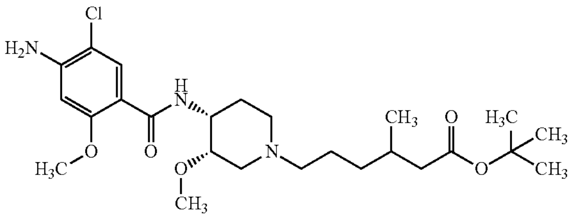 [SMILES: COc1cc(N)c(Cl)cc1C(=O)N[C@@H]1CCN(CCCC(C)CC(=O)OC(C)(C)C)C[C@@H]1OC]

To a solution of 4-amino-5-chloro-2-methoxy-N-((3S,4R)-3-methoxypiperidin-4-yl)benzamide (1.30 g, 3.70 mmol, HCl) and tert-butyl 3-methyl-6-(tosyloxy)hexanoate (1.2 g, 3.37 mmol) in DMF (5 mL) were added $K_2CO_3$ (930.48 mg, 6.73 mmol) and NaI (50.46 mg, 336.63 μmol). The mixture was stirred at 80° C. for 2 hours and then diluted with $H_2O$ (80 mL) and extracted with EtOAc (30 mL×4). The combined organic layers were washed with $H_2O$ (150 mL), dried over anhydrous $Na_2SO_4$ and concentrated under reduce pressure. The residue was purified by column chromatography ($SiO_2$), using a gradient of petroleum ether/EtOAc (100:1 to 0:1), and the product was confirmed by TLC (DCM/MeOH=10:1, $R_f$=0.4). The title compound was obtained as a yellow oil (576 mg, 32.0% yield, 93.16% purity). ESI-MS m/z $[M+H]^+$ 498.2.

PREPARATION 59: 6-((3S,4R)-4-(4-amino-5-chloro-2-methoxybenzamido) methoxypiperidin-1-yl)-3-methylhexanoic acid

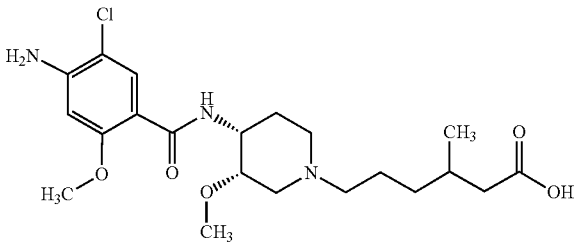 [SMILES: COc1cc(N)c(Cl)cc1C(=O)N[C@@H]1CCN(CCCC(C)CC(=O)O)C[C@@H]1OC]

To a solution of tert-butyl 6-((3S,4R)-4-(4-amino-5-chloro-2-methoxybenzamido)-3-methoxypiperidin-1-yl)-3-methylhexanoate (450 mg, 841.72 μmol) in DCM (15 mL) was added TFA (1.54 g, 13.51 mmol, 1 mL) at 15° C. The mixture was stirred at 25° C. for 10 hours and then concentrated to give a TFA salt of the title compound as a yellow oil (650 mg, crude). ESI-MS m/z $[M+H]^+$ 442.2.

PREPARATION 60: methyl 8-(6-((3S,4R)-4-(4-amino-5-chloro-2-methoxybenzamido)-3-methoxypiperidin-1-yl)-3-methylhexanamido)octanoate

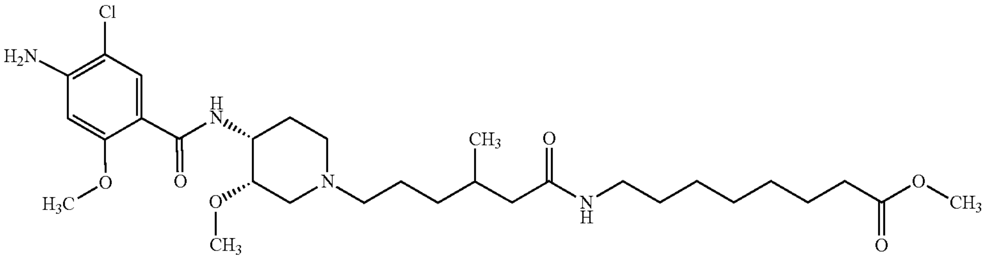 [SMILES: COC(=O)CCCCCCCNC(=O)CC(C)CCCN1CC[C@@H](NC(=O)c2cc(Cl)c(N)cc2OC)[C@@H](OC)C1]

To a solution of 6-((3S,4R)-4-(4-amino-5-chloro-2-methoxybenzamido)-3-methoxypiperidin-1-yl)-3-methylhexanoic acid (600 mg, 1.08 mmol, TFA) in DMF (15 mL) were added HATU (820.68 mg, 2.16 mmol) and DIPEA (418.43 mg, 3.24 mmol, 563.93 μL) at 15° C. The mixture was stirred at 15° C. for 15 minutes at which time methyl 8-aminooctanoate (294.22 mg, 1.40 mmol, HCl) was added. The mixture was stirred at 15° C. for 2 hours and then diluted with $H_2O$ (50 mL) and extracted with EtOAc (100 mL×2). The combined organic layers were washed with $H_2O$ (200 mL×3) followed by brine (250 mL), dried over $Na_2SO_4$, filtered and concentrated under reduced pressure. The residue was purified by column chromatography ($SiO_2$), using a gradient of petroleum ether/EtOAc (5:1 to 0:1), and the product was confirmed by TLC (DCM/MeOH=20:1, $R_f$=0.35). The title compound was obtained as a yellow solid (700 mg, 86% purity). ESI-MS m/z $[M+H]^+$ 597.5.

PREPARATION 61: 8-(6-((3S,4R)-4-(4-amino-5-chloro-2-methoxybenzamido) methoxypiperidin-1-yl)-3-methylhexanamido)octanoic acid

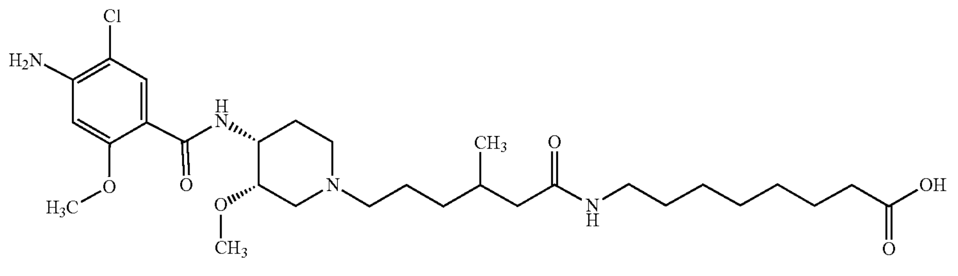 [SMILES: COc1cc(N)c(Cl)cc1C(=O)N[C@@H]1CCN(CCCC(C)CC(=O)NCCCCCCCC(=O)O)C[C@@H]1OC]

To a solution of methyl 8-(6-((3S,4R)-4-(4-amino-5-chloro-2-methoxybenzamido)-3-methoxypiperidin-1-yl)-3-methylhexanamido)octanoate (600 mg, 1.00 mmol) in MeOH (10 mL) was added a solution of NaOH (80.37 mg, 2.01 mmol) in $H_2O$ (2 mL) at 10° C. The mixture was heated to 40° C. for 1 hour. The reaction mixture was adjusted to pH 7 with 1N HCl and then concentrated to give the title compound as a yellow solid (750 mg, crude). ESI-MS m/z $[M+H]^+$ 583.3.

PREPARATION 62: methyl 6-(4-(4-amino-5-chloro-2,3-dihydrobenzofuran-7-carboxamido)piperidin-1-yl)hexanoate

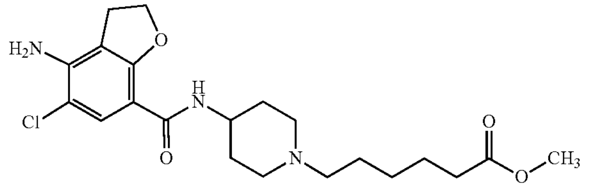 [SMILES: COC(=O)CCCCCN1CCC(NC(=O)c2cc(Cl)c(N)c3c2OCC3)CC1]

A mixture of methyl 6-(4-aminopiperidin-1-yl)hexanoate dihydrochloride (3.4 g, 11.29 mmol), 4-amino-5-chloro-2,3-dihydrobenzofuran-7-carboxylic acid (2.4 g, 11.24 mmol), DIPEA (5.81 g, 44.94 mmol, 7.83 mL) and HATU (6.41 g, 16.85 mmol) in DMF (30 mL) was stirred at 30° C. for 12 hours. TLC (EtOH/EtOAc=1:1) indicated methyl 6-(4-aminopiperidin-1-yl)hexanoate was consumed and one new major spot ($R_f$=0.39) was formed. The mixture was diluted with $H_2O$ (40 mL) and extracted with EtOAc (40 mL×2). The combined organic layers were dried over $Na_2SO_4$, filtered, concentrated under reduced pressure and triturated in EtOAc (20 mL). The title compound was obtained as a yellow solid (3.83 g, 70.8% yield, 88% purity). $^1H$ NMR (DMSO-$d_6$) δ ppm 7.45 (s, 1H), 7.31 (d, J=6.8 Hz, 1H), 5.90 (s, 2H), 4.73 (t, J=8.8 Hz, 2H), 3.94 (s, 1H), 3.59 (s, 3H), 3.28-3.23 (m, 1H), 3.23-3.00 (m, 3H), 2.95-2.70 (m, 4H), 2.32 (t, J=7.2 Hz, 2H), 1.99 (d, J=4.4 Hz, 2H), 1.82-1.45 (m, 6H), 1.35-1.18 (m, 2H); ESI-MS m/z $[M+H]^+$ 424.2.

PREPARATION 63: 6-(4-(4-amino-5-chloro-2,3-dihydrobenzofuran carboxamido)piperidin-1-yl) hexanoic acid

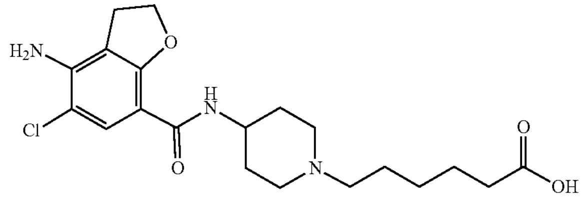 [SMILES: Nc1c(Cl)cc(C(=O)NC2CCN(CCCCCC(=O)O)CC2)c2c1CCO2]

To a mixture of methyl 6-(4-(4-amino-5-chloro-2,3-dihydrobenzofuran-7-carboxamido)piperidin-1-yl)hexanoate (3.6 g, 7.47 mmol) dissolved in MeOH (30 mL) was added NaOH (1.20 g, 29.89 mmol) in $H_2O$ (10 mL) at 10° C. The reaction mixture was stirred at 10° C. for 12 hours. TLC (EtOH/EtOAc=1:1) indicated methyl 6-(4-(4-amino-5-chloro-2,3-dihydrobenzofuran-7-carboxamido)piperidin-1-yl)hexanoate was consumed and one new major spot ($R_f$=0) was formed. The reaction mixture was concentrated to remove MeOH, diluted with $H_2O$ (40 mL) and washed with EtOAc (30 mL×2). The aqueous layer was adjusted to pH 7 with 1 M HCl to pH=7. A resulting precipitate was collected by filtration to give the title compound as a white solid (2.7 g, 80% yield, 91% purity). $^1H$ NMR (DMSO-$d_6$) δ ppm 7.46 (s, 1H), 7.27 (d, J=7.6 Hz, 1H), 5.86 (s, 2H), 4.73 (t, J=8.8 Hz, 2H), 3.80-3.75 (m, 1H), 3.03 (t, J=8.8 Hz, 2H), 2.78-2.63 (m, 2H), 2.24-2.21 (m, 4H), 2.16 (t, J=9.6 Hz, 2H), 1.84-1.72 (m, 2H), 1.49-1.25 (m, 8H).

PREPARATION 64: ethyl (R)-8-(3-(6-(4-(4-amino-5-chloro-2,3-dihydrobenzofuran-7-carboxamido)piperidin-1-yl)hexanamido)piperidin-1-yl)octanoate

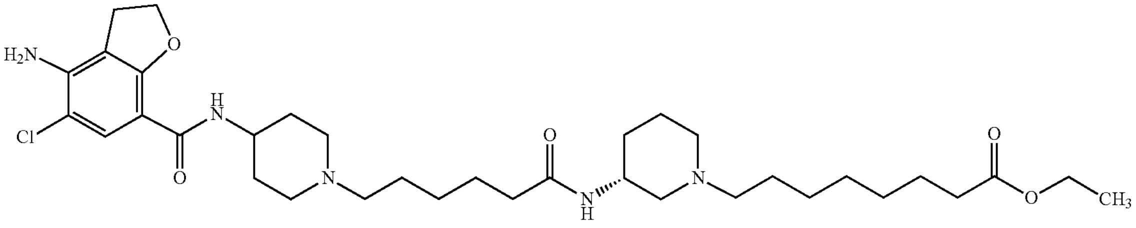 [SMILES: CCOC(=O)CCCCCCCN1CCC[C@@H](NC(=O)CCCCCN2CCC(NC(=O)c3cc(Cl)c(N)c4c3OCC4)CC2)C1]

A mixture of 6-(4-(4-amino-5-chloro-2,3-dihydrobenzofuran-7-carboxamido)piperidin-1-yl)hexanoic acid (400 mg, 888.01 μmol, prepared according to PREPARATION 63), ethyl (R)-8-(3-aminopiperidin-1-yl)octanoate hydrochloride (286.69 mg, 1.06 mmol, 2 HCl, prepared according to PREPARATION 25), DIPEA (459.06 mg, 3.55 mmol, 618.69 μL), HATU (364.00 mg, 957.32 μmol) in DMF (10 mL) was stirred at 80° C. for 3 hours. LCMS showed ethyl (R)-8-(3-aminopiperidin-1-yl)octanoate was completely consumed and the desired MS was detected. The reaction mixture was diluted with $H_2O$ (50 mL) and extracted with EtOAc (100 mL×2). The organic layers were combined, washed with $H_2O$ (200 mL×3) followed by brine (250 mL), dried over $Na_2SO_4$, filtered and concentrated under reduced pressure. The residue was purified by column chromatography ($SiO_2$) using a gradient of EtOAc/EtOH(50:1 to 1:1), and the product was confirmed by TLC (EtOAc/EtOH=1:1, $R_f$=0.06). The title compound was obtained as a yellow oil (400 mg, 68.0%). $^1$H NMR (DMSO-$d_6$) δ ppm 7.86 (s, 1H), 6.16 (s, 1H), 4.78 (t, J=8.4 Hz, 2H), 4.33 (s, 2H), 4.00-3.82 (m, 2H), 3.07 (t, J=8.8 Hz, 2H), 2.95-2.79 (m, 2H), 2.60-2.35 (m, 4H), 2.32-2.10 (m, 9H), 2.03-1.94 (m, 2H), 1.68-1.40 (m, 14H), 1.39-1.24 (m, 14H); ESI-MS m/z $[M+H]^+$ 662.6.

PREPARATION 65: (R)-8-(3-(6-(4-(4-amino-5-chloro-2,3-dihydrobenzofuran-7-carboxamido)piperidin-1-yl)hexanamido)piperidin-1-yl)octanoic acid

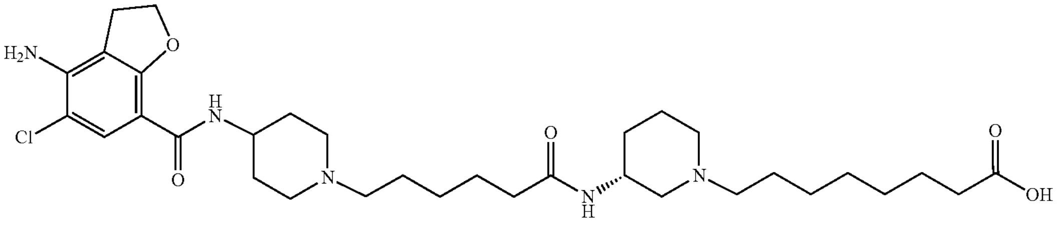 [SMILES: Nc1c(Cl)cc(C(=O)NC2CCN(CCCCCC(=O)N[C@@H]3CCCN(CCCCCCCC(=O)O)C3)CC2)c2c1CCO2]

To a mixture of ethyl (R)-8-(3-(6-(4-(4-amino-5-chloro-2,3-dihydrobenzofuran-7-carboxamido)piperidin-1-yl)hexanamido)piperidin-1-yl)octanoate (350 mg, 528.46 μmol) in $H_2O$ (3 mL) and MeOH (10 mL) was added NaOH (42.27 mg, 1.06 mmol) at 0° C. The mixture was stirred at 50° C. for 1 hour and then concentrated to remove the solvents. The residue was dissolved in water (10 mL) and extracted with DCM (10 mL×2). The aqueous layer was adjusted to pH 7 with 1 M HCl and concentrated under vacuum to give the title compound as a white solid (480 mg, crude). ESI-MS m/z $[M+H]^+$ 634.4.

PREPARATION 66: methyl 9-bromononanoate

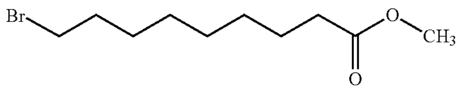

To a solution of 9-bromononanoic acid (1 g, 4.22 mmol) in MeOH (8 mL) was added $SOCl_2$ (1.51 g, 12.65 mmol, 917.74 μL) at 0° C. The solution was stirred at 80° C. for 2 hours. TLC (petroleum ether/EtOAc=3:1) indicated the starting material was consumed and one new major spot ($R_f$=0.67) was formed. The reaction mixture was concentrated to give the title compound as a yellow oil. $^1$H NMR (DMSO-$d_6$) δ ppm 3.67 (s, 3H), 3.41 (t, J=6.8 Hz, 2H), 2.31 (t, J=7.6 Hz, 2H), 1.88-1.83 (m, 2H), 1.63 (t, J=6.8 Hz, 2H),1.45-1.32 (m, 8H).

PREPARATION 67: methyl 9-(4-((4-(((tert-butoxycarbonyl)amino)methyl)piperidin-1-yl)methyl)piperidin-1-yl)nonanoate

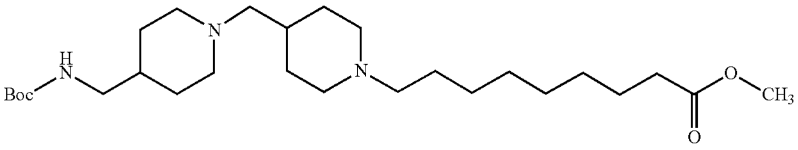 [SMILES: COC(=O)CCCCCCCCN1CCC(CN2CCC(CNC(=O)OC(C)(C)C)CC2)CC1]

A mixture of tert-butyl ((1-(piperidin-4-ylmethyl)piperidin-4-yl)methyl)carbamate (500 mg, 1.61 mmol), methyl 9-bromononanoate (403.20 mg, 1.61 mmol), $K_2CO_3$ (443.73 mg, 3.21 mmol) and NaI (12.03 mg, 80.27 μmol) in DMF (8 mL) was stirred at 80° C. for 3 hours. TLC (petroleum ether/EtOAc=3:1) indicated tert-butyl ((1-(piperidin ylmethyl)piperidin-4-yl)methyl)carbamate was consumed and one new major spot ($R_f$=0) was formed. The reaction mixture was diluted with $H_2O$ (10 mL) and extracted with EtOAc (10 mL×2). The combined organic layers were washed with $H_2O$ (20 mL×3) followed by brine (25 mL), dried over $Na_2SO_4$, filtered and concentrated under reduced pressure. The residue was purified by column chromatography ($SiO_2$), using a gradient of petroleum ether/EtOAc (30:1 to 0:1), and the product was confirmed by TLC (petroleum ether/EtOAc=0:1, $R_f$=0.05). The title compound was obtained as a yellow solid (330 mg, 42.7%). $^1$H NMR (DMSO-$d_6$) δ ppm 6.80 (t, J=5.6 Hz, 1H), 3.57 (s, 3H), 2.85-2.68 (m, 6H), 2.28 (t, J=7.2 Hz, 2H), 2.19 (t, J=7.6 Hz, 2H), 2.04 (d, J=7.2 Hz, 2H), 1.82-1.71 (m, 5H), 1.63-1.46 (m, 6H), 1.44-1.38 (m, 2H), 1.36 (s, 9H), 1.24 (s, 9H), 1.12-0.96 (m, 4H); ESI-MS m/z $[M+H]^+$ 482.4.

PREPARATION 68: methyl 9-(4-((4-(aminomethyl)piperidin-1-yl)methyl)piperidin-1-yl)nonanoate

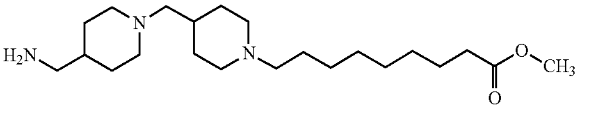 [SMILES: COC(=O)CCCCCCCCN1CCC(CN2CCC(CN)CC2)CC1]

To a solution of methyl 9-(4-((4-(((tert-butoxycarbonyl)amino)methyl)piperidin-1-yl)methyl)piperidin-1-yl)nonanoate (330 mg, 685.06 μmol) in DCM (5 mL) was added 4 M HCl in dioxane (5 mL) at 0° C. The mixture was warmed to 15° C. and stirred for 1 hour. TLC (petroleum ether/EtOAc=1:1) indicated the starting material was consumed and one new major spot ($R_f$=0) was formed. The reaction mixture was concentrated to give an HCl salt of the title compound as a yellow solid (360 mg, crude, 3 HCl). $^1$H NMR (DMSO-$d_6$) δ ppm 10.60-10.49 (m, 2H), 8.20 (s, 3H), 3.63-3.56 (m, 6H), 3.47-3.40 (m, 3H), 3.21-3.0 (m, 2H), 2.95-2.78 (m, 6H), 2.75-2.60 (m, 2H), 2.29 (t, J=7.2 Hz, 2H), 2.15-1.85 (m, 5H), 1.80-1.40 (m, 9H), 1.26 (s, 8H).

PREPARATION 69: methyl 9-(4-((4-((4-amino-5-chloro-2,3-dihydrobenzofuran carboxamido)methyl)piperidin-1-yl)methyl)piperidin-1-yl)nonanoate

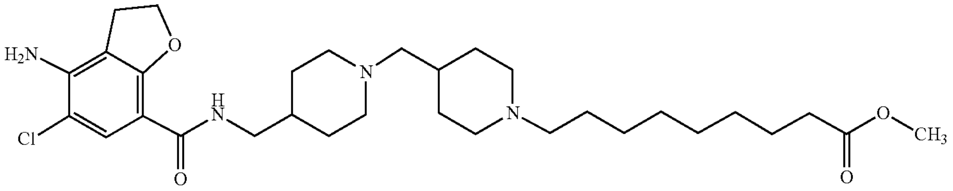 [SMILES: COC(=O)CCCCCCCCN1CCC(CN2CCC(CNC(=O)c3cc(Cl)c(N)c4c3OCC4)CC2)CC1]

A mixture of methyl 9-(4-((4-(aminomethyl)piperidin-1-yl)methyl)piperidin-1-yl)nonanoate (157.94 mg, 739.34 μmol), 4-amino-5-chloro-2,3-dibenzofuran-7-carboxylic acid (330 mg, 672.13 μmol), HATU (384 mg, 1.01 mmol) and DIPEA (694.94 mg, 5.38 mmol, 936.58 μL) in DMF (15 mL) was stirred at 15° C. for 12 hours. The reaction mixture was diluted with $H_2O$ (30 mL) and extracted with EtOAc (20 mL×2). The combined organic layers were washed with $H_2O$ (80 mL×3) followed by brine (100 mL), dried over $Na_2SO_4$, filtered and concentrated under reduced pressure. The residue was purified by column chromatography ($SiO_2$), using a gradient of petroleum ether/EtOAc (3:1 to 1:1), and the product was confirmed by TLC (DCM/MeOH=10:1, $R_f$=0.05). The title compound was obtained as a yellow solid (260 mg, 65.7% yield, 98% purity). $^1$H NMR (DMSO-$d_6$) δ ppm 7.46-7.40 (m, 2H), 5.86 (s, 2H), 4.72 (t, J=8.8 Hz, 2H), 3.59-3.58 (m, 1H), 3.58-3.56 (m, 4H), 3.25-3.15 (m, 4H), 3.05-2.95 (m, 3H), 2.80-2.68 (m, 4H), 2.36-2.24 (m, 2H), 2.24-2.10 (m, 2H), 2.00-1.94 (m, 2H), 1.80-1.65 (m, 8H), 1.42-1.36 (m, 4H), 1.20-1.05 (m, 7H); ESI-MS m/z $[M+H]^+$ 577.3.

PREPARATION 70: 9-(4-((4-((4-amino-5-chloro-2,3-dihydrobenzofuran-7-carboxamido)methyl)piperidin-1-yl)methyl)piperidin-1-yl)nonanoic acid

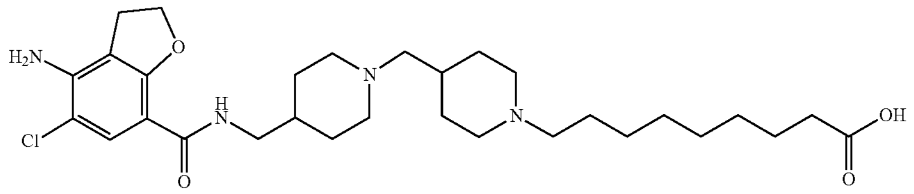 [SMILES: Nc1c(Cl)cc(C(=O)NCC2CCN(CC3CCN(CCCCCCCCC(=O)O)CC3)CC2)c2c1CCO2]

To a solution of methyl 9-(4-((4-((4-amino-5-chloro-2,3-dihydrobenzofuran-7-carboxamido)methyl)piperidin-1-yl)methyl)piperidin-1-yl)nonanoate (1.7 g, 2.95 mmol) in MeOH (15 mL) was added a solution of NaOH (480 mg, 12.00 mmol) in $H_2O$ (5 mL) at 0° C. The mixture was stirred at 45° C. for 2 hours. TLC (DCM/MeOH=10:1) indicated the starting material was consumed and one new major spot ($R_f$=0) was formed. The reaction mixture was adjusted to pH 8 with 1 M HCl and then concentrated to give the title compound as a white solid (2.3 g, crude). ESI-MS m/z $[M+H]^+$ 563.3.

PREPARATION 71: tert-butyl (3S,4R)-4-(4-amino-5-chloro-2,3-dihydrobenzofuran-7-carboxamido)-3-methoxypiperidine-1-carboxylate

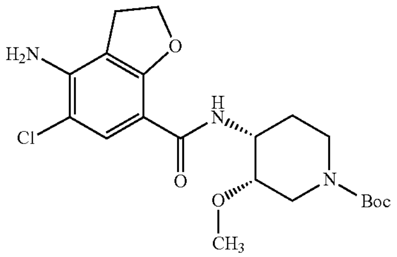 [SMILES: CO[C@H]1CN(C(=O)OC(C)(C)C)CC[C@H]1NC(=O)c1cc(Cl)c(N)c2c1OCC2]

To a solution of 4-amino-5-chloro-2,3-dihydrobenzofuran-7-carboxylic acid (5 g, 24.80 mmol) in DMF (100 mL) were added HATU (13.35 g, 35.10 mmol) and DIPEA (9.08 g, 70.20 mmol, 12.26 mL). The reaction mixture was stirred at 20° C. for 0.5 hours. Next, tert-butyl (3S,4R)-4-amino-3-methoxypiperidine-1-carboxylate (6.47 g, 28.1 mmol) was added at 20° C. The mixture was stirred at 20° C. for 2 hours and then concentrated to remove most of the DMF, diluted with $H_2O$ (100 mL) and extracted with EtOAc (200 mL×2). The combined organic layers were washed with $H_2O$ (500 mL×3) followed by brine (500 mL), dried over $Na_2SO_4$, filtered and concentrated under reduced pressure to give the title compound as a yellow solid (7.4 g, crude). ESI-MS m/z $[M+H]^+$ 426.3.

PREPARATION 72: 4-amino-5-chloro-N-((3S,4R)-3-methoxypiperidin-4-yl)-2,3-dihydrobenzofuran-7-carboxamide

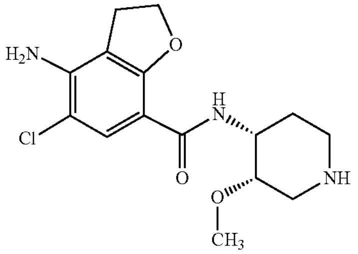 [SMILES: CO[C@H]1CNCC[C@H]1NC(=O)c1cc(Cl)c(N)c2c1OCC2]

To a solution of tert-butyl (3S,4R)-4-(4-amino-5-chloro-2,3-dihydrobenzofuran-7-carboxamido)-3-methoxypiperidine-1-carboxylate (7.4 g, 25.62 mmol) in DCM (20 mL) was added 4 M HCl in dioxane (13.03 mL, 52.10 mmol) at 0° C. The mixture was stirred at 15° C. for 0.5 hours. The reaction mixture was concentrated to give an HCl salt of the title compound as a yellow solid (5.5 g, crude). ESI-MS m/z $[M+H]^+$ 326.0.

EXAMPLE 1

4-amino-5-chloro-2-methoxy-N-((3S,4R)-3-methoxy-1-(6-oxo-6-(((2S,3R,4R,5R)-2,3,4,5,6-pentahydroxyhexyl)amino)hexyl)piperidin-4-yl)benzamide

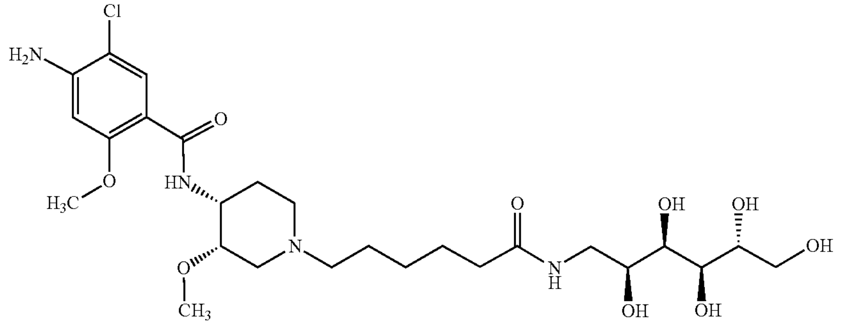 [SMILES: COc1cc(N)c(Cl)cc1C(=O)N[C@@H]1CCN(CCCCCC(=O)NC[C@H](O)[C@@H](O)[C@H](O)[C@H](O)CO)C[C@@H]1OC]

To a solution of 6-((3S,4R)-4-(4-amino-5-chloro-2-methoxybenzamido) methoxypiperidin-1-yl)hexanoic acid (1.5 g, 3.51 mmol, Preparation 4) in DMF (35 mL) were added HATU (2.67 g, 7.01 mmol), DIPEA (1.36 g, 10.52 mmol, 1.84 mL) and (2R,3R,4R,5S)-6-aminohexane-1,2,3,4,5-pentaol (1.91 g, 10.52 mmol). The reaction mixture was stirred at 80° C. for 1 hour and then was diluted with $H_2O$ (5 mL), concentrated and purified by preparative HPLC (Kromasil Eternity XT, 250×80 mm, 10 μm) using a gradient (10 to 40%) of ACN/water (0.05% ammonia hydroxide). The title compound was obtained as a white solid (1.679 g, 99% purity). $^1H$ NMR (DMSO-$d_6$) δ ppm 8.04-8.15 (m, 1H), 7.69-7.77 (m, 1H), 6.45-6.54 (m, 1H), 5.94-6.03 (m, 2H), 4.12-5.00 (m, 5H), 3.92-4.08 (m, 1H), 3.37-3.70 (m, 7H), 3.20-3.31 (m, 7H), 2.94-3.16 (m, 2H), 2.02-2.31 (m, 6H), 1.31-1.84 (m, 7H), 1.15-1.30 (m, 3H); ESI-MS m/z $[M+H]^+$ 591.7.

EXAMPLE 2

4-amino-5-chloro-2-methoxy-N-((3S,4R)-3-methoxy-1-(6-oxo-6-((8-oxo-8-(((2S,3R,4R,5R)-2,3,4,5,6-pentahydroxyhexyl)amino)octyl)amino)hexyl)piperidin-4-yl)benzamide A solution of 8-amino-N-((2S,3R,4R,5R)-2,3,4,5,6-pentahydroxyhexyl)octanamide (5.00 g, 11.50 mmol), 6-((3S,4R)-4-(4-amino-5-chloro-2-methoxybenzamido)-3-methoxypiperidin-1-yl)hexanoic acid (7.41 g, 23.00 mmol, Preparation 14), T3P (10.98 g, 17.25 mmol, 10.26 mL, 50% purity) and DIPEA (2.97 g, 23.00 mmol, 4.01 mL) in DMF (100 mL) was stirred at 25° C. for 2 hours. The reaction mixture was quenched with $H_2O$ (20 mL), concentrated in vacuo and purified by preparative HPLC (Phenomenex Luna C-18, 250×50 mm, 10 μm) using a gradient (10 to 40%) of ACN/water (0.05% HCl). The title compound was obtained as a white solid (6.70 g, 7.99 mmol, 34.7% yield, 91.7% purity). $^1H$ NMR (400 MHz, DMSO-$d_6$) δ ppm 7.94 (s, 1H), 7.00 (s, 1H), 4.30 (br s, 1H), 4.01 (s, 3H), 3.88-3.80 (m, 3H), 3.77-3.70 (m, 4H), 3.69-3.66 (m, 4H), 3.58 (s, 3H), 3.26 (s, 2H), 3.24-3.18 (m, 7H), 2.37 (dd, J=8.0 Hz, J=15.2 Hz, 5H), 2.09 (s, 2H), 1.74-1.66 (m, 8H), 1.56 (s, 3H), 1.46-1.38 (m, 10H); ESI-MS m/z $[M+H]^+$ 732.4.

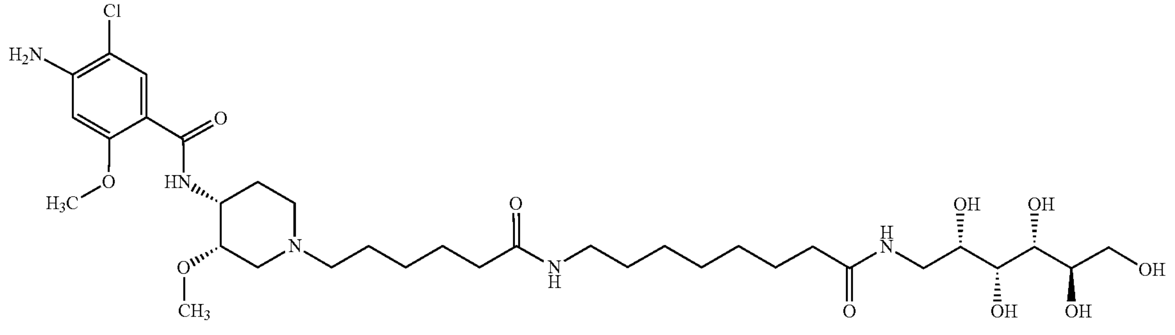 [SMILES: COc1cc(N)c(Cl)cc1C(=O)N[C@@H]1CCN(CCCCCC(=O)NCCCCCCCC(=O)NC[C@H](O)[C@@H](O)[C@H](O)[C@H](O)CO)C[C@@H]1OC]

EXAMPLE 3

4-amino-5-chloro-2-methoxy-N-((3S,4R)-3-methoxy-1-(6-oxo-6-((6-oxo-6-(((2S,3R,4R,5R)-2,3,4,5,6-pentahydroxyhexyl)amino)hexyl)amino)hexyl)piperidin yl)benzamide

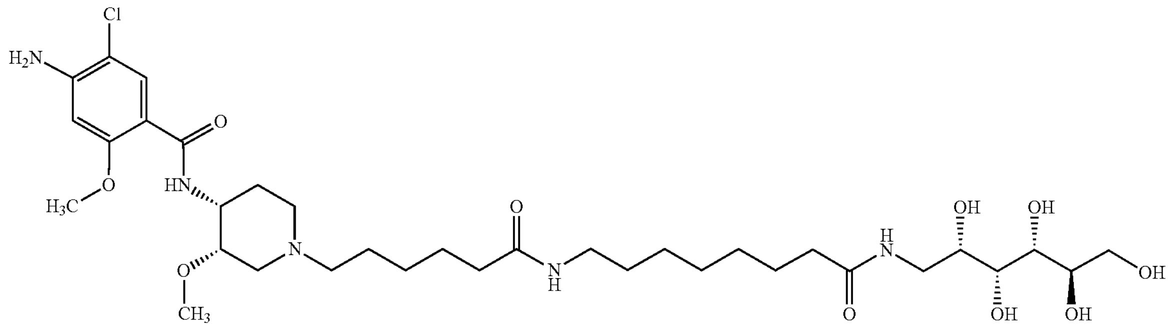 [SMILES: COc1cc(N)c(Cl)cc1C(=O)N[C@@H]1CCN(CCCCCC(=O)NCCCCCCCC(=O)NC[C@H](O)[C@@H](O)[C@H](O)[C@H](O)CO)C[C@@H]1OC]

The title compound was prepared like Example 2, using 6-amino-N-((2S,3R,4R,5R)-2,3,4,5,6-pentahydroxyhexyl)hexanamide in place of 8-amino-N-((2S,3R,4R,5R)-2,3,4,5,6-pentahydroxyhexyl)octanamide, and was obtained as a colorless oil. ESI-MS m/z $[M+H]^+$ 705.3.

EXAMPLE 4

4-amino-5-chloro-2-methoxy-N-((3S,4R)-3-methoxy-1-(6-oxo-6-((4-oxo-4-(((2S,3R,4R,5R)-2,3,4,5,6-pentahydroxyhexyl)amino)butyl)amino)hexyl)piperidin-4-yl)benzamide

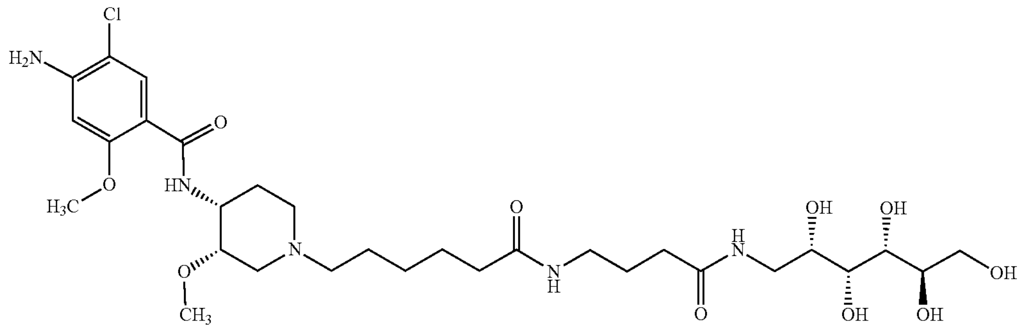 [SMILES: COc1cc(N)c(Cl)cc1C(=O)N[C@@H]1CCN(CCCCCC(=O)NCCCC(=O)NC[C@H](O)[C@@H](O)[C@H](O)[C@H](O)CO)C[C@@H]1OC]

The title compound was prepared like Example 2, using 4-amino-N-((2S,3R,4R,5R)-2,3,4,5,6-pentahydroxyhexyl)butanamide in place of 8-amino-N-((2S,3R,4R,5R)-2,3,4,5,6-pentahydroxyhexyl)octanamide, and was obtained as a colorless oil. ESI-MS m/z $[M+H]^+$ 677.3.

EXAMPLE 5

4-amino-5-chloro-2-methoxy-N-((3S,4R)-3-methoxy-1-(6-oxo-6-((2-oxo-2-(((2S,3R,4R,5R)-2,3,4,5,6-pentahydroxyhexyl)amino)ethyl)amino)hexyl)piperidin-4-yl)benzamide

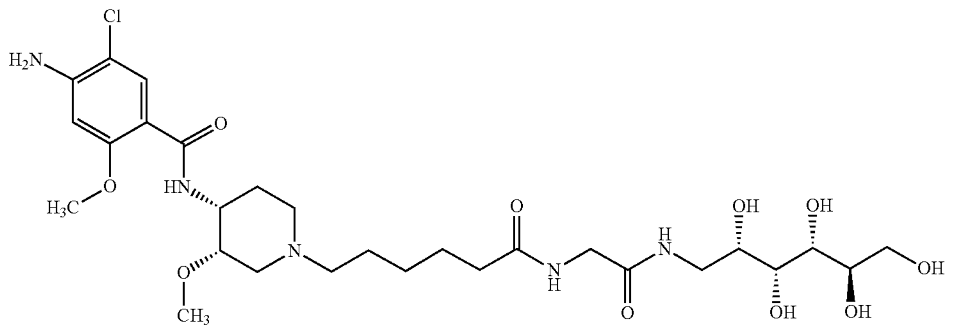 [SMILES: COc1cc(N)c(Cl)cc1C(=O)N[C@@H]1CCN(CCCCCC(=O)NCC(=O)NC[C@H](O)[C@@H](O)[C@H](O)[C@H](O)CO)C[C@@H]1OC]

The title compound was prepared like Example 2, using 2-amino-N-((2S,3R,4R,5R)-2,3,4,5,6-pentahydroxyhexyl)acetamide in place of 8-amino-N-((2S,3R,4R,5R)-2,3,4,5,6-pentahydroxyhexyl)octanamide, and was obtained as a colorless oil. ESI-MS m/z $[M+H]^+$ 649.2.

EXAMPLE 6

4-amino-5-chloro-2-methoxy-N-((3S,4R)-3-methoxy-1-((22S,23R,24R,25R)-22,23,24,25,26-pentahydroxy-6,19-dioxo-10,13,16-trioxa-7,20-diazahexacosyl)piperidin-4-yl)benzamide

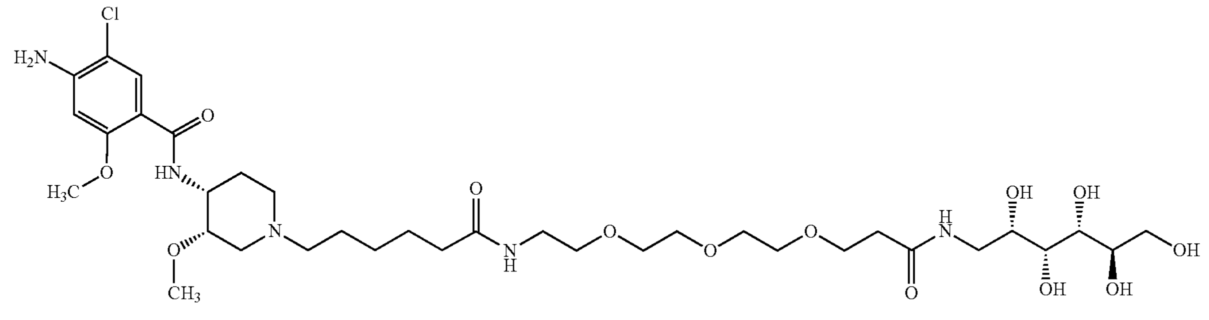 [SMILES: COc1cc(N)c(Cl)cc1C(=O)N[C@@H]1CCN(CCCCCC(=O)NCCOCCOCCOCCC(=O)NC[C@H](O)[C@@H](O)[C@H](O)[C@H](O)CO)C[C@@H]1OC]

The title compound was prepared like Example 2, using 3-(2-(2-(2-aminoethoxy)ethoxy)ethoxy)-N-((2S,3R,4R,5R)-2,3,4,5,6-pentahydroxyhexyl)propanamide in place of 8-amino-N-((2S,3R,4R,5R)-2,3,4,5,6-pentahydroxyhexyl)octanamide, and was obtained as a colorless oil. ESI-MS m/z $[M+H]^+$ 795.3.

EXAMPLE 7

4-amino-5-chloro-2-methoxy-N-((3S,4R)-3-methoxy-1-((19S,20R,21R,22R)-19,20,21,22,23-pentahydroxy-6,16-dioxo-10,13-dioxa-7,17-diazatricosyl)piperidin-4-yl)benzamide

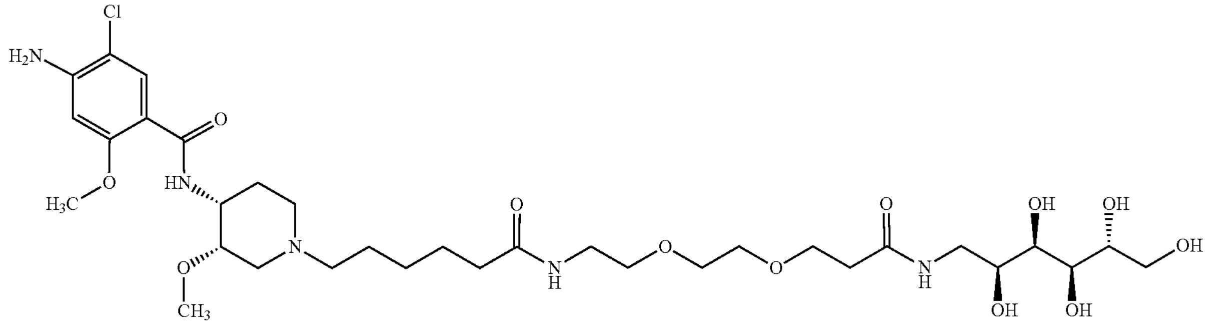 [SMILES: COc1cc(N)c(Cl)cc1C(=O)N[C@@H]1CCN(CCCCCC(=O)NCCOCCOCCC(=O)NC[C@H](O)[C@@H](O)[C@H](O)[C@H](O)CO)C[C@@H]1OC]

The title compound was prepared like Example 2, using 3-(2-(2-aminoethoxy)ethoxy)-N-((2S,3R,4R,5R)-2,3,4,5,6-pentahydroxyhexyl)propanamide in place of 8-amino-N-((2S,3R,4R,5R)-2,3,4,5,6-pentahydroxyhexyl)octanamide, and was obtained as a colorless oil. $^1H$ NMR (400 MHz, DMSO-$d_6$) δ ppm 8.13-8.17 (m, 1H), 8.09 (br d, J=7.9 Hz, 1H), 7.75-7.88 (m, 2H), 7.70-7.74 (m, 1H), 6.47-6.52 (m, 1H), 5.95-6.03 (m, 2H), 4.67-4.85 (m, 1H), 4.16-4.60 (m, 5H), 3.94-4.07 (m, 1H), 3.83-3.89 (m, 3H), 3.52-3.63 (m, 7H), 3.44-3.50 (m, 5H), 3.14-3.21 (m, 3H), 2.96-3.06 (m, 2H), 2.25-2.38 (m, 5H), 2.12-2.24 (m, 2H), 2.02-2.11 (m, 3H), 1.56-1.78 (m, 3H), 1.35-1.56 (m, 5H), 1.16-1.30 (m, 3H); ESI-MS m/z $[M+H]^+$ 750.8.

EXAMPLE 8

4-amino-5-chloro-2-methoxy-N-((3S,4R)-3-methoxy-1-(6-oxo-6-((1-(8-oxo-8-(((2S,3R,4R,5R)-2,3,4,5,6-pentahydroxyhexyl)amino)octyl)piperidin-4-yl)amino)hexyl)piperidin-4-yl)benzamide

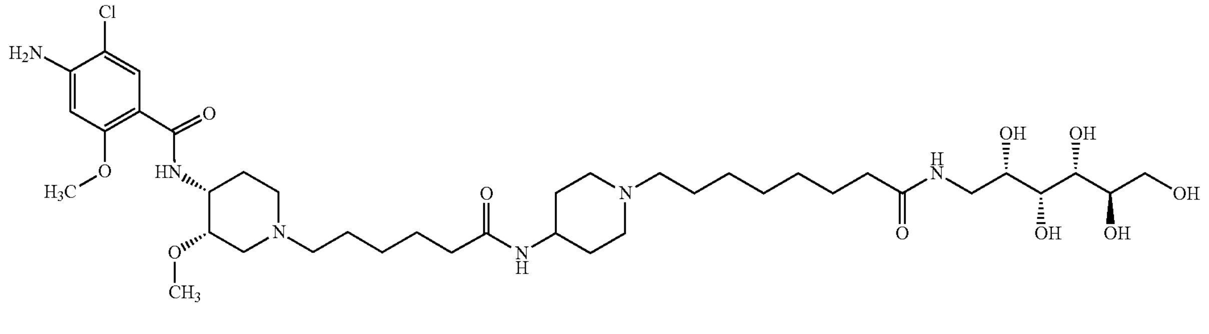 [SMILES: COc1cc(N)c(Cl)cc1C(=O)N[C@@H]1CCN(CCCCCC(=O)NC2CCN(CCCCCCCC(=O)NC[C@H](O)[C@@H](O)[C@H](O)[C@H](O)CO)CC2)C[C@@H]1OC]

To a solution of 8-(4-(6-((3S,4R)-4-(4-amino-5-chloro-2-methoxybenzamido)-3-methoxypiperidin-1-yl)hexanamido)piperidin-1-yl)octanoic acid (4.5 g, 6.90 mmol) in DMF (100 mL) were added HATU (5.25 g, 13.80 mmol), DIPEA (2.67 g, 20.70 mmol, 3.61 mL) and (2R,3R,4R,5S)-6-aminohexane-1,2,3,4,5-pentaol (3.75 g, 20.70 mmol). The mixture was stirred at 80° C. for 1 hour and then was diluted with $H_2O$ (5 mL), concentrated and purified by preparative HPLC (Kromasil Eternity XT, 250×80 mm, 10 μm) using a gradient (10 to 40%) of ACN/water (0.05% ammonia hydroxide). The title compound was obtained as a white solid (1199.28 mg, 99% purity). $^1H$ NMR (400 MHz, DMSO-$d_6$) δ ppm 7.84 (s, 1H), 6.51 (s, 1H), 4.10-4.00 (m, 1H), 3.93 (s, 3H), 3.75-3.50 (m, 7H), 3.50-3.40 (m, 5H), 3.25-3.05 (m, 2H), 3.00-2.60 (m, 3H), 2.50-2.25 (m, 4H), 2.25-2.00 (m, 8H), 2.00-1.70 (m, 4H), 1.70-1.45 (m, 10H), 1.40-1.20 (m, 8H); ESI-MS m/z $[M+H]^+$ 815.4.

EXAMPLE 9

4-amino-5-chloro-2-methoxy-N-((3S,4R)-3-methoxy-1-(6-oxo-6-((1-(6-oxo-6-(((2S,3R,4R,5R)-2,3,4,5,6-pentahydroxyhexyl)amino)hexyl)piperidin yl)amino)hexyl)piperidin-4-yl)benzamide

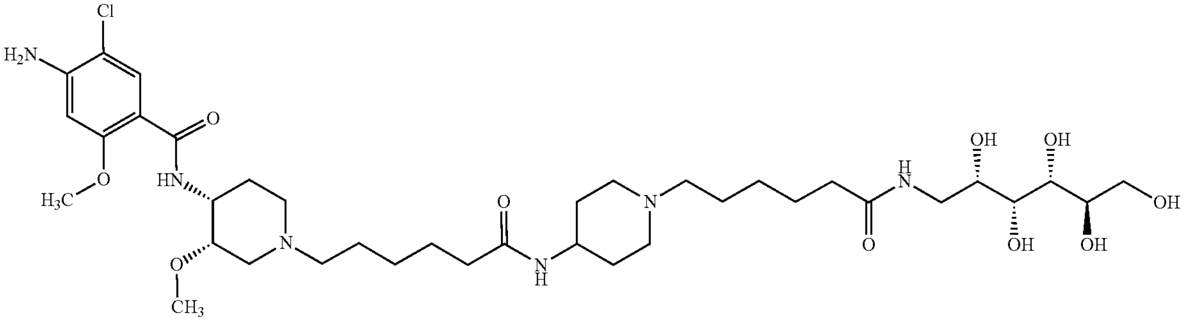 [SMILES: COc1cc(N)c(Cl)cc1C(=O)N[C@@H]1CCN(CCCCCC(=O)NC2CCN(CCCCCC(=O)NC[C@H](O)[C@@H](O)[C@H](O)[C@H](O)CO)CC2)C[C@@H]1OC]

The title compound was prepared like Example 8, using 6-(4-(6-((3S,4R)-4-(4-amino-5-chloro-2-methoxybenzamido)-3-methoxypiperidin-1-yl)hexanamido)piperidin-1-yl)hexanoic acid in place of 8-(4-(6-((3S,4R)-4-(4-amino-5-chloro-2-methoxybenzamido)-3-methoxypiperidin-1-yl) hexanamido)piperidin-1-yl)octanoic acid, and was obtained as a white solid. ESI-MS m/z $[M+H]^+$ 788.1.

EXAMPLE 10

4-amino-5-chloro-2-methoxy-N-((3S,4R)-3-methoxy-1-(6-(methyl(1-(8-oxo-8-(((2S,3R,4R,5R)-2,3,4,5,6-pentahydroxyhexyl)amino)octyl)piperidin-4-yl)amino)-6-oxohexyl)piperidin-4-yl)benzamide

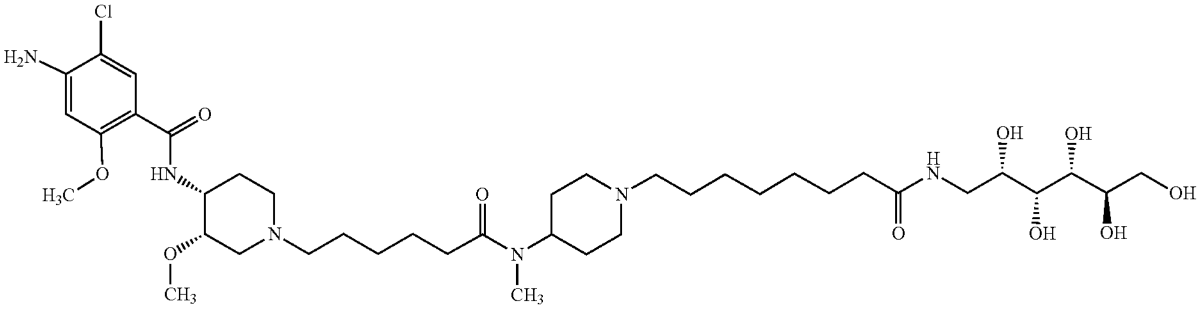 [SMILES: COc1cc(N)c(Cl)cc1C(=O)N[C@@H]1CCN(CCCCCC(=O)N(C)C2CCN(CCCCCCCC(=O)NC[C@H](O)[C@@H](O)[C@H](O)[C@H](O)CO)CC2)C[C@@H]1OC]

The title compound was prepared like Example 8, using 8-(4-(6-((3S,4R)-4-(4-amino-5-chloro-2-methoxybenzamido)-3-methoxypiperidin-1-yl)-N-methylhexanamido) piperidin-1-yl)octanoic acid in place of 8-(4-(6-((3S,4R)-4-(4-amino-5-chloro-2-methoxybenzamido)-3-methoxypiperidin-1-yl)hexanamido)piperidin-1-yl)octanoic acid, and was obtained as a white solid. $^1H$ NMR (400 MHz, DMSO-$d_6$) δ ppm 8.01-8.15 (m, 1H), 7.66-7.77 (m, 1H), 6.44-6.55 (m, 1H), 5.91-6.05 (m, 2H), 4.16-4.53 (m, 3H), 3.91-4.06 (m, 1H), 3.81-3.90 (m, 3H), 3.44-3.73 (m, 6H), 3.30 (s, 3H), 2.82-3.16 (m, 5H), 2.74-2.82 (m, 2H), 2.60-2.70 (m, 2H), 1.98-2.38 (m, 11H), 1.32-1.98 (m, 18H), 1.15-1.32 (m, 10H); ESI-MS m/z $[M+H]^+$ 830.0.

EXAMPLE 11

4-amino-5-chloro-2-methoxy-N-((3S,4R)-3-methoxy-1-(6-(methyl(1-(6-oxo-6-(((2S,3R,4R,5R)-2,3,4,5,6-pentahydroxyhexyl)amino)hexyl)piperidin yl)amino)-6-oxohexyl)piperidin-4-yl)benzamide

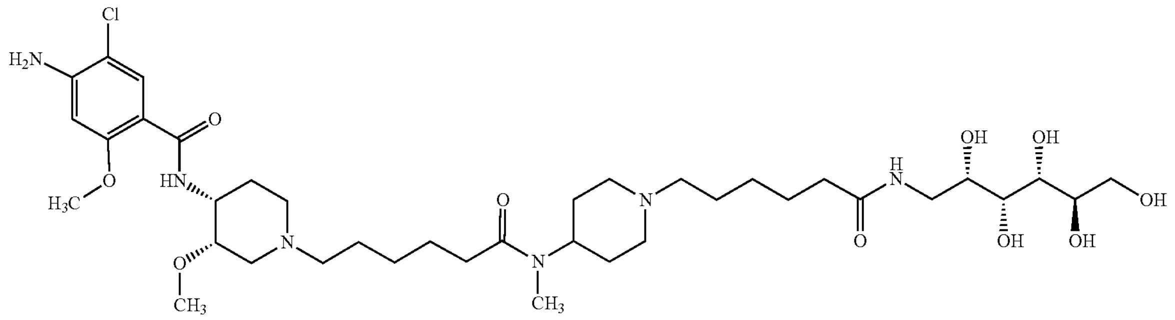 [SMILES: COc1cc(N)c(Cl)cc1C(=O)N[C@@H]1CCN(CCCCCC(=O)N(C)C2CCN(CCCCCC(=O)NC[C@H](O)[C@@H](O)[C@H](O)[C@H](O)CO)CC2)C[C@@H]1OC]

The title compound was prepared like Example 8, using 6-(4-(6-((3S,4R)-4-(4-amino-5-chloro-2-methoxybenzamido)-3-methoxypiperidin-1-yl)-N-methylhexanamido)piperidin-1-yl)hexanoic acid in place of 8-(4-(6-((3S,4R)-4-(4-amino-5-chloro-2-methoxybenzamido)-3-methoxypiperidin-1-yl)hexanamido)piperidin-1-yl)octanoic acid, and was obtained as a white solid. ESI-MS m/z $[M+H]^+$ 802.0.

EXAMPLE 12

4-amino-5-chloro-2-methoxy-N-((3S,4R)-3-methoxy-1-(6-oxo-6-(((R)-1-(8-oxo-8-(((2S,3R,4R,5R)-2,3,4,5,6-pentahydroxyhexyl)amino)octyl)piperidin-3-yl)amino)hexyl)piperidin-4-yl)benzamide

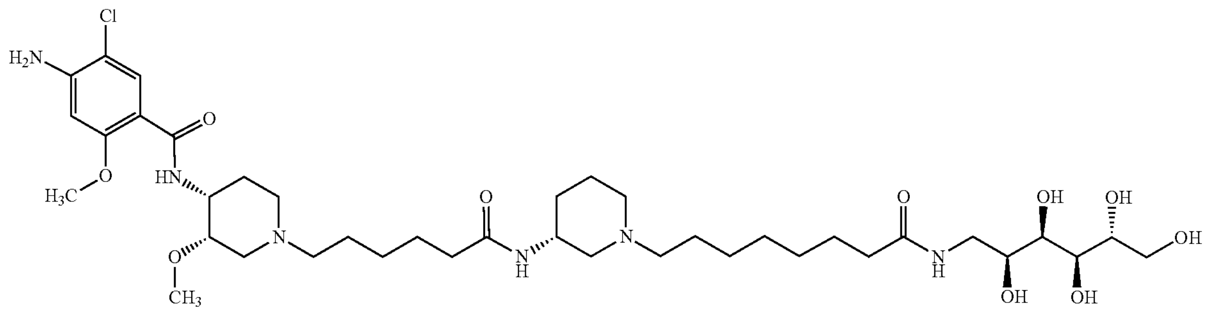 [SMILES: COc1cc(N)c(Cl)cc1C(=O)N[C@@H]1CCN(CCCCCC(=O)N[C@@H]2CCCN(CCCCCCCC(=O)NC[C@H](O)[C@@H](O)[C@H](O)[C@H](O)CO)C2)C[C@@H]1OC]

The title compound was prepared like Example 8, using 8-(((R)-3-(6-(((3S,4R)-4-(4-amino-5-chloro-2-methoxybenzamido)-3-methoxypiperidin-1-yl)hexanamido)piperidin-1-yl)octanoic acid in place of 8-(4-(6-((3S,4R)-4-(4-amino-5-chloro-2-methoxybenzamido)-3-methoxypiperidin-1-yl)hexanamido)piperidin-1-yl)octanoic acid, and was obtained as a white solid. ESI-MS m/z $[M+H]^+$ 816.3.

EXAMPLE 13

4-amino-5-chloro-2-methoxy-N-((3S,4R)-3-methoxy-1-(6-oxo-6-(((R)-1-(6-oxo-6-(((2S,3R,4R,5R)-2,3,4,5,6-pentahydroxyhexyl)amino)hexyl)piperidin-3-yl)amino)hexyl)piperidin-4-yl)benzamide

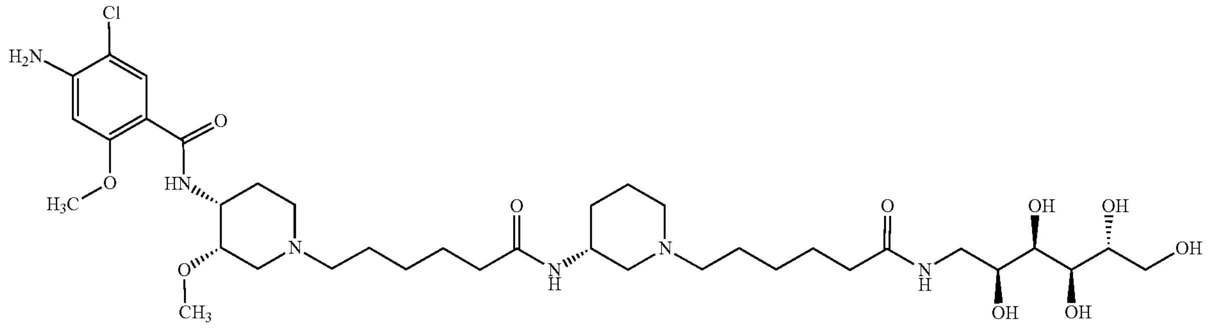 [SMILES: COc1cc(N)c(Cl)cc1C(=O)N[C@@H]1CCN(CCCCCC(=O)N[C@@H]2CCCN(CCCCCC(=O)NC[C@H](O)[C@@H](O)[C@H](O)[C@H](O)CO)C2)C[C@@H]1OC]

The title compound was prepared like Example 8, using 6-((R)-3-(6-((3S,4R)-4-(4-amino-5-chloro-2-methoxybenzamido)-3-methoxypiperidin-1-yl)hexanamido)piperidin-1-yl)hexanoic acid in place of 8-(4-(6-((3S,4R)-4-(4-amino-5-chloro-2-methoxybenzamido)-3-methoxypiperidin-1-yl)hexanamido)piperidin-1-yl)octanoic acid, and was obtained as a white solid. ESI-MS m/z $[M+H]^+$ 788.1.

EXAMPLE 14

4-amino-5-chloro-2-methoxy-N-((3S,4R)-3-methoxy-1-(6-(methyl((R)-1-(8-oxo-8-(((2S,3R,4R,5R)-2,3,4,5,6-pentahydroxyhexyl)amino)octyl)piperidin-3-yl)amino)-6-oxohexyl)piperidin-4-yl)benzamide

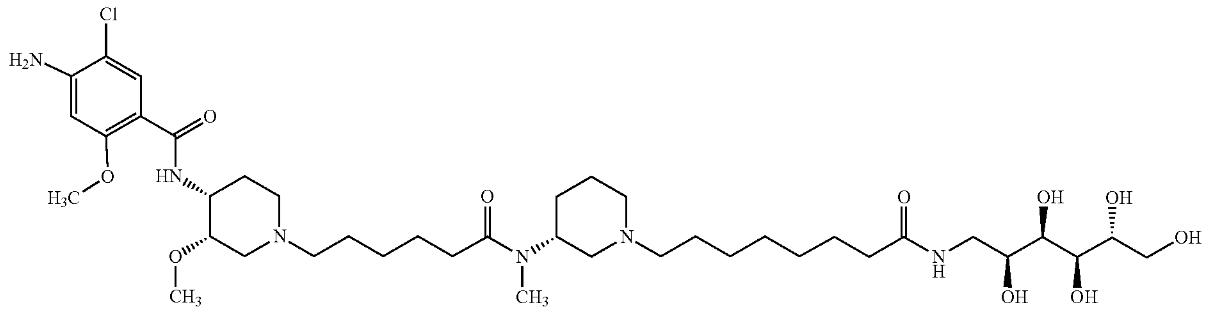 [SMILES: COc1cc(N)c(Cl)cc1C(=O)N[C@@H]1CCN(CCCCCC(=O)N(C)[C@@H]2CCCN(CCCCCCCC(=O)NC[C@H](O)[C@@H](O)[C@H](O)[C@H](O)CO)C2)C[C@@H]1OC]

The title compound was prepared like Example 8, using 8-((R)-3-(6-((3S,4R)-4-(4-amino-5-chloro-2-methoxybenzamido)-3-methoxypiperidin-1-yl)-N-methylhexanamido)piperidin-1-yl)octanoic acid in place of 8-(4-(6-((3S,4R)-4-(4-amino-5-chloro-2-methoxybenzamido)-3-methoxypiperidin-1-yl)hexanamido)piperidin-1-yl)octanoic acid, and was obtained as a white solid. ESI-MS m/z $[M+H]^+$ 830.1.

EXAMPLE 15

4-amino-5-chloro-2-methoxy-N-((3S,4R)-3-methoxy-1-(6-(methyl((R)-1-(6-oxo-6-(((2S,3R,4R,5R)-2,3,4,5,6-pentahydroxyhexyl)amino)hexyl)piperidin-3-yl)amino)-6-oxohexyl)piperidin-4-yl)benzamide

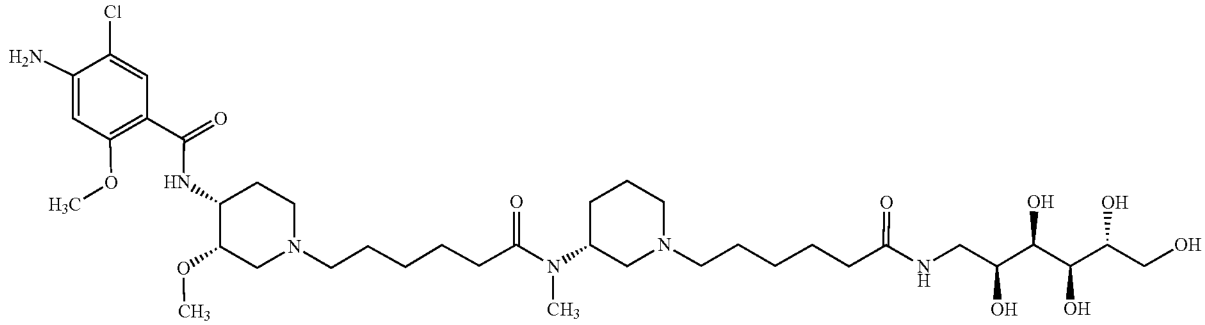 [SMILES: COc1cc(N)c(Cl)cc1C(=O)N[C@@H]1CCN(CCCCCC(=O)N(C)[C@@H]2CCCN(CCCCCC(=O)NC[C@H](O)[C@@H](O)[C@H](O)[C@H](O)CO)C2)C[C@@H]1OC]

The title compound was prepared like Example 8, using 6-((R)-3-(6-((3S,4R)-4-(4-amino-5-chloro-2-methoxybenzamido)-3-methoxypiperidin-1-yl)-N-methylhexanamido)piperidin-1-yl)hexanoic acid in place of 8-(4-(6-((3S,4R)-4-(4-amino-5-chloro-2-methoxybenzamido)-3-methoxypiperidin-1-yl)hexanamido)piperidin-1-yl)octanoic acid, and was obtained as a white solid. ESI-MS m/z $[M+H]^+$ 802.1.

EXAMPLE 16

4-amino-5-chloro-2-methoxy-N-((3S,4R)-3-methoxy-1-(6-(methyl(8-oxo-8-(((2S,3R,4R,5R)-2,3,4,5,6-pentahydroxyhexyl)amino)octyl)amino)-6-oxohexyl)piperidin-4-yl)benzamide

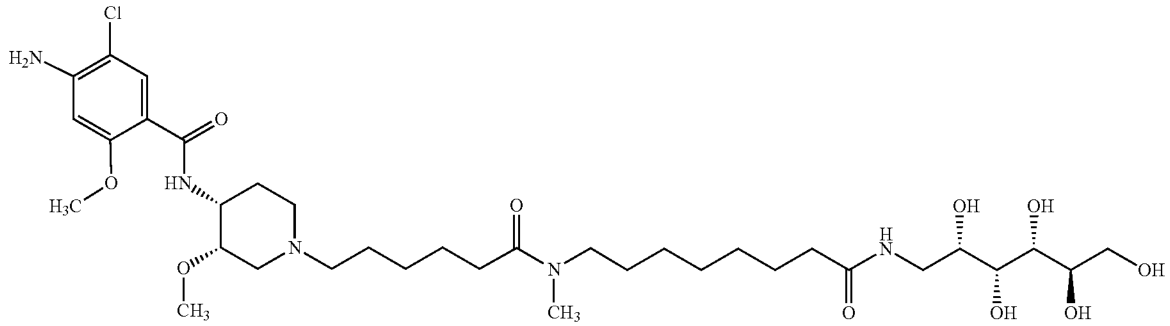 [SMILES: COc1cc(N)c(Cl)cc1C(=O)N[C@@H]1CCN(CCCCCC(=O)N(C)CCCCCCCC(=O)NC[C@H](O)[C@@H](O)[C@H](O)[C@H](O)CO)C[C@@H]1OC]

To a mixture of 8-(6-((3S,4R)-4-(4-amino-5-chloro-2-methoxybenzamido)-3-methoxypiperidin-1-yl)-N-methylhexanamido)octanoic acid (90 mg, 152.17 μmol, Preparation 31) and (2R,3R,4R,5S)-6-aminohexane-1,2,3,4,5-pentaol (55.14 mg, 304.34 μmol) in DMF (5 mL) were added HATU (115.72 mg, 304.34 μmol) and DIPEA (59.00 mg, 456.51 μmol, 79.52 The mixture was stirred at 70° C. for 2 hours and then was concentrated and purified by preparative HPLC (Phenomenex Synergi, C-18, 150×25 mm, 10 μm) using a gradient (10 to 40%) of ACN/water (0.1% TFA). The pure fractions were lyophilized to give the title compound as a yellow gum (52 mg, 45% yield, 98.17% purity). $^1H$ NMR (400 MHz, DMSO-$d_6$) δ ppm 7.85 (s, 1H), 6.53 (s, 1H), 4.28-4.22 (m, 1H), 3.95 (s, 3H), 3.93-3.85 (m, 1H), 3.81-3.73 (m, 3H), 3.74-3.65 (m, 2H), 3.64-3.60 (m, 2H), 3.58 (s, 3H), 3.56-3.48 (m, 1H), 3.47-3.42 (m, 1H), 3.40-3.33 (m, 2H), 3.27-3.20 (m, 1H), 3.19-3.10 (m, 4H), 3.04 (s, 2H), 2.91 (s, 1H), 2.45-2.40 (m, 2H), 2.25-2.18 (m, 2H), 2.10-2.01 (m, 2H), 1.85-1.47 (m, 8H), 1.46-1.29 (m, 8H); ESI-MS m/z $[M+H]^+$ 746.5.

EXAMPLE 17

4-amino-5-chloro-2-methoxy-N-((3S,4R)-3-methoxy-1-(2-(3-oxo ((8-oxo-8-(((2S,3R,4R,5R)-2,3,4,5,6-pentahydroxyhexyl)amino)octyl)amino)propoxy)ethyl)piperidin-4-yl)benzamide

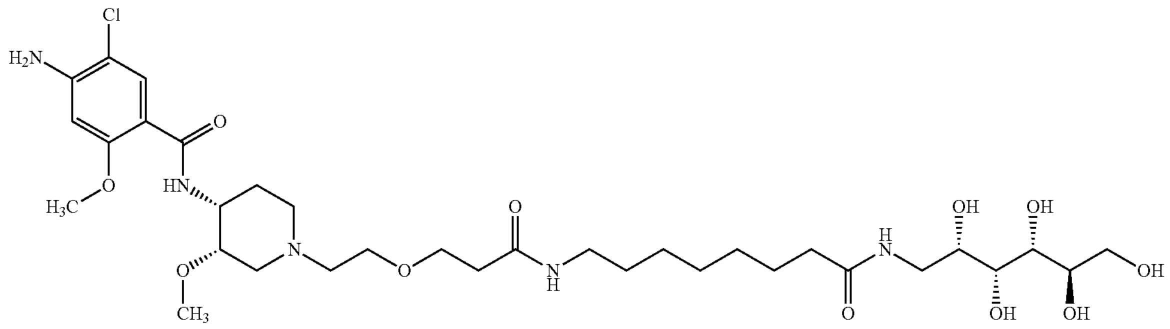 [SMILES: COc1cc(N)c(Cl)cc1C(=O)N[C@@H]1CCN(CCOCCC(=O)NCCCCCCCC(=O)NC[C@H](O)[C@@H](O)[C@H](O)[C@H](O)CO)C[C@@H]1OC]

The title compound was prepared like Example 2, using 3-(2-((3S,4R)-4-(4-amino-5-chloro-2-methoxybenzamido)-3-methoxypiperidin-1-yl)ethoxy)propanoic acid (prepared from 4-amino-5-chloro-2-methoxy-N-((3S,4R)-3-methoxypiperidin-4-yl)benzamide and tert-butyl 3-(2-(tosyloxy)ethoxy)propanoate) in place of 6-((3S,4R)-4-(4-amino-5-chloro-2-methoxybenzamido)-3-methoxypiperidin-1-yl)hexanoic acid, and was obtained as a yellow solid. $^1$H NMR (400 MHz, DMSO-$d_6$) δ ppm 7.58 (s, 1H), 6.54 (s, 1H), 4.27-4.26 (m, 1H), 3.95-3.76 (m, 5H), 3.66-3.54 (m, 10H), 3.33-3.30 (m, 6H), 3.29-3.20 (m, 6H), 2.50 (t, J=5.2 Hz, 2H), 2.21-2.16 (m, 4H), 1.58-1.51 (m, 4H), 1.33 (br s, 6H); ESI-MS m/z [M+H]$^+$ 734.4.

EXAMPLE 18

4-amino-5-chloro-2-methoxy-N-((3S,4R)-3-methoxy-1-(7-oxo-7-((8-oxo-8-(((2S,3R,4R,5R)-2,3,4,5,6-pentahydroxyhexyl)amino)octyl)amino)heptan-2-yl)piperidin-4-yl)benzamide

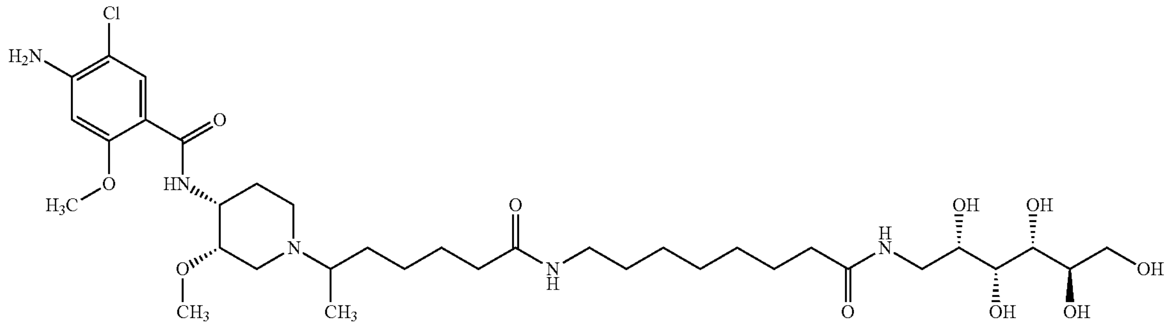 [SMILES: COc1cc(N)c(Cl)cc1C(=O)N[C@@H]1CCN(C(C)CCCCC(=O)NCCCCCCCC(=O)NC[C@H](O)[C@@H](O)[C@H](O)[C@H](O)CO)C[C@@H]1OC]

The title compound was prepared like Example 2, using 6-((3S,4R)-4-(4-amino-5-chloro-2-methoxybenzamido)-3-methoxypiperidin-1-yl)heptanoic acid in place of 6-((3S,4R)-4-(4-amino-5-chloro-2-methoxybenzamido)-3-methoxypiperidin-1-yl)hexanoic acid, and was obtained as a yellow solid. $^1$H NMR (400 MHz, DMSO-$d_6$) δ ppm 7.86 (s, 1H), 6.55 (s, 1H), 4.21-4.33 (m, 1H), 3.96 (s, 3H), 3.74-3.86 (m, 5H), 3.60-3.74 (m, 4H), 3.59 (s, 3H), 3.43-3.50 (m, 1H), 3.35-3.40 (m, 2H), 3.16-3.30 (m, 4H), 2.20-2.28 (m, 4H), 2.07-2.17 (m, 2H), 1.58-1.83 (m, 6H), 1.48-1.56 (m, 3H), 1.33-1.43 (m, 11H);); ESI-MS m/z [M+H]$^+$ 746.4.

EXAMPLE 19

4-amino-5-chloro-2-methoxy-N-((3S,4R)-3-methoxy-1-(2-methyl oxo-6-((8-oxo-8-(((2S,3R,4R,5R)-2,3,4,5,6-pentahydroxyhexyl)amino)octyl)amino)hexyl)piperidin-4-yl)benzamide

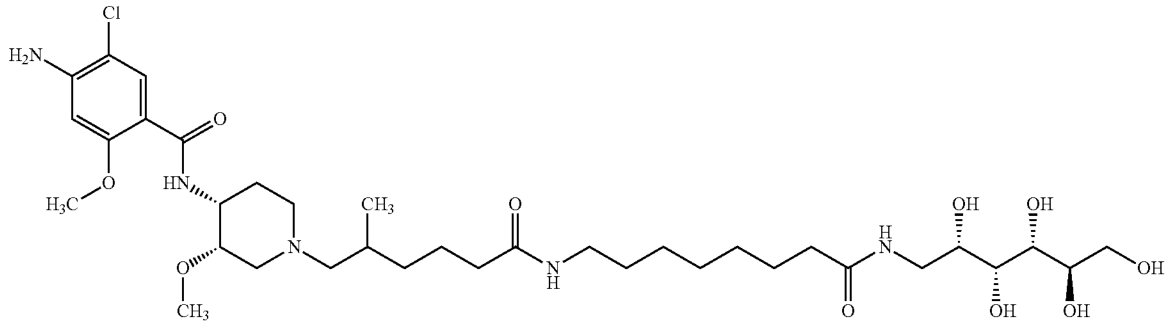 [SMILES: COc1cc(N)c(Cl)cc1C(=O)N[C@@H]1CCN(CC(C)CCCC(=O)NCCCCCCCC(=O)NC[C@H](O)[C@@H](O)[C@H](O)[C@H](O)CO)C[C@@H]1OC]

A mixture of 8-(6-((3S,4R)-4-(4-amino-5-chloro-2-methoxybenzamido)-3-methoxypiperidin-1-yl)-5-methylhexanamido)octanoic acid (150 mg, 257.22 μmol, Preparation 43), (2R,3R,4R,5S)-6-aminohexane-1,2,3,4,5-pentaol (69.91 mg, 385.83 μmol), DIPEA (99.73 mg, 771.66 μmol, 134.41 HOBt (52.13 mg, 385.83 μmol) and EDCI (73.96 mg, 385.83 μmol) in DMF (3 mL) was degassed and purged with $N_2$ 3 times and then stirred at 30° C. for 14 hours under $N_2$ atmosphere. LCMS showed about 8% of the starting material remained and m/z of the desired product was detected, and TLC (DCM/MeOH=10:1) indicated the starting material was present and a new spot was formed. The reaction mixture was purified by preparative HPLC (Phenomenex Synergi C-18, 150×25 mm, 10 μm) using a gradient (8 to 38%) of ACN/water (0.1% TFA) to give a TFA salt of the title compound as a yellow solid (40 mg, 18% yield, 96.70% purity). $^1$H NMR (400 MHz, $CD_3OD$) δ ppm 7.87 (s, 1H), 6.55 (s, 1H), 4.29-4.26 (m, 1H), 3.93-3.90 (m, 1H), 3.85-3.78 (m, 3H), 3.75-3.70 (m, 2H), 3.64-3.66 (m, 1H), 3.65-3.62 (m, 1H), 3.61-3.60 (m, 3H), 3.50-3.45 (m, 2H), 3.21-3.16 (m, 8H), 2.25-2.05 (m, 8H), 1.76-1.45 (m, 7H), 1.42-1.20 (m, 7H), 3.91-3.84 (m, 2H), 3.59-3.42 (m, 2H), 1.08 (d, J=6.4 Hz, 3H); ESI-MS m/z $[M+H]^+$ 746.3.

EXAMPLE 20

4-amino-5-chloro-2-methoxy-N-((3S,4R)-3-methoxy-1-(3-methyl-6-oxo-6-((8-oxo-8-(((2S,3R,4R,5R)-2,3,4,5,6-pentahydroxyhexyl)amino)octyl)amino)hexyl)piperidin-4-yl)benzamide

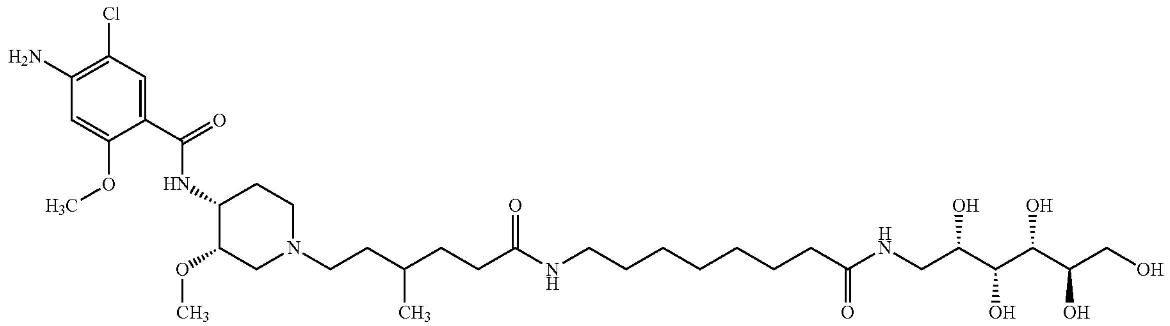 [SMILES: COc1cc(N)c(Cl)cc1C(=O)N[C@@H]1CCN(CCC(C)CCC(=O)NCCCCCCCC(=O)NC[C@H](O)[C@@H](O)[C@H](O)[C@H](O)CO)C[C@@H]1OC]

To a solution of 8-(6-((3S,4R)-4-(4-amino-5-chloro-2-methoxybenzamido)-3-methoxypiperidin-1-yl)-4-methylhexanamido)octanoic acid (550 mg, 943.14 μmol, Preparation 52) in DMF (2 mL) were added EDCI (271.20 mg, 1.41 mmol), HOBt (191.16 mg, 1.41 mmol), DIPEA (365.68 mg, 2.83 mmol, 492.83 μL) and (2R,3R,4R,5S)-6-aminohexane-1,2,34,5-pentaol (170.88 mg, 943.14 μmol). The mixture was stirred at 30° C. for 5 hours and then was diluted with $H_2O$ (50 mL) and extracted with EtOAc (50 mL×3). The combined organic layers were washed with brine (100 mL×2), dried over anhydrous $Na_2SO_4$, filtered and concentrated under reduced pressure. The residue was purified by preparative HPLC (Boston Prime C-18, 150×30 mm, 5 μm) using a gradient (20 to 40%) of ACN/water (0.1% TFA) to give a TFA salt of the title compound as a yellow solid (26.52 mg, 3.24% yield, 99.1% purity). $^1H$ NMR (400 MHz, $CD_3OD$) δ ppm 7.89 (s, 1H), 6.57 (s, 1H), 4.25-4.33 (m, 1H), 3.98 (s, 3H), 3.93 (br d, J=14.2 Hz, 1H), 3.76-3.88 (m, 4H), 3.71-3.76 (m, 1H), 3.68-3.70 (m, 1H), 3.64-3.68 (m, 1H), 3.61 (d, J=1.0 Hz, 3H), 3.56 (br s, 1H), 3.49 (dd, J=13.6, 4.9 Hz, 1H), 3.28-3.33 (m, 1H), 3.27 (br s, 1H), 3.18-3.24 (m, 5H), 2.28-2.36 (m, 1H), 2.25 (t, J=7.6 Hz, 3H), 2.05-2.15 (m, 2H), 1.45-1.89 (m, 10H), 1.38 (br s, 6H), 1.04 (d, J=6.4 Hz, 3H); ESI-MS m/z $[M+H]^+$ 745.3.

EXAMPLE 21

4-amino-5-chloro-2-methoxy-N-((3S,4R)-3-methoxy-1-(4-methyl-6-oxo-6-((8-oxo-8-(((2S,3R,4R,5R)-2,3,4,5,6-pentahydroxyhexyl)amino)octyl)amino)hexyl)piperidin-4-yl)benzamide

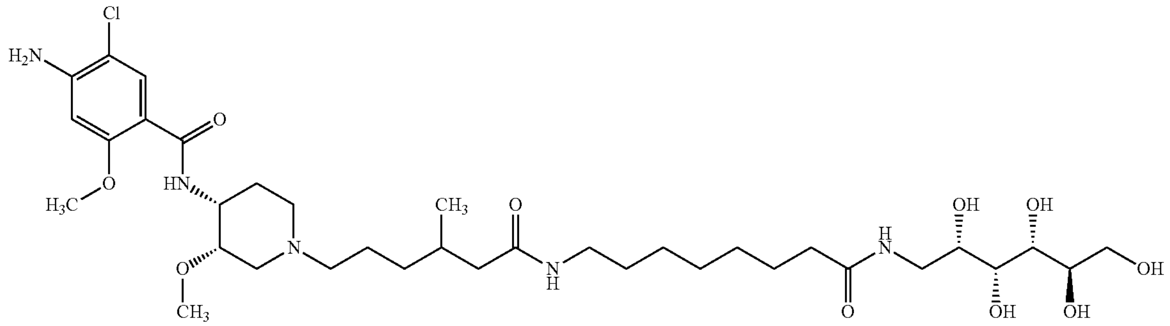 [SMILES: COc1cc(N)c(Cl)cc1C(=O)N[C@@H]1CCN(CCCC(C)CC(=O)NCCCCCCCC(=O)NC[C@H](O)[C@@H](O)[C@H](O)[C@H](O)CO)C[C@@H]1OC]

A mixture of 8-(6-((3S,4R)-4-(4-amino-5-chloro-2-methoxybenzamido) methoxypiperidin-1-yl)-3-methylhexanamido)octanoic acid (700 mg, 1.20 mmol, Preparation 61), (2R,3R,4R,5S)-6-aminohexane-1,2,3,4,5-pentaol (652.47 mg, 3.60 mmol), HATU (912.83 mg, 2.40 mmol) and DIPEA (465.41 mg, 3.60 mmol, 627.24 μL) in DMF (15 mL) was stirred at 80° C. for 0.5 hours. The reaction mixture was then diluted with $H_2O$ (5 mL), concentrated and purified by preparative HPLC (Kromasil Eternity XT, 250×80 mm, 10 μm) using a gradient (15 to 45%) of ACN/water (0.05% $NH_4OH$). The title compound was obtained as a white solid (140.91 mg, 98% purity). $^1H$ NMR (400 MHz, $CD_3OD$) δ ppm 7.85 (s, 1H), 6.52 (s, 1H), 4.58 (s, 1H), 4.31-4.00 (m, 1H), 4.94 (s, 3H), 3.76-3.56 (m, 6H), 3.54-3.36 (m, 5H), 3.29-3.08 (m, 4H), 2.85-2.70 (m, 1H), 2.46-2.29 (m, 2H), 2.28-2.15 (m, 5H), 2.08-1.78 (m, 4H), 1.68-1.45 (m, 5H), 1.34 (s, 7H), 1.27-1.09 (m, 1H), 0.94 (d, J=6.0 Hz, 3H); ESI-MS m/z $[M+H]^+$ 746.7.

EXAMPLE 22

4-amino-5-chloro-N-((3 S,4R)-1-(6-((8-((2-hydroxyethyl)((2S,3R,4R,5R)-2,3,4,5,6-pentahydroxyhexyl)amino)-8-oxooctyl)amino)-6-oxohexyl)-3-methoxypiperidin-4-yl)-2-methoxybenzamide

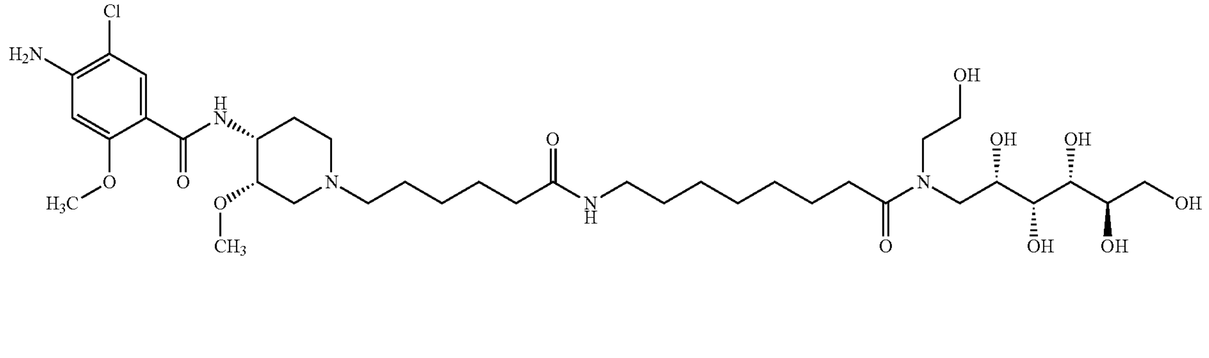 [SMILES: COc1cc(N)c(Cl)cc1C(=O)N[C@@H]1CCN(CCCCCC(=O)NCCCCCCCC(=O)N(CCO)C[C@H](O)[C@@H](O)[C@H](O)[C@H](O)CO)C[C@@H]1OC]

The title compound was prepared like Example 2, using 8-amino-N-(2-hydroxyethyl)-N-((2S,3R,4R,5R)-2,3,4,5,6-pentahydroxyhexyl)octanamide in place of 8-amino-N-((2S,3R,4R,5R)-2,3,4,5,6-pentahydroxyhexyl)octanamide, and was obtained as a white solid. ESI-MS m/z $[M+H]^+$ 777.3.

EXAMPLE 23

2-(8-(6-((3S,4R)-4-(4-amino-5-chloro-2-methoxy-benzamido)-3-methoxypiperidin-1-yl)hexanamido)octanamido)ethane-1-sulfonic acid

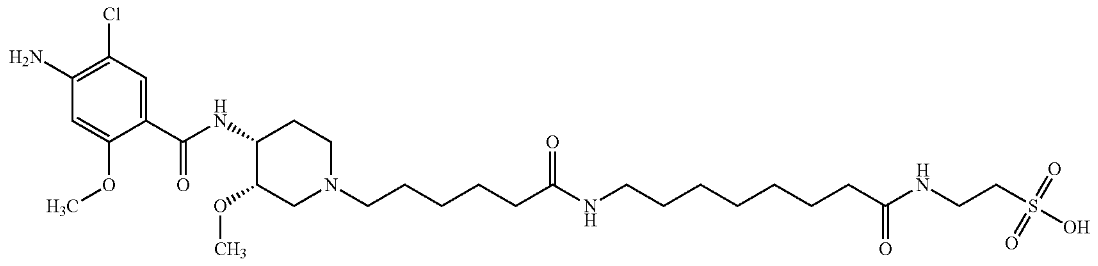 [SMILES: COc1cc(N)c(Cl)cc1C(=O)N[C@@H]1CCN(CCCCCC(=O)NCCCCCCCC(=O)NCCS(=O)(=O)O)C[C@@H]1OC]

The title compound was prepared like Example 2, using 2-(8-aminooctanamido)ethane-1-sulfonic acid in place of 8-amino-N-((2S,3R,4R,5R)-2,3,4,5,6-pentahydroxyhexyl)octanamide, and was obtained as a tan solid. ESI-MS m/z $[M+H]^+$ 677.3.

EXAMPLE 24

4-amino-5-chloro-2-methoxy-N-((3S,4R)-3-methoxy-1-(6-oxo ((8-oxo-8-(((1S,2S,3R,4S,5S)-2,3,4,5-tetrahydroxy (hydroxymethyl)cyclohexyl)amino)octyl)amino)hexyl)piperidin-4-yl)benzamide

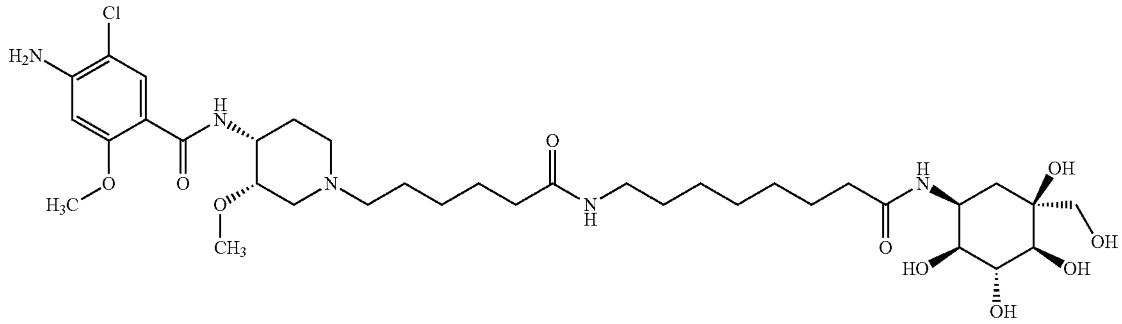 [SMILES: COc1cc(N)c(Cl)cc1C(=O)N[C@@H]1CCN(CCCCCC(=O)NCCCCCCCC(=O)N[C@H]2C[C@](O)(CO)[C@@H](O)[C@H](O)[C@H]2O)C[C@@H]1OC]

The title compound was prepared like Example 2, using 8-amino-N-((1S,2S,3R,4S,5S)-2,3,4,5-tetrahydroxy-5-(hydroxymethyl)cyclohexyl)octanamide in place of 8-amino-N-((2S,3R,4R,5R)-2,3,4,5,6-pentahydroxyhexyl)octanamide, and was obtained as a yellow solid. ESI-MS m/z $[M+H]^+$ 745.3.

EXAMPLE 25

(2-(8-(6-((3S,4R)-4-(4-amino-5-chloro-2-methoxy-benzamido)-3-methoxypiperidin-1-yl)hexanamido) octanamido)ethyl)phosphonic acid

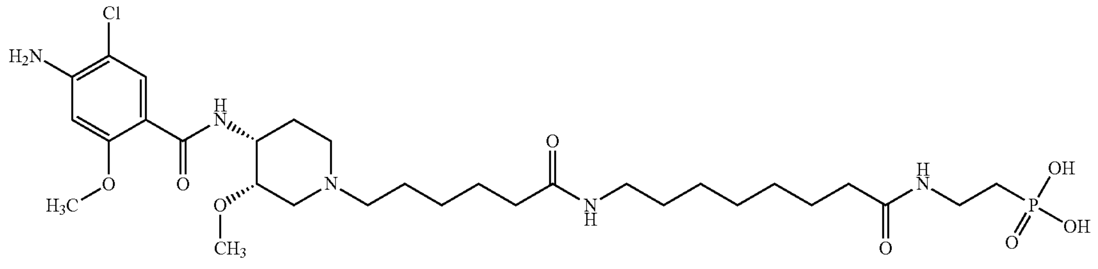 [SMILES: COc1cc(N)c(Cl)cc1C(=O)N[C@@H]1CCN(CCCCCC(=O)NCCCCCCCC(=O)NCCP(=O)(O)O)C[C@@H]1OC]

The title compound was prepared like Example 2, using (2-(8-aminooctanamido)ethyl)phosphonic acid in place of 8-amino-N-((2S,3R,4R,5R)-2,3,4,5,6-pentahydroxyhexyl) octanamide, and was obtained as a white solid. ESI-MS m/z $[M+H]^+$ 677.0.

EXAMPLE 26

(2-(8-(6-((3S,4R)-4-(4-amino-5-chloro-2-methoxy-benzamido)-3-methoxypiperidin-1-yl)hexanamido)-N-((2S,3R,4R,5R)-2,3,4,5,6-pentahydroxyhexyl) octanamido)ethyl)phosphonic acid

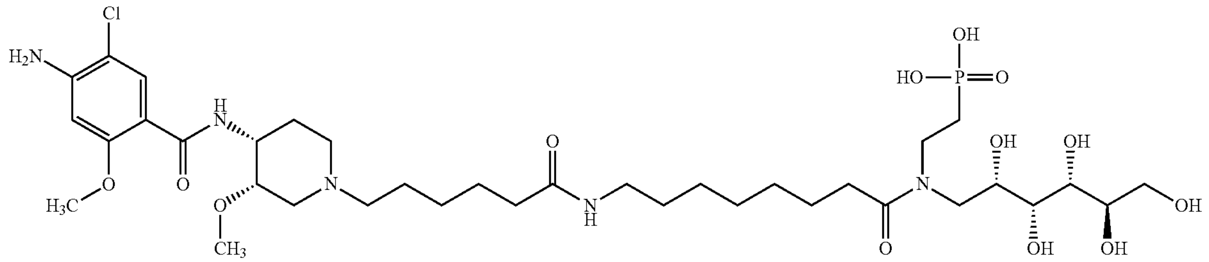 [SMILES: COc1cc(N)c(Cl)cc1C(=O)N[C@@H]1CCN(CCCCCC(=O)NCCCCCCCC(=O)N(CCP(=O)(O)O)C[C@H](O)[C@@H](O)[C@H](O)[C@H](O)CO)C[C@@H]1OC]

The title compound was prepared like Example 2, using (2-(8-amino-N-((2S,3R,4R,5R)-2,3,4,5,6-pentahydroxy-hexyl)octanamido)ethyl)phosphonic acid in place of 8-amino-N-((2S,3R,4R,5R)-2,3,4,5,6-pentahydroxyhexyl) octanamide, and was obtained as a white solid. ESI-MS m/z $[M+H]^+$ 841.3.

EXAMPLE 27

2-(8-(6-((3S,4R)-4-(4-amino-5-chloro-2-methoxy-benzamido) methoxypiperidin-1-yl)hexanamido)-N-(3-(dimethylamino)propyl)octanamido)ethane-1-sulfonic acid

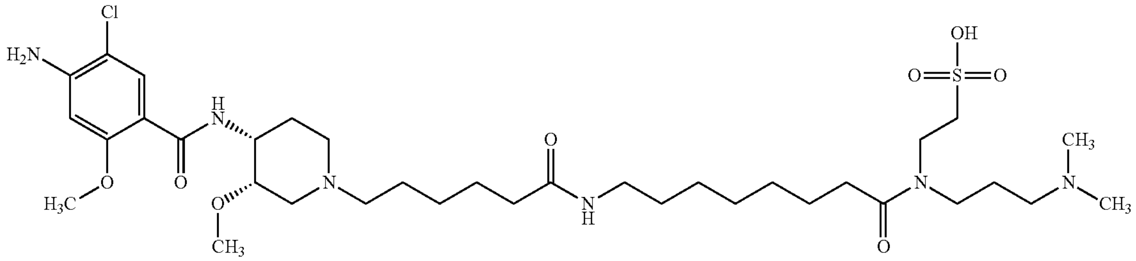 [SMILES: COc1cc(N)c(Cl)cc1C(=O)N[C@@H]1CCN(CCCCCC(=O)NCCCCCCCC(=O)N(CCCN(C)C)CCS(=O)(=O)O)C[C@@H]1OC]

The title compound was prepared like Example 2, using 2-(8-amino-N-(3-(dimethylamino)propyl)octanamido)ethane-1-sulfonic acid in place of 8-amino-N-((2S,3R,4R,5R)-2,3,4,5,6-pentahydroxyhexyl)octanamide, and was obtained as a white solid. ESI-MS m/z $[M+H]^+$ 762.1.

EXAMPLE 28

4-amino-5-chloro-N-(1-(6-oxo-6-(((R)-1-(8-oxo-8-(((2S,3R,4R,5R)-2,3,4,5,6-pentahydroxyhexyl)amino)octyl)piperidin-3-yl)amino)hexyl)piperidin-4-yl)-2,3-dihydrobenzofuran-7-carboxamide

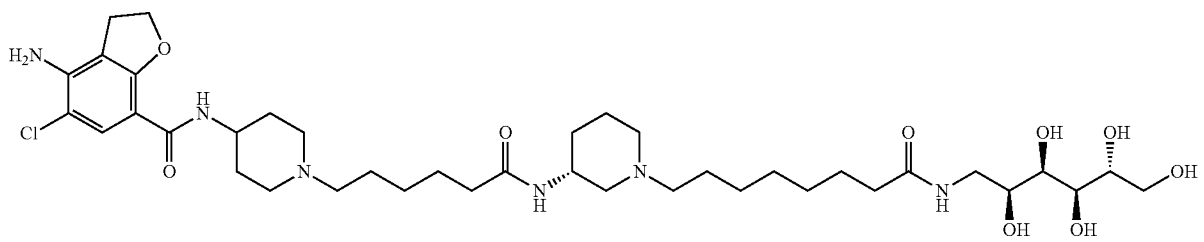 [SMILES: Nc1c(Cl)cc(C(=O)NC2CCN(CCCCCC(=O)N[C@@H]3CCCN(CCCCCCCC(=O)NC[C@H](O)[C@@H](O)[C@H](O)[C@H](O)CO)C3)CC2)c2c1CCO2]

A mixture of (R)-8-(3-(6-(4-(4-amino-5-chloro-2,3-dihydrobenzofuran-7-carboxamido)piperidin-1-yl)hexanamido)piperidin-1-yl)octanoic acid (460 mg, 725.27 μmol, Preparation 65), (2R,3R,4R,5S)-6-aminohexane-1,2,3,4,5-pentaol (417.88 mg, 2.31 mmol),T3P (939.80 mg, 1.48 mmol, 878.32 50%) and DIPEA (187.47 mg, 1.45 mmol, 252.65 μL) in DMF (10 mL) was stirred at 80° C. for 2 hours. The reaction mixture was then quenched with $H_2O$ (3 mL), concentrated and purified by preparative HPLC (Waters Xbridge 150×25 mm, 5 μm) using a gradient (20 to 50%) of ACN/water (0.05% $NH_4OH$). The title compound was obtained as a white solid (75.9 mg, 99% purity). $^1H$ NMR (400 MHz, DMSO-$d_6$) δ ppm 7.60 (s, 1H), 4.80 (t, J=8.8 Hz, 3H), 3.91-3.80 (m, 2H), 3.80-3.55 (m, 6H), 3.50-3.40 (m, 1H), 3.25-3.21 (m, 1H), 3.10 (t, J=8.8 Hz, 2H), 3.02-2.85 (m, 3H), 2.82-2.70 (m, 1H), 2.50-2.15 (m, 10H), 2.13-2.05 (m, 1H), 2.04-1.71 (m, 5H), 1.68-1.43 (m, 11H), 1.40-1.24 (m, 9H); ESI-MS m/z $[M+H]^+$ 797.5.

EXAMPLE 29

4-amino-5-chloro-N-(1-(6-oxo-6-(((R)-1-(6-oxo-6-(((2S,3R,4R,5R)-2,3,4,5,6-pentahydroxyhexyl)amino)hexyl)piperidin-3-yl)amino)hexyl)piperidin-4-yl)-2,3-dihydrobenzofuran-7-carboxamide

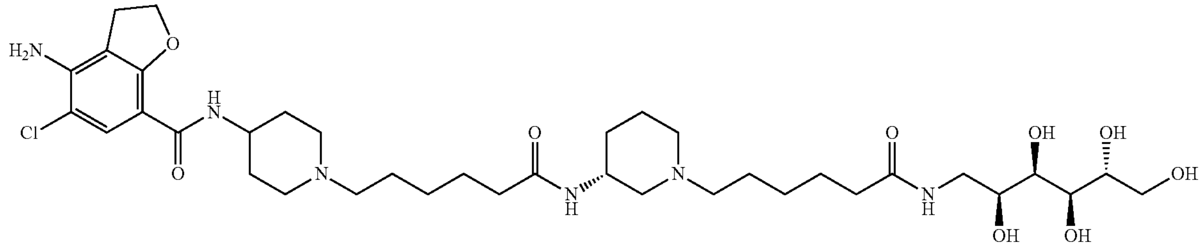 [SMILES: Nc1c(Cl)cc(C(=O)NC2CCN(CCCCCC(=O)N[C@@H]3CCCN(CCCCCC(=O)NC[C@H](O)[C@@H](O)[C@H](O)[C@H](O)CO)C3)CC2)c2c1CCO2]

The title compound was prepared like Example 28, using (R)-6-(3-(6-(4-(4-amino-5-chloro-2,3-dihydrobenzofuran-7-carboxamido)piperidin-1-yl)hexanamido)piperidin-1-yl)hexanoic acid in place of (R)-8-(3-(6-(4-(4-amino-5-chloro-2,3-dihydrobenzofuran-7-carboxamido)piperidin-1-yl)hexanamido)piperidin-1-yl)octanoic acid, and was obtained as a yellow solid. $^1H$ NMR (400 MHz, DMSO-$d_6$) δ ppm 7.59 (s, 1H), 4.79 (t, J=8.8 Hz, 3H), 3.92 (s, 2H), 3.80-3.55 (m, 7H), 3.50-3.40 (m, 1H), 3.26-3.20 (m, 1H), 3.15-3.04 (m, 3H), 2.95-2.86 (m, 2H), 2.84-2.70 (m, 1H), 2.60-2.30 (m, 6H), 2.26-2.32 (m, 4H), 2.29-1.95 (m, 2H), 1.80-1.71 (m, 2H), 1.70-1.50 (m, 12H), 1.40-1.27 (m, 5H); ESI-MS m/z $[M+H]^+$ 769.3.

EXAMPLE 30

4-amino-5-chloro-N-(1-(6-oxo-6-((1-(8-oxo-8-(((2S,3R,4R,5R)-2,3,4,5,6-pentahydroxyhexyl)amino)octyl)piperidin-4-yl)amino)hexyl)piperidin-4-yl)-2,3-dihydrobenzofuran-7-carboxamide

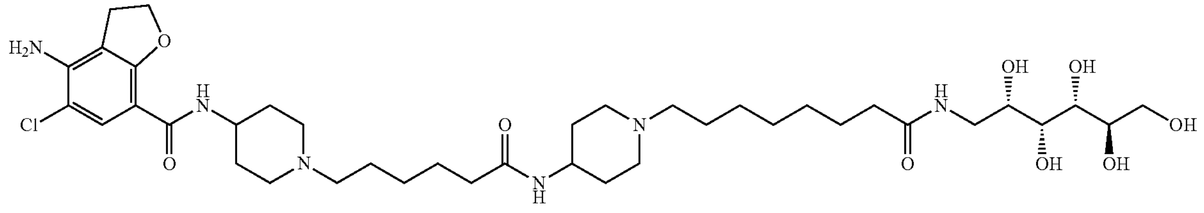 [SMILES: Nc1c(Cl)cc(C(=O)NC2CCN(CCCCCC(=O)NC3CCN(CCCCCCCC(=O)NC[C@H](O)[C@@H](O)[C@H](O)[C@H](O)CO)CC3)CC2)c2c1CCO2]

The title compound was prepared like Example 28, using 8-(4-(6-(4-(4-amino-5-chloro-2,3-dihydrobenzofuran-7-carboxamido)piperidin-1-yl)hexanamido)piperidin-1-yl)octanoic acid (prepared from 6-(4-(4-amino-5-chloro-2,3-dihydrobenzofuran-7-carboxamido)piperidin-1-yl)hexanoic acid and ethyl 8-(4-aminopiperidin-1-yl)octanoate) in place of (R)-8-(3-(6-(4-(4-amino-5-chloro-2,3-dihydrobenzofuran-7-carboxamido)piperidin-1-yl)hexanamido)piperidin-1-yl)octanoic acid, and was obtained as a tan semi-solid. ESI-MS m/z $[M+H]^+$ 798.1.

EXAMPLE 31

4-amino-5-chloro-N-(1-(6-oxo-6-((1-(6-oxo-6-(((2S,3R,4R,5R)-2,3,4,5,6-pentahydroxyhexyl)amino)hexyl)piperidin-4-yl)amino)hexyl)piperidin-4-yl)-2,3-dihydrobenzofuran-7-carboxamide

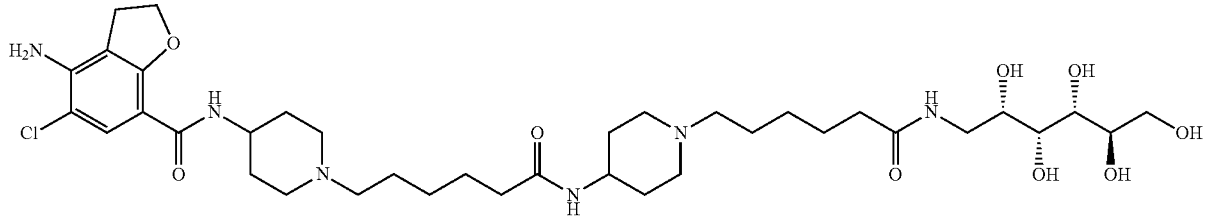 [SMILES: Nc1c(Cl)cc(C(=O)NC2CCN(CCCCCC(=O)NC3CCN(CCCCCC(=O)NC[C@H](O)[C@@H](O)[C@H](O)[C@H](O)CO)CC3)CC2)c2c1CCO2]

The title compound was prepared like Example 28, using 6-(4-(6-(4-(4-amino-5-chloro-2,3-dihydrobenzofuran-7-carboxamido)piperidin-1-yl)hexanamido)piperidin-1-yl)hexanoic acid (prepared from 6-(4-(4-amino-5-chloro-2,3-dihydrobenzofuran-7-carboxamido)piperidin-1-yl)hexanoic acid and methyl 6-(4-aminopiperidin-1-yl)hexanoate) in place of (R)-8-(3-(6-(4-(4-amino-5-chloro-2,3-dihydrobenzofuran-7-carboxamido)piperidin-1-yl)hexanamido)piperidin-1-yl)octanoic acid, and was obtained as a tan semi-solid. ESI-MS m/z $[M+H]^+$ 770.3.

EXAMPLE 32

4-amino-5-chloro-N-(1-(6-oxo-6-((8-oxo-8-(((2S,3R,4R,5R)-2,3,4,5,6-pentahydroxyhexyl)amino)octyl)amino)hexyl)piperidin-4-yl)-2,3-dihydrobenzofuran-7-carboxamide

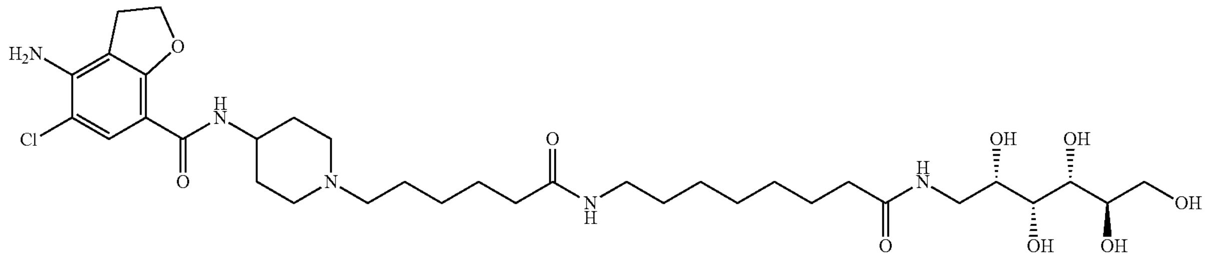 [SMILES: Nc1c(Cl)cc(C(=O)NC2CCN(CCCCCC(=O)NCCCCCCCC(=O)NC[C@H](O)[C@@H](O)[C@H](O)[C@H](O)CO)CC2)c2c1CCO2]

The title compound was prepared like Example 28, using 8-(6-(4-(4-amino-5-chloro-2,3-dihydrobenzofuran-7-carboxamido)piperidin-1-yl)hexanamido)octanoic acid in place of (R)-8-(3-(6-(4-(4-amino-5-chloro-2,3-dihydrobenzofuran-7-carboxamido)piperidin-1-yl)hexanamido)piperidin-1-yl)octanoic acid, and was obtained as a tan solid. ESI-MS m/z $[M+H]^+$ 715.3.

EXAMPLE 33

4-amino-5-chloro-N-(1-(6-oxo-6-((6-oxo-6-(((2S,3R,4R,5R)-2,3,4,5,6-pentahydroxyhexyl)amino)hexyl)amino)hexyl)piperidin-4-yl)-2,3-dihydrobenzofuran-7-carboxamide

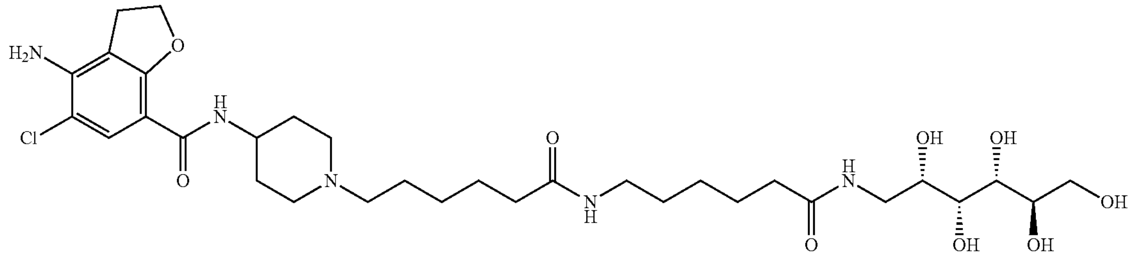 [SMILES: Nc1c(Cl)cc(C(=O)NC2CCN(CCCCCC(=O)NCCCCCC(=O)NC[C@H](O)[C@@H](O)[C@H](O)[C@H](O)CO)CC2)c2c1CCO2]

The title compound was prepared like Example 28, using 6-(6-(4-(4-amino-5-chloro-2,3-dihydrobenzofuran-7-carboxamido)piperidin-1-yl)hexanamido)hexanoic acid in place of (R)-8-(3-(6-(4-(4-amino-5-chloro-2,3-dihydrobenzofuran-7-carboxamido)piperidin-1-yl)hexanamido)piperidin-1-yl)octanoic acid, and was obtained as a tan solid. ESI-MS m/z $[M+H]^+$ 687.3.

EXAMPLE 34

4-amino-5-chloro-N-(1-(6-oxo-6-((4-oxo-4-(((2S,3R,4R,5R)-2,3,4,5,6-pentahydroxyhexyl)amino)butyl)amino)hexyl)piperidin-4-yl)-2,3-dihydrobenzofuran-7-carboxamide

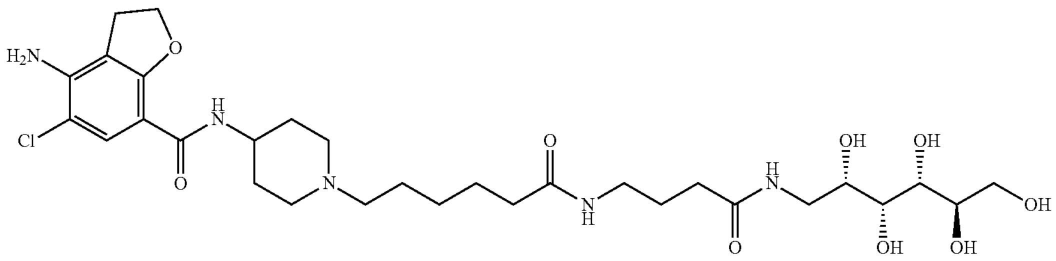 [SMILES: Nc1c(Cl)cc(C(=O)NC2CCN(CCCCCC(=O)NCCCC(=O)NC[C@H](O)[C@@H](O)[C@H](O)[C@H](O)CO)CC2)c2c1CCO2]

The title compound was prepared like Example 28, using 4-(6-(4-(4-amino-5-chloro-2,3-dihydrobenzofuran-7-carboxamido)piperidin-1-yl)hexanamido)butanoic acid in place of (R)-8-(3-(6-(4-(4-amino-5-chloro-2,3-dihydrobenzofuran-7-carboxamido)piperidin-1-yl)hexanamido)piperidin-1-yl)octanoic acid, and was obtained as a tan solid. ESI-MS m/z $[M+H]^+$ 659.0.

EXAMPLE 35

4-amino-5-chloro-N-((1-((1-(9-oxo-9-(((2S,3R,4R,5R)-2,3,4,5,6-pentahydroxyhexyl)amino)nonyl)piperidin-4-yl)methyl)piperidin-4-yl)methyl)-2,3-dihydrobenzofuran-7-carboxamide

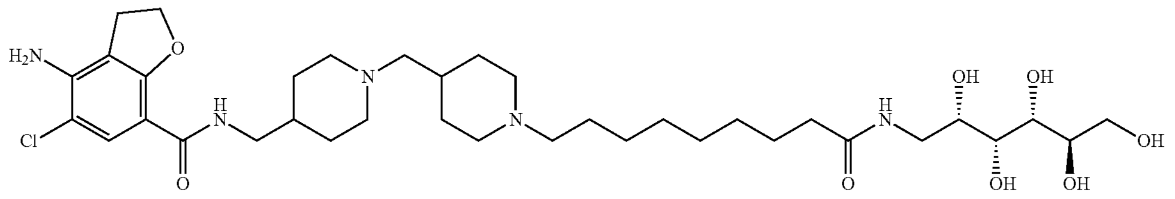 [SMILES: Nc1c(Cl)cc(C(=O)NCC2CCN(CC3CCN(CCCCCCCCC(=O)NC[C@H](O)[C@@H](O)[C@H](O)[C@H](O)CO)CC3)CC2)c2c1CCO2]

A mixture of 9-(4-((4-((4-amino-5-chloro-2,3-dihydrobenzofuran-7-carboxamido)methyl)piperidin-1-yl)methyl)piperidin-1-yl)nonanoic acid (2.3 g, 4.08 mmol, Preparation 70), (2R,3R,4R,5S)-6-aminohexane-1,2,3,4,5-pentaol (2.22 g, 12.25 mmol), DIPEA (2.11 g, 16.34 mmol, 2.85 mL) and HATU (3.11 g, 8.17 mmol) in DMF (30 mL) was stirred at 80° C. for 2 hours. The reaction mixture was then concentrated and purified by preparative HPLC (Kromasil Eternity XT, 250×80 mm, 10 μm) using a gradient (40 to 70%) of ACN/water (0.05% $NH_4OH$). The title compound was obtained as a yellow solid (600.81 mg, 19.65% yield, 97% purity). $^1H$ NMR (400 MHz, DMSO-$d_6$) δ ppm 7.60 (s, 1H), 4.79 (t, J=8.8 Hz, 2H), 3.85-3.73 (m, 4H), 3.66-3.58 (m, 2H), 3.50-3.42 (m, 1H), 3.30-3.28 (m, 3H), 3.28 (t, J=8.4 Hz, 2H), 3.09-2.80 (m, 4H), 2.47-2.27 (m, 2H), 2.27-2.10 (m, 4H), 2.10-1.90 (m, 4H), 1.85-1.75 (m, 4H), 1.75-1.44 (m, 6H), 1.44-1.25 (m, 12H); ESI-MS m/z $[M+H]^+$ 726.5.

EXAMPLE 36

4-amino-5-chloro-N-((1-((1-(11-oxo-11-(((2S,3R,4R,5R)-2,3,4,5,6-pentahydroxyhexyl)amino)undecyl)piperidin-4-yl)methyl)piperidin-4-yl)methyl)-2,3-dihydrobenzofuran-7-carboxamide

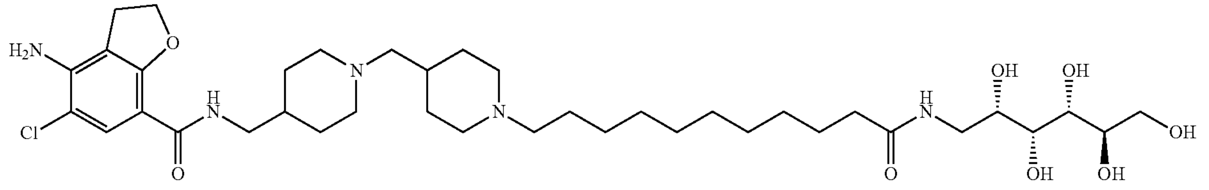 [SMILES: Nc1c(Cl)cc(C(=O)NCC2CCN(CC3CCN(CCCCCCCCCCC(=O)NC[C@H](O)[C@@H](O)[C@H](O)[C@H](O)CO)CC3)CC2)c2c1CCO2]

The title compound was prepared like Example 35, using 11-(4-((4-((4-amino-5-chloro-2,3-dihydrobenzofuran-7-carboxamido)methyl)piperidin-1-yl)methyl)piperidin-1-yl)undecanoic acid in place of 9-(4-((4-((4-amino-5-chloro-2,3-dihydrobenzofuran-7-carboxamido)methyl)piperidin-1-yl)methyl)piperidin-1-yl)nonanoic acid, and was obtained as a white solid. ESI-MS m/z $[M+H]^+$ 755.0.

EXAMPLE 37

4-amino-5-chloro-N-((1-((1-(7-oxo-7-(((2S,3R,4R,5R)-2,3,4,5,6-pentahydroxyhexyl)amino)heptyl)piperidin-4-yl)methyl)piperidin-4-yl)methyl)-2,3-dihydrobenzofuran-7-carboxamide

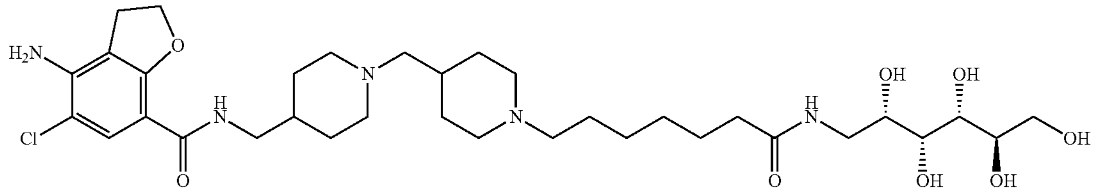 [SMILES: Nc1c(Cl)cc(C(=O)NCC2CCN(CC3CCN(CCCCCCC(=O)NC[C@H](O)[C@@H](O)[C@H](O)[C@H](O)CO)CC3)CC2)c2c1CCO2]

The title compound was prepared like Example 35, using 7-(4-((4-((4-amino-5-chloro-2,3-dihydrobenzofuran-7-carboxamido)methyl)piperidin-1-yl)methyl)piperidin-1-yl) heptanoic acid in place of 9-(4-((4-((4-amino-5-chloro-2,3-dihydrobenzofuran-7-carboxamido)methyl)piperidin-1-yl) methyl)piperidin-1-yl)nonanoic acid, and was obtained as an off-white solid. ESI-MS m/z $[M+H]^+$ 699.3.

EXAMPLE 38

4-amino-5-chloro-N-((1-((1-(12-oxo-12-(((2S,3R,4R,5R)-2,3,4,5,6-pentahydroxyhexyl)amino)dodecanoyl)piperidin-4-yl)methyl)piperidin-4-yl)methyl)-2,3-dihydrobenzofuran-7-carboxamide

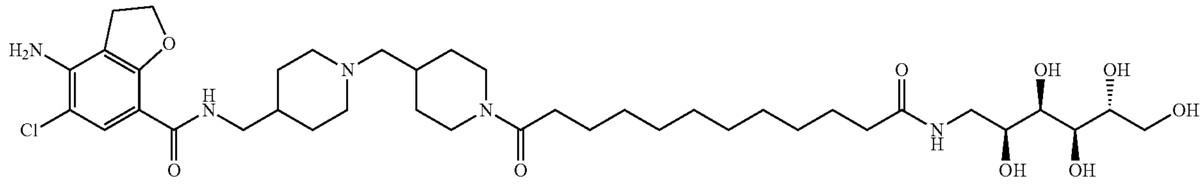 [SMILES: Nc1c(Cl)cc(C(=O)NCC2CCN(CC3CCN(C(=O)CCCCCCCCCCC(=O)NC[C@H](O)[C@@H](O)[C@H](O)[C@H](O)CO)CC3)CC2)c2c1CCO2]

The title compound was prepared like Example 35, using 12-(4-((4-((4-amino chloro-2,3-dihydrobenzofuran-7-carboxamido)methyl)piperidin-1-yl)methyl)piperidin-1-yl)-12-oxododecanoic acid in place of 9-(4-((4-((4-amino-5-chloro-2,3-dihydrobenzofuran carboxamido)methyl)piperidin-1-yl) methyl)piperidin-1-yl)nonanoic acid, and was obtained as an off-white solid. ESI-MS m/z $[M+H]^+$ 783.3.

EXAMPLE 39

4-amino-5-chloro-N-((1-((1-(10-oxo-10-(((2S,3R,4R,5R)-2,3,4,5,6-pentahydroxyhexyl)amino)decanoyl)piperidin-4-yl)methyl)piperidin-4-yl)methyl)-2,3-dihydrobenzofuran-7-carboxamide

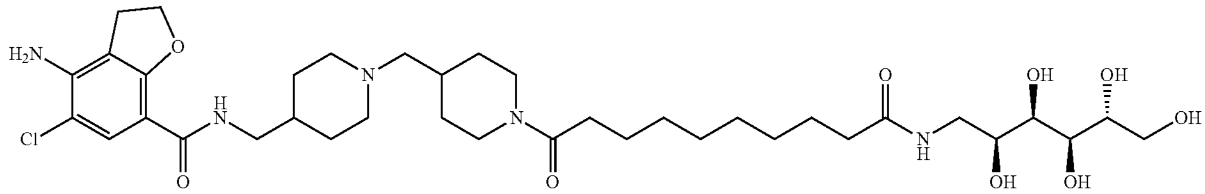 [SMILES: Nc1c(Cl)cc(C(=O)NCC2CCN(CC3CCN(C(=O)CCCCCCCCC(=O)NC[C@H](O)[C@@H](O)[C@H](O)[C@H](O)CO)CC3)CC2)c2c1CCO2]

The title compound was prepared like Example 35, using 10-(4-((4-((4-amino-5-chloro-2,3-dihydrobenzofuran-7-carboxamido)methyl)piperidin-1-yl)methyl)piperidin-1-yl)-10-oxodecanoic acid in place of 9-(4-((4-((4-amino-5-chloro-2,3-dihydrobenzofuran-7-carboxamido)methyl)piperidin-1-yl)methyl)piperidin-1-yl)nonanoic acid, and was obtained as an off-white solid. ESI-MS m/z $[M+H]^+$ 755.3.

EXAMPLE 40

4-amino-5-chloro-N-((1-((1-(8-oxo-8-(((2S,3R,4R,5R)-2,3,4,5,6-pentahydroxyhexyl)amino)octanoyl)piperidin-4-yl)methyl)piperidin-4-yl)methyl)-2,3-dihydrobenzofuran-7-carboxamide

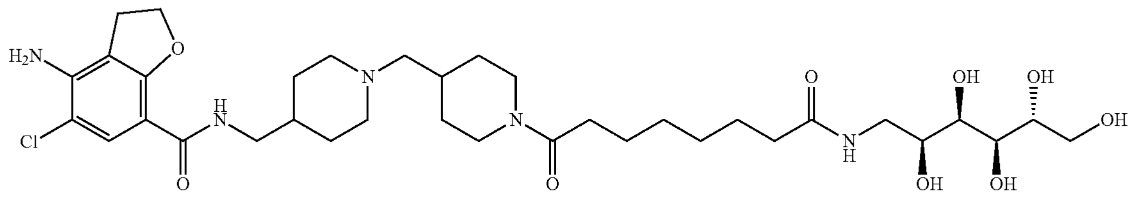 [SMILES: Nc1c(Cl)cc(C(=O)NCC2CCN(CC3CCN(C(=O)CCCCCCC(=O)NC[C@H](O)[C@@H](O)[C@H](O)[C@H](O)CO)CC3)CC2)c2c1CCO2]

The title compound was prepared like Example 35, using 8-(4-((4-((4-amino-5-chloro-2,3-dihydrobenzofuran-7-carboxamido)methyl)piperidin-1-yl)methyl)piperidin-1-yl)-8-oxooctanoic acid in place of 9-(4-((4-((4-amino-5-chloro-2,3-dihydrobenzofuran-7-carboxamido)methyl)piperidin-1-yl)methyl)piperidin-1-yl)nonanoic acid, and was obtained as an off-white solid. ESI-MS m/z $[M+H]^+$ 727.3.

EXAMPLE 41

4-amino-5-chloro-N-((3S,4R)-3-methoxy-1-((1-(9-oxo-9-(((2S,3R,4R,5R)-2,3,4,5,6-pentahydroxyhexyl)amino)nonanoyl)piperidin-4-yl)methyl)piperidin-4-yl)-2,3-dihydrobenzofuran-7-carboxamide

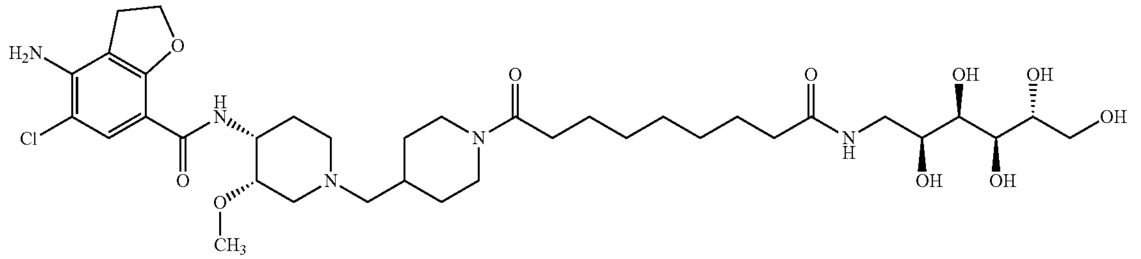 [SMILES: CO[C@H]1CN(CC2CCN(C(=O)CCCCCCCC(=O)NC[C@H](O)[C@@H](O)[C@H](O)[C@H](O)CO)CC2)CC[C@H]1NC(=O)c1cc(Cl)c(N)c2c1OCC2]

The title compound was prepared like Example 35, using 9-(4-(((3S,4R)-4-(4-amino-5-chloro-2,3-dihydrobenzofuran-7-carboxamido)-3-methoxypiperidin-1-yl)methyl)piperidin-1-yl)-9-oxononanoic acid (prepared from 4-amino-5-chloro-N-((3S,4R)-3-methoxypiperidin-4-yl)-2,3-dihydrobenzofuran-7-carboxamide and methyl 9-(4-(bromomethyl)piperidin-1-yl)-9-oxononanoate) in place of 9-(4-((4-((4-amino-5-chloro-2,3-dihydrobenzofuran-7-carboxamido)methyl)piperidin-1-yl)methyl)piperidin-1-yl)nonanoic acid, and was obtained as an off-white solid. ESI-MS m/z $[M+H]^+$ 756.3.

EXAMPLE 42

4-amino-5-chloro-N-((3S,4R)-3-methoxy-1-((1-(7-oxo-7-(((2S,3R,4R,5R)-2,3,4,5,6-pentahydroxyhexyl)amino)heptanoyl)piperidin-4-yl)methyl)piperidin-4-yl)-2,3-dihydrobenzofuran-7-carboxamide

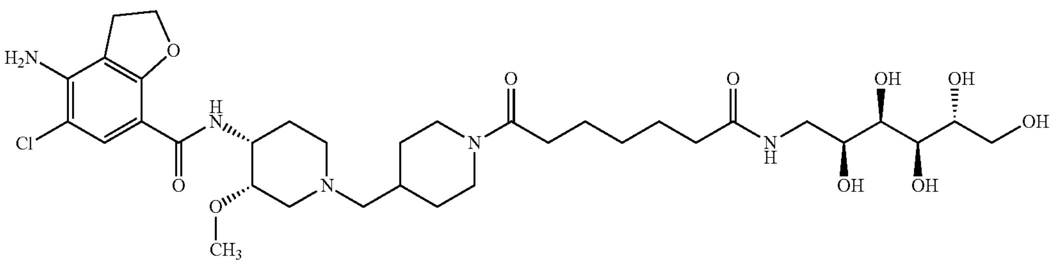 [SMILES: CO[C@H]1CN(CC2CCN(C(=O)CCCCCC(=O)NC[C@H](O)[C@@H](O)[C@H](O)[C@H](O)CO)CC2)CC[C@H]1NC(=O)c1cc(Cl)c(N)c2c1OCC2]

The title compound was prepared like Example 35, using 7-(4-(((3S,4R)-4-(4-amino-5-chloro-2,3-dihydrobenzofuran-7-carboxamido)-3-methoxypiperidin-1-yl)methyl)piperidin-1-yl)-7-oxoheptanoic acid (prepared from 4-amino-5-chloro-N-((3S,4R)-3-methoxypiperidin-4-yl)-2,3-dihydrobenzofuran-7-carboxamide and methyl 7-(4-(bromomethyl)piperidin-1-yl)-7-oxoheptanoate) in place of 9-(4-((4-((4-amino-5-chloro-2,3-dihydrobenzofuran-7-carboxamido)methyl)piperidin-1-yl)methyl)piperidin-1-yl)nonanoic acid, and was obtained as an off-white solid. ESI-MS m/z $[M+H]^+$ 728.3.

EXAMPLE 43

4-amino-5-chloro-N-((3S,4R)-3-methoxy-1-((1-(5-oxo-5-(((2S,3R,4R,5R)-2,3,4,5,6-pentahydroxyhexyl)amino)pentanoyl)piperidin-4-yl)methyl)piperidin-4-yl)-2,3-dihydrobenzofuran-7-carboxamide

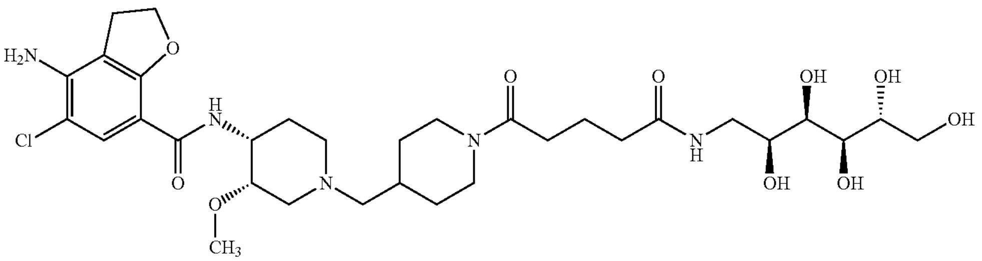 [SMILES: CO[C@H]1CN(CC2CCN(C(=O)CCCC(=O)NC[C@H](O)[C@@H](O)[C@H](O)[C@H](O)CO)CC2)CC[C@H]1NC(=O)c1cc(Cl)c(N)c2c1OCC2]

The title compound was prepared like Example 35, using 5-(4-(((3S,4R)-4-(4-amino-5-chloro-2,3-dihydrobenzofuran-7-carboxamido)-3-methoxypiperidin-1-yl)methyl)piperidin-1-yl)-5-oxopentanoic acid (prepared from 4-amino-5-chloro-N-((3S,4R)-3-methoxypiperidin-4-yl)-2,3-dihydrobenzofuran-7-carboxamide and methyl 5-(4-(bromomethyl)piperidin-1-yl)-5-oxopentanoate) in place of 9-(4-((4-((4-amino-5-chloro-2,3-dihydrobenzofuran-7-carboxamido)methyl)piperidin-1-yl)methyl)piperidin-1-yl)nonanoic acid, and was obtained as an off-white solid. ESI-MS m/z $[M+H]^+$ 700.3.

EXAMPLE 44

4-amino-5-chloro-N-((3S,4R)-3-methoxy-1-(6-oxo-6-((8-oxo-8-(((2S,3R,4R,5R)-2,3,4,5,6-pentahydroxyhexyl)amino)octyl)amino)hexyl)piperidin-4-yl)-2,3-dihydrobenzofuran-7-carboxamide

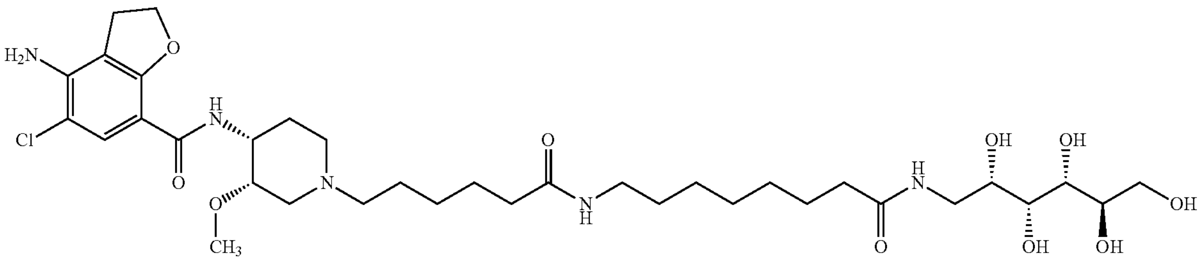 [SMILES: CO[C@H]1CN(CCCCCC(=O)NCCCCCCCC(=O)NC[C@H](O)[C@@H](O)[C@H](O)[C@H](O)CO)CC[C@H]1NC(=O)c1cc(Cl)c(N)c2c1OCC2]

The title compound was prepared like Example 35, using 8-(6-((3S,4R)-4-(4-amino-5-chloro-2,3-dihydrobenzofuran-7-carboxamido)-3-methoxypiperidin-1-yl)hexanamido)octanoic acid (prepared from 4-amino-5-chloro-N-((3S,4R)-3-methoxypiperidin-4-yl)-2,3-dihydrobenzofuran-7-carboxamide and methyl 8-(6-bromohexanamido)octanoate) in place of 9-(4-((4-((4-amino-5-chloro-2,3-dihydrobenzofuran-7-carboxamido)methyl)piperidin-1-yl)methyl)piperidin-1-yl)nonanoic acid, and was obtained as an off-white solid. ESI-MS m/z $[M+H]^+$ 744.3.

EXAMPLE 45

4-amino-5-chloro-N-((3S,4R)-3-methoxy-1-(6-oxo-6-((6-oxo-6-(((2S,3R,4R,5R)-2,3,4,5,6-pentahydroxyhexyl)amino)hexyl)amino)hexyl)piperidin-4-yl)-2,3-dihydrobenzofuran-7-carboxamide

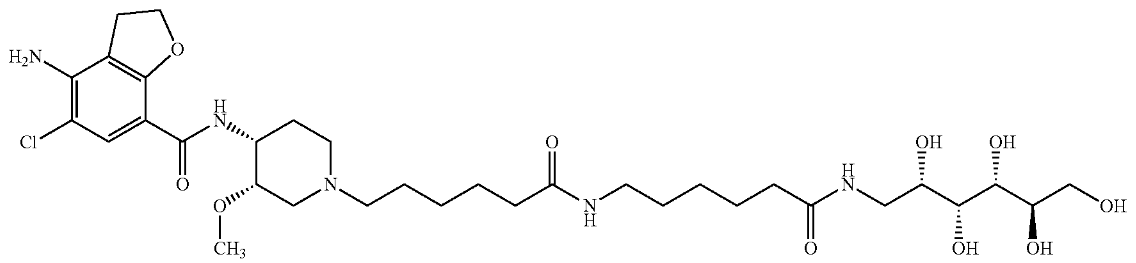 [SMILES: CO[C@H]1CN(CCCCCC(=O)NCCCCCC(=O)NC[C@H](O)[C@@H](O)[C@H](O)[C@H](O)CO)CC[C@H]1NC(=O)c1cc(Cl)c(N)c2c1OCC2]

The title compound was prepared like Example 35, using 6-(6-((3S,4R)-4-(4-amino-5-chloro-2,3-dihydrobenzofuran-7-carboxamido)-3-methoxypiperidin-1-yl)hexanamido) hexanoic acid (prepared from 4-amino-5-chloro-N-((3S,4R) methoxypiperidin-4-yl)-2,3-dihydrobenzofuran-7-carboxamide and methyl 6-(6-bromohexanamido)hexanoate) in place of 9-(4-((4-((4-amino-5-chloro-2,3-dihydrobenzofuran-7-carboxamido)methyl)piperidin-1-yl)methyl)piperidin-1-yl)nonanoic acid, and was obtained as an off-white solid. ESI-MS m/z $[M+H]^+$ 716.3.

EXAMPLE 46

4-amino-5-chloro-N-((3S,4R)-3-methoxy-1-(6-oxo-6-(((4-oxo-4-(((2S,3R,4R,5R)-2,3,4,5,6-pentahydroxyhexyl)amino)butyl)amino)hexyl)piperidin-4-yl)-2,3-dihydrobenzofuran-7-carboxamide

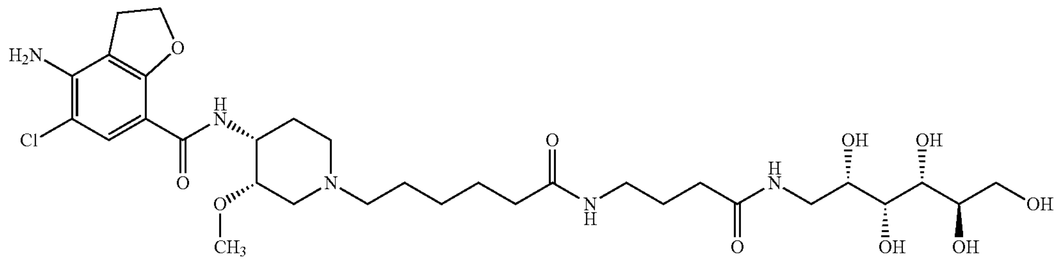 [SMILES: CO[C@H]1CN(CCCCCC(=O)NCCCC(=O)NC[C@H](O)[C@@H](O)[C@H](O)[C@H](O)CO)CC[C@H]1NC(=O)c1cc(Cl)c(N)c2c1OCC2]

The title compound was prepared like Example 35, using 4-(6-((3S,4R)-4-(4-amino-5-chloro-2,3-dihydrobenzofuran-7-carboxamido)-3-methoxypiperidin-1-yl)hexanamido)butanoic acid (prepared from 4-amino-5-chloro-N-((3S,4R)-3-methoxypiperidin-4-yl)-2,3-dihydrobenzofuran-7-carboxamide and methyl 4-(6-bromohexanamido) butanoate) in place of 9-(4-((4-((4-amino-5-chloro-2,3-dihydrobenzofuran-7-carboxamido)methyl)piperidin-1-yl) methyl)piperidin-1-yl)nonanoic acid, and was obtained as an off-white solid. ESI-MS m/z $[M+H]^+$ 688.3.

The ability of the example compounds to activate the $5\text{-HT}_4$(b) receptor was evaluated using the assay described in the Biological Activity section. Table 1, below, lists $EC_{50}$ from the $5\text{-HT}_4$(b) agonist assay for each of the example compounds, where smaller $EC_{50}$ values represent higher potency.

TABLE 1

| $5\text{-HT}_4$(b) Agonist Assay | |
|---|---|
| Example | $EC_{50}$ (nM) |
| 1 | 19.8 |
| 2 | 21.4 |
| 3 | 22.3 |
| 4 | 28.6 |
| 5 | 13.2 |
| 6 | 22.2 |
| 7 | 23.4 |
| 8 | 9.6 |
| 9 | 8.1 |
| 10 | 26.1 |

TABLE 1-continued

| $5\text{-HT}_4$(b) Agonist Assay | |
|---|---|
| Example | $EC_{50}$ (nM) |
| 11 | 14.2 |
| 12 | 14.6 |
| 13 | 12.9 |
| 14 | 16.8 |
| 15 | 31.0 |
| 16 | 43.3 |
| 17 | 201.6 |
| 18 | 150.0 |
| 19 | 77.0 |
| 20 | 57.6 |
| 21 | 27.6 |

TABLE 1-continued

| 5-HT$_4$(b) Agonist Assay | |
|---|---|
| Example | $EC_{50}$ (nM) |
| 22 | 19.1 |
| 23 | 56.5 |
| 24 | 28.7 |
| 25 | 115.4 |
| 26 | 130.6 |
| 27 | 30.3 |
| 28 | 3.8 |
| 29 | 4.4 |
| 30 | 3.7 |
| 31 | 6.1 |
| 32 | 23.0 |
| 33 | 12.6 |
| 34 | 15.3 |
| 35 | 2.6 |
| 36 | 2.5 |
| 37 | 2.0 |
| 38 | 1.2 |
| 39 | 1.2 |
| 40 | 2.0 |
| 41 | 1.2 |
| 42 | 1.4 |
| 43 | 1.7 |
| 44 | 3.1 |
| 45 | 12.1 |
| 46 | 5.9 |

As used in this specification and the appended claims, singular articles such as “a,” “an,” and “the,” may refer to a single object or to a plurality of objects unless the context clearly indicates otherwise. Thus, for example, reference to a composition containing “a compound” may include a single compound or two or more compounds. The above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references cited in the disclosure, including patents, patent applications and publications, are herein incorporated by reference in their entirety and for all purposes.

What is claimed is:

1. A compound of Formula 1,

1

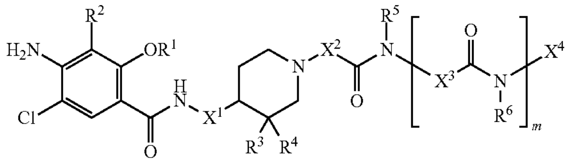

or a pharmaceutically acceptable salt thereof in which:

m is an integer selected from 0 and 1;

$R^1$ is methyl and $R^2$ is hydrogen, or $R^1$ and $R^2$ together form an ethane-1,2-diyl which bridges the oxygen and carbon atoms to which $R^1$ and $R^2$ are respectively attached;

$R^3$ and $R^4$ are each independently selected from hydrogen, halo, $C_{1-4}$ alkyl and $C_{1-3}$ alkoxy;

$R^5$ and $R^6$ are each independently selected from hydrogen and $C_{1-4}$ alkyl which is unsubstituted or substituted with an optional substituent selected from hydroxy, phosphono, sulfo and amino, wherein the amino optional substituent is unsubstituted or substituted with 1 or 2 optional substituents independently selected from $C_{1-3}$ alkyl;

$X^1$ is selected from a bond and methane-1,1-diyl;

$X^2$ is selected from (a) pentane-1,5-diyl which is unsubstituted or substituted with 1 to 5 optional substituents independently selected from halo and $C_{1-3}$ alkyl, wherein one of the carbon atoms of the pentane-1,5-diyl substituent may be optionally replaced with one oxygen atom, provided the oxygen atom is directly bonded to two carbon atoms within the pentane-1,5-diyl substituent; and (b) a moiety represented by the formula

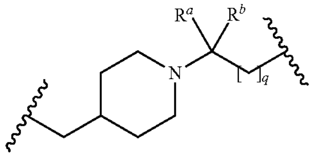

wherein $R^a$ and $R^b$ are each hydrogen or together represent oxo; and q is an integer selected from 1, 2, 3, 4, 5, 6, 7, 8, 9 and 10;

$X^3$ is selected from (a) $C_{1-11}$ alkanediyl, wherein 0 to 3 carbon atoms of the alkanediyl substituent may be optionally replaced, one-to-one, with oxygen atoms, provided each replacement oxygen atom is directly bonded to two carbon atoms within the alkanediyl substituent and any two replacement oxygen atoms are separated by at least one carbon atom; and (b) a moiety represented by the formula,

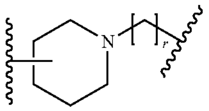

wherein r is an integer selected from 1, 2, 3, 4, 5, 6 and 7; and $X^4$ is selected from (a) $C_{3-6}$ alkyl which is substituted with 3 to 6 hydroxy substituents;

(b) $C_{1-3}$ alkyl which is substituted with phosphono or sulfo substituents; and (c) cyclohexyl which is substituted with 3 to 6 substituents independently selected from hydroxy and hydroxymethyl;

wherein the bracketed moieties in Formula 1 and in the formulas for $X^2$ and $X^3$ are present m, q or r times, respectively, and each on represents a point of attachment in the formulas for $X^2$ and $X^3$.

2. The compound or pharmaceutically acceptable salt thereof according to claim 1, wherein $R^1$ is methyl and $R^2$ is hydrogen.

3. The compound or pharmaceutically acceptable salt thereof according to claim 1, wherein $R^1$ and $R^2$ together form an ethane-1,2-diyl which bridges the oxygen and carbon atoms to which $R^1$ and $R^2$ are respectively attached.

4. The compound or pharmaceutically acceptable salt thereof according to claim 1, wherein $X^1$ is a bond.

5. The compound or pharmaceutically acceptable salt thereof according to claim 1, wherein $X^1$ is methane-1,1-diyl.

6. The compound or pharmaceutically acceptable salt thereof according to claim 1, wherein $R^3$ and $R^4$ are each independently selected from hydrogen and methoxy.

7. The compound or pharmaceutically acceptable salt thereof according to claim 1, wherein $R^3$ and $R^4$ are each hydrogen.

8. The compound or pharmaceutically acceptable salt thereof according to claim 1, wherein $X_2$ is pentane-1,5-diyl which is unsubstituted or substituted with 1 to 5 optional substituents independently selected from halo and $C_{1-3}$ alkyl, wherein one of the carbon atoms of the pentane-1,5-diyl substituent may be optionally replaced with one oxygen atom, provided the oxygen atom is directly bonded to two carbon atoms within the pentane-1,5-diyl substituent.

9. The compound or pharmaceutically acceptable salt thereof according to claim 1, wherein $X_2$ is pentane-1,5-diyl which is unsubstituted or substituted with 1 to 5 optional substituents selected from methyl, wherein one of the carbon atoms of the pentane-1,5-diyl substituent may be optionally replaced with one oxygen atom, provided the oxygen atom is directly bonded to two carbon atoms within the pentane-1,5-diyl substituent.

10. The compound or pharmaceutically acceptable salt thereof according to claim 1, wherein $X_2$ is pentane-1,5-diyl which is unsubstituted, and wherein one of the carbon atoms of the pentane-1,5-diyl substituent may be optionally replaced with one oxygen atom, provided the oxygen atom is directly bonded to two carbon atoms within the pentane-1,5-diyl substituent.

11. The compound or pharmaceutically acceptable salt thereof according to claim 8, wherein $X_2$ is pentane-1,5-diyl in which none of the carbon atoms of the pentane-1,5-diyl substituent is optionally replaced with an oxygen atom.

12. The compound or pharmaceutically acceptable salt thereof according to claim 1, wherein $X^2$ is a moiety represented by the formula

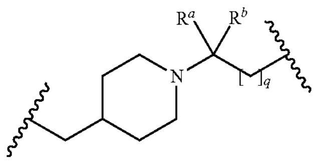
, wherein $R^a$ and $R^b$ are each hydrogen or together represent oxo; and q is an integer selected from 1, 2, 3, 4, 5, 6, 7, 8, 9 and 10.

13. The compound or pharmaceutically acceptable salt thereof according to claim 12, wherein $R^a$ and $R^b$ are each hydrogen.

14. The compound or pharmaceutically acceptable salt thereof according to claim 12, wherein $R^a$ and $R^b$ together represent oxo.

15. The compound or pharmaceutically acceptable salt thereof according to claim 12, wherein q is an integer selected from 3, 4, 5, 6, 7, 8, 9 and 10.

16. The compound or pharmaceutically acceptable salt thereof according to claim 1, wherein $R^5$ is selected from hydrogen and methyl.

17. The compound or pharmaceutically acceptable salt thereof according to claim 1, wherein $R^5$ is hydrogen.

18. The compound or pharmaceutically acceptable salt thereof according to claim 1, wherein $X^3$ is $C_{1-11}$ alkanediyl, wherein 0 to 3 carbon atoms of the alkanediyl substituent may be optionally replaced, one-to-one, with oxygen atoms, provided each replacement oxygen atom is directly bonded to two carbon atoms within the alkanediyl substituent and any two replacement oxygen atoms are separated by at least one carbon atom.

19. The compound or pharmaceutically acceptable salt thereof according to claim 1, wherein $X^3$ is $C_{1-7}$ alkanediyl in which none of the carbon atoms of the alkanediyl substituent is replaced with oxygen atoms.

20. The compound or pharmaceutically acceptable salt thereof according to claim 1, wherein $X^3$ is a moiety represented by the formula,

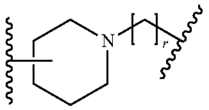
, wherein r is an integer selected from 1, 2, 3, 4, 5, 6 and 7.

21. The compound or pharmaceutically acceptable salt thereof according to claim 20, wherein r is an integer selected from 3, 4, 5, 6 and 7.

22. The compound or pharmaceutically acceptable salt thereof according to claim 1, wherein $R^6$ is selected from hydrogen, methyl, hydroxyethyl, phosphonoethyl, sulfoethyl and dimethylaminopropyl.

23. The compound or pharmaceutically acceptable salt thereof according to claim 1, wherein $X^4$ is $C_{3-6}$ alkyl which is substituted with 3 to 6 hydroxy substituents.

24. The compound or pharmaceutically acceptable salt thereof according to claim 1, wherein $X^4$ is (2S,3R,4R,5R)-2,3,4,5,6-pentahydroxyhexyl or a stereoisomer thereof.

25. The compound or pharmaceutically acceptable salt thereof according to claim 1, wherein $X^4$ is $C_{1-3}$ alkyl which is substituted with phosphono or sulfo substituents.

26. The compound or pharmaceutically acceptable salt thereof according to claim 1, wherein $X^4$ is cyclohexyl which is substituted with 3 to 6 substituents independently selected from hydroxy and hydroxymethyl.

27. The compound or pharmaceutically acceptable salt thereof according to claim 1, wherein $X^4$ is (2S,3R,4S,5S)-2,3,4,5-tetrahydroxy-5-(hydroxymethyl)cyclohexyl or a stereoisomer thereof.

28. The compound according to claim 1, which is selected from the following compounds:

4-amino-5-chloro-2-methoxy-N-((3S,4R)-3-methoxy-1-(6-oxo-6-(((2S,3R,4R,5R)-2,3,4,5,6-pentahydroxyhexyl)amino)hexyl)piperidin-4-yl)benzamide;

4-amino-5-chloro-2-methoxy-N-((3S,4R)-3-methoxy-1-(6-oxo-6-((8-oxo-8-(((2S,3R,4R,5R)-2,3,4,5,6-pentahydroxyhexyl)amino)octyl)amino)hexyl)piperidin-4-yl)benzamide;

4-amino-5-chloro-2-methoxy-N-((3S,4R)-3-methoxy-1-(6-oxo-6-((6-oxo-6-(((2S,3R,4R,5R)-2,3,4,5,6-pentahydroxyhexyl)amino)hexyl)amino)hexyl)piperidin-4-yl)benzamide;

4-amino-5-chloro-2-methoxy-N-((3S,4R)-3-methoxy-1-(6-oxo-6-((4-oxo-4-(((2S,3R,4R,5R)-2,3,4,5,6-pentahydroxyhexyl)amino)butyl)amino)hexyl)piperidin-4-yl)benzamide;

4-amino-5-chloro-2-methoxy-N-((3S,4R)-3-methoxy-1-(6-oxo-6-((2-oxo-2-(((2S,3R,4R,5R)-2,3,4,5,6-pentahydroxyhexyl)amino)ethyl)amino)hexyl)piperidin-4-yl)benzamide;

4-amino-5-chloro-2-methoxy-N-((3S,4R)-3-methoxy-1-((22S,23R,24R,25R)-22,23,24,25,26-pentahydroxy-6,19-dioxo-10,13,16-trioxa-7,20-diazahexacosyl)piperidin-4-yl)benzamide;

4-amino-5-chloro-2-methoxy-N-((3S,4R)-3-methoxy-1-((19S,20R,21R,22R)-19,20,21,22,23-pentahydroxy-6,16-dioxo-10,13-dioxa-7,17-diazatricosyl)piperidin-4-yl)benzamide;

4-amino-5-chloro-2-methoxy-N-((3S,4R)-3-methoxy-1-(6-oxo-6-((1-(8-oxo-8-(((2S,3R,4R,5R)-2,3,4,5,6-pentahydroxyhexyl)amino)octyl)piperidin-4-yl)amino)hexyl)piperidin-4-yl)benzamide;

4-amino-5-chloro-2-methoxy-N-((3S,4R)-3-methoxy-1-(6-oxo-6-((1-(6-oxo-6-(((2S,3R,4R,5R)-2,3,4,5,6-pentahydroxyhexyl)amino)hexyl)piperidin-4-yl)amino)hexyl)piperidin-4-yl)benzamide;

4-amino-5-chloro-2-methoxy-N-((3S,4R)-3-methoxy-1-(6-(methyl(1-(8-oxo-8-(((2S,3R,4R,5R)-2,3,4,5,6-pentahydroxyhexyl)amino)octyl)piperidin-4-yl)amino)-6-oxohexyl)piperidin-4-yl)benzamide;

4-amino-5-chloro-2-methoxy-N-((3S,4R)-3-methoxy-1-(6-(methyl(1-(6-oxo-6-(((2S,3R,4R,5R)-2,3,4,5,6-pentahydroxyhexyl)amino)hexyl)piperidin-4-yl)amino)-6-oxohexyl)piperidin-4-yl)benzamide;

4-amino-5-chloro-2-methoxy-N-((3S,4R)-3-methoxy-1-(6-oxo-6-(((R)-1-(8-oxo-8-(((2S,3R,4R,5R)-2,3,4,5,6-pentahydroxyhexyl)amino)octyl)piperidin-3-yl)amino)hexyl)piperidin-4-yl)benzamide;

4-amino-5-chloro-2-methoxy-N-((3S,4R)-3-methoxy-1-(6-oxo-6-(((R)-1-(6-oxo-6-(((2S,3R,4R,5R)-2,3,4,5,6-pentahydroxyhexyl)amino)hexyl)piperidin-3-yl)amino)hexyl)piperidin-4-yl)benzamide;

4-amino-5-chloro-2-methoxy-N-((3S,4R)-3-methoxy-1-(6-(methyl((R)-1-(8-oxo-8-(((2S,3R,4R,5R)-2,3,4,5,6-pentahydroxyhexyl)amino)octyl)piperidin-3-yl)amino)-6-oxohexyl)piperidin-4-yl)benzamide;

4-amino-5-chloro-2-methoxy-N-((3S,4R)-3-methoxy-1-(6-(methyl((R)-1-(6-oxo-6-(((2S,3R,4R,5R)-2,3,4,5,6-pentahydroxyhexyl)amino)hexyl)piperidin-3-yl)amino)-6-oxohexyl)piperidin-4-yl)benzamide;

4-amino-5-chloro-2-methoxy-N-((3S,4R)-3-methoxy-1-(6-(methyl(8-oxo-8-(((2S,3R,4R,5R)-2,3,4,5,6-pentahydroxyhexyl)amino)octyl)amino)-6-oxohexyl)piperidin-4-yl)benzamide;

4-amino-5-chloro-2-methoxy-N-((3S,4R)-3-methoxy-1-(2-(3-oxo-3-((8-oxo-8-(((2S,3R,4R,5R)-2,3,4,5,6-pentahydroxyhexyl)amino)octyl)amino) propoxy)ethyl)piperidin-4-yl)benzamide;

4-amino-5-chloro-2-methoxy-N-((3S,4R)-3-methoxy-1-(7-oxo-7-((8-oxo-8-(((2S,3R,4R,5R)-2,3,4,5,6-pentahydroxyhexyl)amino)octyl)amino)heptan-2-yl)piperidin-4-yl)benzamide;

4-amino-5-chloro-2-methoxy-N-((3S,4R)-3-methoxy-1-(2-methyl-6-oxo-6-((8-oxo-8-(((2S,3R,4R,5R)-2,3,4,5,6-pentahydroxyhexyl)amino)octyl)amino)hexyl)piperidin-4-yl)benzamide;

4-amino-5-chloro-2-methoxy-N-((3S,4R)-3-methoxy-1-(3-methyl-6-oxo-6-((8-oxo-8-(((2S,3R,4R,5R)-2,3,4,5,6-pentahydroxyhexyl)amino)octyl)amino)hexyl)piperidin-4-yl)benzamide;

4-amino-5-chloro-2-methoxy-N-((3S,4R)-3-methoxy-1-(4-methyl-6-oxo-6-((8-oxo-8-(((2S,3R,4R,5R)-2,3,4,5,6-pentahydroxyhexyl)amino)octyl)amino)hexyl)piperidin-4-yl)benzamide;

4-amino-5-chloro-N-((3S,4R)-1-(6-((8-((2-hydroxyethyl)((2S,3R,4R,5R)-2,3,4,5,6-pentahydroxyhexyl)amino)-8-oxooctyl)amino)-6-oxohexyl)-3-methoxypiperidin-4-yl)-2-methoxybenzamide;

2-(8-(6-((3S,4R)-4-(4-amino-5-chloro-2-methoxybenzamido)-3-methoxypiperidin-1-yl)hexanamido)octanamido)ethane-1-sulfonic acid;

4-amino-5-chloro-2-methoxy-N-((3S,4R)-3-methoxy-1-(6-oxo-6-((8-oxo-8-(((1S,2S,3R,4S,5S)-2,3,4,5-tetrahydroxy-5-(hydroxymethyl)cyclohexyl)amino)octyl)amino)hexyl)piperidin-4-yl)benzamide;

(2-(8-(6-((3S,4R)-4-(4-amino-5-chloro-2-methoxybenzamido)-3-methoxypiperidin-1-yl)hexanamido)octanamido)ethyl)phosphonic acid;

(2-(8-(6-((3S,4R)-4-(4-amino-5-chloro-2-methoxybenzamido)-3-methoxypiperidin-1-yl)hexanamido)-N-((2S,3R,4R,5R)-2,3,4,5,6-pentahydroxyhexyl)octanamido)ethyl)phosphonic acid;

2-(8-(6-((3S,4R)-4-(4-amino-5-chloro-2-methoxybenzamido)-3-methoxypiperidin-1-yl)hexanamido)-N-(3-(dimethylamino)propyl)octanamido)ethane-1-sulfonic acid;

4-amino-5-chloro-N-(1-(6-oxo-6-(((R)-1-(8-oxo-8-(((2S,3R,4R,5R)-2,3,4,5,6-pentahydroxyhexyl)amino)octyl)piperidin-3-yl)amino)hexyl)piperidin-4-yl)-2,3-dihydrobenzofuran-7-carboxamide;

4-amino-5-chloro-N-(1-(6-oxo-6-(((R)-1-(6-oxo-6-(((2S,3R,4R,5R)-2,3,4,5,6-pentahydroxyhexyl)amino)hexyl)piperidin-3-yl)amino)hexyl)piperidin-4-yl)-2,3-dihydrobenzofuran-7-carboxamide;

4-amino-5-chloro-N-(1-(6-oxo-6-((1-(8-oxo-8-(((2S,3R,4R,5R)-2,3,4,5,6-pentahydroxyhexyl)amino)octyl)piperidin-4-yl)amino)hexyl)piperidin-4-yl)-2,3-dihydrobenzofuran-7-carboxamide;

4-amino-5-chloro-N-(1-(6-oxo-6-((1-(6-oxo-6-(((2S,3R,4R,5R)-2,3,4,5,6-pentahydroxyhexyl)amino)hexyl)piperidin-4-yl)amino)hexyl)piperidin-4-yl)-2,3-dihydrobenzofuran-7-carboxamide;

4-amino-5-chloro-N-(1-(6-oxo-6-((8-oxo-8-(((2S,3R,4R,5R)-2,3,4,5,6-pentahydroxyhexyl)amino)octyl)amino)hexyl)piperidin-4-yl)-2,3-dihydrobenzofuran-7-carboxamide;

4-amino-5-chloro-N-(1-(6-oxo-6-((6-oxo-6-(((2S,3R,4R,5R)-2,3,4,5,6-pentahydroxyhexyl)amino)hexyl)amino)hexyl)piperidin-4-yl)-2,3-dihydrobenzofuran-7-carboxamide;

4-amino-5-chloro-N-(1-(6-oxo-6-((4-oxo-4-(((2S,3R,4R,5R)-2,3,4,5,6-pentahydroxyhexyl)amino)butyl)amino)hexyl)piperidin-4-yl)-2,3-dihydrobenzofuran-7-carboxamide;

4-amino-5-chloro-N-((1-((1-(9-oxo-9-(((2S,3R,4R,5R)-2,3,4,5,6-pentahydroxyhexyl)amino)nonyl)piperidin-4-yl)methyl)piperidin-4-yl)methyl)-2,3-dihydrobenzofuran-7-carboxamide;

4-amino-5-chloro-N-((1-((1-(11-oxo-11-(((2S,3R,4R,5R)-2,3,4,5,6-pentahydroxyhexyl)amino)undecyl)piperidin-4-yl)methyl)piperidin-4-yl)methyl)-2,3-dihydrobenzofuran-7-carboxamide;

4-amino-5-chloro-N-((1-((1-(7-oxo-7-(((2S,3R,4R,5R)-2,3,4,5,6-pentahydroxyhexyl)amino)heptyl)piperidin-4-yl)methyl)piperidin-4-yl)methyl)-2,3-dihydrobenzofuran-7-carboxamide;

4-amino-5-chloro-N-((1-((1-(12-oxo-12-(((2S,3R,4R,5R)-2,3,4,5,6-pentahydroxyhexyl)amino)dodecanoyl)piperidin-4-yl)methyl)piperidin-4-yl)methyl)-2,3-dihydrobenzofuran-7-carboxamide;

4-amino-5-chloro-N-((1-((1-(10-oxo-10-(((2S,3R,4R,5R)-2,3,4,5,6-pentahydroxyhexyl)amino)decanoyl)piperidin-4-yl)methyl)piperidin-4-yl)methyl)-2,3-dihydrobenzofuran-7-carboxamide;

4-amino-5-chloro-N-((1-((1-(8-oxo-8-(((2S,3R,4R,5R)-2,3,4,5,6-pentahydroxyhexyl)amino)octanoyl)piperidin-4-yl)methyl)piperidin-4-yl)methyl)-2,3-dihydrobenzofuran-7-carboxamide;

4-amino-5-chloro-N-((3S,4R)-3-methoxy-1-((1-(9-oxo-9-(((2S,3R,4R,5R)-2,3,4,5,6-pentahydroxyhexyl)amino)nonanoyl)piperidin-4-yl)methyl)piperidin-4-yl)-2,3-dihydrobenzofuran-7-carboxamide;

4-amino-5-chloro-N-((3S,4R)-3-methoxy-1-((1-(7-oxo-7-(((2S,3R,4R,5R)-2,3,4,5,6-pentahydroxyhexyl)amino)heptanoyl)piperidin-4-yl)methyl)piperidin-4-yl)-2,3-dihydrobenzofuran-7-carboxamide;

4-amino-5-chloro-N-((3S,4R)-3-methoxy-1-((1-(5-oxo-5-(((2S,3R,4R,5R)-2,3,4,5,6-pentahydroxyhexyl)amino)pentanoyl)piperidin-4-yl)methyl)piperidin-4-yl)-2,3-dihydrobenzofuran-7-carboxamide;

4-amino-5-chloro-N-((3S,4R)-3-methoxy-1-(6-oxo-6-((8-oxo-8-(((2S,3R,4R,5R)-2,3,4,5,6-pentahydroxyhexyl)amino)octyl)amino)hexyl)piperidin-4-yl)-2,3-dihydrobenzofuran-7-carboxamide;

4-amino-5-chloro-N-((3S,4R)-3-methoxy-1-(6-oxo-6-((6-oxo-6-(((2S,3R,4R,5R)-2,3,4,5,6-pentahydroxyhexyl)amino)hexyl)amino)hexyl)piperidin-4-yl)-2,3-dihydrobenzofuran-7-carboxamide;

4-amino-5-chloro-N-((3S,4R)-3-methoxy-1-(6-oxo-6-((4-oxo-4-(((2S,3R,4R,5R)-2,3,4,5,6-pentahydroxyhexyl)amino)butyl)amino)hexyl)piperidin-4-yl)-2,3-dihydrobenzofuran-7-carboxamide; and a pharmaceutically acceptable salt of any one of the aforementioned compounds.

29. A pharmaceutical composition comprising:

a compound or pharmaceutically acceptable salt thereof as defined in claim 1; and a pharmaceutically acceptable excipient.

30. A method for activating 5-$HT_4R$ in a subject, the method comprising administering to the subject a compound or pharmaceutically acceptable salt as defined in claim 1.

31. A method of treating a disease, disorder or condition in a subject, the method comprising administering to the subject a compound or pharmaceutically acceptable salt as defined in claim 1, wherein the disease, disorder or condition is associated with 5-$HT_4R$.

32. A method of treating a disease, disorder or condition in a subject, the method comprising administering to the subject a compound or pharmaceutically acceptable salt as defined in claim 1, wherein the disease, disorder or condition is selected from gastrointestinal motility disorders.

33. A method of treating a disease, disorder or condition in a subject, the method comprising administering to the subject a compound or pharmaceutically acceptable salt as defined in claim 1, wherein the disease, disorder or condition is selected from chronic idiopathic constipation, slow transit constipation, opioid-induced constipation, irritable bowel syndrome, Crohn's Disease, ulcerative colitis, enteral feeding intolerance, postoperative ileus, postoperative gastrointestinal dysfunction, diabetic gastroparesis, idiopathic gastroparesis, functional abdominal pain, chronic intestinal pseudo-obstruction, Hirschsprung Disease, Celiac Disease and short bowel syndrome.

34. A combination comprising a compound or pharmaceutically acceptable salt as defined in claim 1, and at least one additional pharmacologically active agent.

* * * * *